(12) United States Patent
Lee et al.

(10) Patent No.: US 9,885,067 B2
(45) Date of Patent: Feb. 6, 2018

(54) YEAST CELL HAVING DECREASED RGT1 ACTIVITY, METHOD OF PRODUCING THE SAME, AND METHOD OF PRODUCING PRODUCT USING THE SAME

(71) Applicant: SAMSUNG ELECTRONICS CO., LTD., Suwon-si, Gyeonggi-do (KR)

(72) Inventors: Jinsuk Lee, Seongnam-si (KR); Changduk Kang, Gwacheon-si (KR); Seunghyun Lee, Chungcheongnam-do (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/980,983

(22) Filed: Dec. 28, 2015

(65) Prior Publication Data

US 2016/0208270 A1 Jul. 21, 2016

(30) Foreign Application Priority Data

Dec. 26, 2014 (KR) ........................ 10-2014-0191130

(51) Int. Cl.
| | |
|---|---|
| C12N 1/16 | (2006.01) |
| C12P 7/62 | (2006.01) |
| C12P 7/00 | (2006.01) |
| C12P 7/56 | (2006.01) |
| C07K 14/395 | (2006.01) |
| C12N 9/04 | (2006.01) |
| C12N 9/02 | (2006.01) |
| C12N 9/16 | (2006.01) |

(52) U.S. Cl.
CPC ............. *C12P 7/62* (2013.01); *C07K 14/395* (2013.01); *C12N 9/0006* (2013.01); *C12N 9/0008* (2013.01); *C12N 9/16* (2013.01); *C12P 7/00* (2013.01); *C12P 7/56* (2013.01); *C12Y 101/01001* (2013.01); *C12Y 101/01008* (2013.01); *C12Y 101/02003* (2013.01); *C12Y 101/02004* (2013.01); *C12Y 301/03021* (2013.01); *C12Y 401/01001* (2013.01)

(58) Field of Classification Search
CPC ................. C12N 1/16; C12P 7/40; C12P 7/56
USPC .............................. 435/139, 144, 145, 254.2
See application file for complete search history.

(56) References Cited

U.S. PATENT DOCUMENTS

| | | | |
|---|---|---|---|
| 2004/0058429 A1 | 3/2004 | Bill et al. | |
| 2011/0039327 A1 | 2/2011 | Winkler et al. | |
| 2011/0104769 A1* | 5/2011 | Porro | C12N 1/16 435/139 |
| 2013/0244243 A1 | 9/2013 | Matsuyama et al. | |
| 2014/0057323 A1 | 2/2014 | Doudna Cate et al. | |

FOREIGN PATENT DOCUMENTS

| | | |
|---|---|---|
| JP | 2011-193788 A | 10/2011 |
| JP | 2014-506464 | 3/2014 |

OTHER PUBLICATIONS

Rødkær et al., Glucose- and nitrogen sensing and regulatory mechanisms in *Saccharomyces cerevisiae*, FEMS Yeast Res:14:683-696 (2014).

Moriya et al., "Glucose sensing and signaling in *Saccharomyces cerevisiae* through the Rgt2 glucose sensor and casein kinase I", *PNAS*, vol. 101(6): 1572-1577 (2004).

* cited by examiner

*Primary Examiner* — Tekchand Saidha
(74) *Attorney, Agent, or Firm* — Leydig, Voit & Mayer, Ltd.

(57) ABSTRACT

A recombinant yeast cell having a decreased RGT1 protein activity and an increased ability to produce a glycolytic intermediate or a glycolytic intermediate-derived substance, compared to a parent cell; methods of producing the same; and methods of producing the glycolytic intermediate or the glycolytic intermediate-derived substance using the same.

19 Claims, 2 Drawing Sheets

SEQUENCE LISTING

```
<160> NUMBER OF SEQ ID NOS: 105

<210> SEQ ID NO 1
<211> LENGTH: 1170
<212> TYPE: PRT
<213> ORGANISM: Saccharomyces cerevisiae

<400> SEQUENCE: 1
```

Met Asn Glu Leu Asn Thr Val Ser Thr Asn Ser Ser Asp Ser Thr Lys
 1               5                  10                  15

Asn Gly Gly Thr Ser Asn Ser Pro Asp Asp Met Asp Ser Ala Ala Ala
            20                  25                  30

Ala Ser His Ala Ile Lys Lys Arg Thr Lys Ala Ser Arg Ala Cys Asp
        35                  40                  45

```
Gln Cys Arg Lys Lys Ile Lys Cys Asp Tyr Lys Asp Glu Lys Gly
 50                  55                  60

Val Cys Ser Asn Cys Gln Arg Asn Gly Asp Arg Cys Ser Phe Asp Arg
 65                  70                  75                  80

Val Pro Leu Lys Arg Gly Pro Ser Lys Gly Tyr Thr Arg Ser Thr Ser
                 85                  90                  95

His Pro Arg Thr Asn Glu Ile Gln Asp His Asn Asn Ser Arg Ser Tyr
                100                 105                 110

Asn Thr Phe Asp Asn Ser Asn Asn Thr Leu Asn Asn Asn Thr Gly Asn
            115                 120                 125

Ser Gly Asp Asn Gly Ile Asn Ser Asn Thr Val Pro Ser Thr Pro Ser
130                 135                 140

Arg Ser Asn Ser Val Leu Leu Pro Pro Leu Thr Gln Tyr Ile Pro Gln
145                 150                 155                 160

Ala Gly Gly Ile Pro Pro Ser Phe Gln Asn Pro Ala Ile Gln Ser Thr
                165                 170                 175

Met Pro Ala Gly Asn Ile Gly Gln Gln Gln Phe Trp Lys Val Pro Tyr
            180                 185                 190

His Glu Phe Gln His Gln Arg Lys Gly Ser Ile Asp Ser Leu Gln Ser
            195                 200                 205

Asp Ile Ser Val Arg Thr Leu Asn Pro Asn Glu Gln Leu Ser Tyr Asn
210                 215                 220

Thr Val Gln Gln Ser Pro Ile Thr Asn Lys His Thr Asn Asp Ser Gly
225                 230                 235                 240

Asn Ala Asn Gly Ser Val Thr Gly Ser Gly Ser Ala Ser Gly Ser Gly
                245                 250                 255

Gly Tyr Trp Ser Phe Ile Arg Thr Ser Gly Leu Leu Ala Pro Thr Asp
            260                 265                 270

Asp His Asn Gly Glu Gln Thr Arg Arg Ser Ser Ile Pro Ser Leu
            275                 280                 285

Leu Arg Asn Thr Ser Asn Ser Leu Leu Leu Gly Gly Gln Pro Gln Leu
            290                 295                 300

Pro Pro Pro Gln Gln Gln Ser Gln Pro Gln Ala His Gln Gln Lys Leu
305                 310                 315                 320

Gln Gln Gly Gln Asn Leu Tyr Ser Tyr Ser Gln Phe Ser Gln Gln Gln
                325                 330                 335

Pro Tyr Asn Pro Ser Ile Ser Ser Phe Gly Gln Phe Ala Ala Asn Gly
            340                 345                 350

Phe His Ser Arg Gln Gly Ser Val Ala Ser Glu Ala Met Ser Pro Ser
            355                 360                 365

Ala Pro Ala Met Phe Thr Ser Thr Ser Thr Asn Pro Val Asn Val Ala
370                 375                 380

Gln Gln Thr Gln Arg Pro Gln Gly Gln Val Pro Gln Phe Ser Ser
385                 390                 395                 400

Glu Leu Asp Gly Asn Lys Arg Arg Gln Ser Ala Pro Val Ser Val Thr
                405                 410                 415

Leu Ser Thr Asp Arg Leu Asn Gly Asn Glu Asn Asn Gly Glu Ile
            420                 425                 430

Asn Asn Asn Asn Gly Ser Asn Asn Ser Gly Ser Ser Lys Asp Thr Ser
            435                 440                 445

Gln His Ser Gln Glu Ser Val Thr Thr Pro Ala Ala Leu Glu Ala Ser
450                 455                 460
```

```
Ser Pro Gly Ser Thr Pro Gln Arg Ser Thr Lys Lys Arg Lys Ser
465                 470                 475                 480

Tyr Val Ser Lys Lys Thr Lys Pro Lys Arg Asp Ser Ser Ile Ser Ile
                485                 490                 495

Thr Ser Lys Asp Ser Ala His Pro Met Thr Thr Ser Ser Thr Ile Ala
                500                 505                 510

Tyr Gly Gln Ile Ser Asp Val Asp Leu Ile Asp Thr Tyr Tyr Glu Phe
                515                 520                 525

Ile His Val Gly Phe Pro Ile Pro Leu Asn Lys Thr Thr Leu Thr
530                 535                 540

Ser Asp Leu Leu Leu Val Asn Thr Gln Pro Ile Ser Asn Ile His Glu
545                 550                 555                 560

Val Asn Ser Tyr Val Ile Leu Trp Phe Arg Asn Ser Leu Glu Leu Leu
                565                 570                 575

Val Arg Val Ala Leu Lys Gln Lys Pro Gly Gly Lys Phe Phe Asp Asn
                580                 585                 590

Ile Val Gly Val Ala Leu Ser Pro Ser Asn Asp Asn Asn Lys Ala Gly
                595                 600                 605

Phe Thr Thr Ala Thr Ala Arg Asp Asp Ala Glu Lys Thr Arg Arg Asp
610                 615                 620

Ser His Asn Glu Val Gln Asp Thr Leu Glu Val Gln Ser Val Phe Ile
625                 630                 635                 640

Ala Ala Leu Asn Glu Cys Phe Gln Lys Ile Val Asp Ile His Pro Lys
                645                 650                 655

Phe Arg Glu Asn Asn Asp Gln Ile Ser Pro Lys Ile Lys Val Ile Tyr
                660                 665                 670

Leu Ser Thr Phe Ile Leu Leu Asn Tyr Ile Leu Ala Phe Val Gly Tyr
                675                 680                 685

Asp Asn Ser Phe Val Leu Gly Met Ser Val Thr Ile Phe Asn Glu Phe
                690                 695                 700

Lys Leu Tyr Lys Leu Leu Leu Phe Pro Glu Pro Asp Ile Asn Asp Val
705                 710                 715                 720

Lys Pro Pro Val Asp Glu Glu Val Ser Thr Gly Asn Gly Asn Thr Lys
                725                 730                 735

Thr Ser Glu Phe Glu Ile Gly Ser Glu Ser Ala Gly His Met Asn Pro
                740                 745                 750

Ser Asn Ser Pro Asn Ser Met Asp Glu Asn Ile Ser His Tyr Ser Val
                755                 760                 765

Leu Phe Lys Arg Leu Tyr Val Leu Leu Ser Val Phe Asp Ser Leu Gln
                770                 775                 780

Ser Cys Ala Phe Gly Gly Pro Lys Leu Leu Asn Ile Ser Ile Gln Gly
785                 790                 795                 800

Ser Thr Glu Arg Phe Phe Ser Asn Asp Leu Gly Ser Lys Trp Cys Leu
                805                 810                 815

Glu Gln Ser Gln Leu Arg Leu Lys Ser Val Leu Gln Ser Leu Lys Leu
                820                 825                 830

Gly Glu Leu Met Ser Glu Leu Thr Arg Asn Arg Ile Ser Met Asn Gly
                835                 840                 845

Asn Arg Lys Pro Gly Phe Asp Ile Thr Asn Ser Ser Ser Leu Leu Ser
                850                 855                 860

Glu Tyr Val Glu Thr Gln Pro Leu Ser Val Ala Gln Leu Phe Cys Lys
865                 870                 875                 880

Leu Leu Ile Gly Lys His Asn Phe Ile Asn Cys Leu Leu Ser Leu Tyr
```

```
                    885                 890                 895
Asp Ser Glu Ala Gly Val Tyr Ser Asp Leu Thr Leu Asp Leu Ser Ser
            900                 905                 910
Lys Ile Ala Asp Ser Leu Cys Ser Leu Ile Ser Ile Ile Leu Gln Val
            915                 920                 925
Leu Thr Leu Ile Leu Arg Leu Asn Pro Thr Asn Ser Ile Asp Phe Asn
            930                 935                 940
Tyr Arg Pro Pro Asn Pro Pro Ala Asn Asn Pro Thr Val Gln Glu Gly
945                 950                 955                 960
Pro Ser Ala Met Gly Ser Ser Pro Val Ala Gly Asn Leu Ser Ala Ala
            965                 970                 975
Pro Pro Ser Glu Gly Asn Pro Asp Phe Tyr Lys Lys Leu Leu Gly Leu
            980                 985                 990
Lys Gln Asp Thr Gly Thr Ile Leu Ser Asp Leu Cys Arg Gly Ile Ile
            995                 1000                1005
Ser Pro Phe Ala Ile Ala Ile Leu His Glu Val Tyr Asn Ile Thr Glu
            1010                1015                1020
Leu Val Lys Gln Met Pro Thr Ser Leu Ile Ser Ile Met Met Thr Ala
1025                1030                1035                1040
Thr Thr Thr Gln Asn Thr Gln Asp Thr Lys Lys Ser Gln Asp Leu Val
            1045                1050                1055
Met Lys Leu Ser Asn Ser Met Asn Glu Val Val Gln Ile Thr Ser Val
            1060                1065                1070
Leu Thr Met Ile Lys Pro Phe Lys Ile Phe Glu His Glu Leu Asn Lys
            1075                1080                1085
Pro Ile Met Ser Leu Thr Gly Gly Leu Ser Ser Thr Thr Arg Asn Asp
            1090                1095                1100
Val Met Trp Pro Lys Ser Gly Gln Gly Leu Arg Glu Ser Ser Val Met
1105                1110                1115                1120
Lys Thr Leu Leu Asp Glu Arg Arg Thr Ser Gly Thr Gln Pro Thr Thr
            1125                1130                1135
Ala Pro Val Ala Ala Glu Glu Pro Arg Leu Glu Asn Val Ala Leu Glu
            1140                1145                1150
Asn Phe Val Ser Ile Gly Trp Lys Leu Leu Asp Asp Ser Glu Leu Gly
            1155                1160                1165
Trp Tyr
    1170

<210> SEQ ID NO 2
<211> LENGTH: 3513
<212> TYPE: DNA
<213> ORGANISM: Saccharomyces cerevisiae

<400> SEQUENCE: 2
atgaacgagc tgaacactgt ttcgactaac tccagtgact ccaccaagaa cggtggtaca      60
tccaatagtc ccgacgatat ggactccgca gcagcagcaa gtcacgcaat aaagaaaaga     120
acaaaggcct cccgggcctg cgatcagtgt cgtaaaaaga agattaaatg tgactacaaa     180
gatgaaaagg gggtctgctc aaactgccaa aggaatggag accgttgtag ttttgatagg     240
gttcctttga aaggggacct tcgaaaggc tatacgagga gcaccagcca tccaaggact     300
aacgaaatac aagaccacaa taactcaagg tcgtataata cgtttgataa tagtaacaat     360
accctgaata ataatacggg caatagcggc gacaacggta taaacagtaa cacagttcca     420
agtacccctt cgagatctaa ttcagtttta ttgcccccac tgacacagta cattccccag     480
```

```
gctggtggca ttcctcctag tttccaaaat ccagcgatac aatcaactat gcccgcgggt    540
aatattggcc aacagcagtt ttggaaagtg ccctaccatg agtttcaaca ccaaagaaaa    600
ggatctatcg attctttgca aagtgatata tcggtaagaa cattaaatcc caacgagcag    660
ttgtcttata acaccgttca acagtctccc ataacgaata aacatactaa tgattctgga    720
aatgcaaacg gaagtgtcac cggctcaggc agtgcctctg gtagtggtgg ttattggtcc    780
tttataagaa cttctggttt actagctcct actgatgatc ataatgggga acagacaaga    840
agatcaagtt ccatacctttc tttgctacga aatacttcaa attctctttt actaggtggc    900
cagcctcagc ttcccccacc tcagcaacaa tcgcagccac aagcacacca acaaaagttg    960
caacaaggac agaacctata ctcgtattct caattttccc agcagcaacc gtacaaccca   1020
tcgatatcat cttttggcca gttcgctgct aatggttttc attctagaca aggatcagtc   1080
gccagcgagg ctatgtctcc cagtgcacct gccatgttta ctagcacatc tacaaacccc   1140
gtaaatgttg cacagcaaac acaaagacct caaggacagc aggtaccgca atttttcatct   1200 gagttggatg aaataaaag gcgacaatca gcccccgtat cagtaacatt atccacggac   1260
aggctgaatg gtaatgagaa taataatggt gaaattaaca caataatgg cagcaataat   1320 agcggttctt ctaaggatac atctcaacat tcccaagaat ctgtaactac accagcggct   1380
ttggaagcat ccagccctgg atcaacgcca cagagaagta caaaaaaacg cagaaaaagt   1440
tacgtatcta agaagacaaa accaaagaga gattcatcta tatctataac atcgaaagat   1500
tctgctcacc caatgaccac ttcatcaact atcgcgtatg gacagatatc cgatgtagat   1560
ctaatagaca cctactatga gttcatacat gtaggatttc cgatcatacc tttaaacaaa   1620
acgaccttga ccagtgactt attgttagtt aacacacagc caatttccaa tatacacgaa   1680
gtcaattcat atgttatttt gtggtttaga aattcattgg aattgttagt tcgtgttgct   1740
ctgaaacaaa agccaggtgg caagtttttc gataatattg ttggcgtggc tttgtcgcca   1800
agtaatgaca acaacaaagc tgggttcact acagccacgg caagggatga tgctgaaaaa   1860
acaagacgtg attcacataa tgaagtacag gatactttgg aagtgcaaag cgttttttatt   1920 gccgccctca atgaatgttt ccaaaaaatc gtggatattc atcccaaatt cagagaaaac   1980
aacgaccaaa tttcgccgaa gatcaaagtc atttatttat ctacttttat tcttttaaat   2040 tacatttttgg catttgttgg atacgataac tcatttgtac ttgaatgtc ggtgacaatt   2100 tttaacgaat ttaaattata caaacttcta ttatttccgg agccggatat aaatgatgtg   2160
aagcctccag ttgatgaaga ggtcagcact ggtaatggga atacaaaaac gtccgaattt   2220
gaaattggat ctgaaagtgc tgggcatatg aatccatcca attcaccaaa ttccatggac   2280
gaaaacatta gtcactattc agtgttgttt aaaagattat acgttttgct ttcagtgttt   2340
gattctttac aaagctgtgc attcggtggt cccaagctat taaacatttc catccaaggt   2400
tctacagaaa gatttttttc taatgatttg ggctcaaaat ggtgcctgga acaaagccaa   2460
ttgagactga aaagcgtctt gcaaagcttg aaattgggtg aattgatgag tgagcttacc   2520
aggaatagaa tatcaatgaa cggcaatagg aagcctgggt tcgatattac gaactcgtct   2580
tcactcttat cggaatatgt ggaaactcaa cctctatccg tagcacagtt atttttgcaag   2640 ctattaattg gcaaacacaa tttcatcaat tgcttattat cattatacga ttcagaagca   2700
ggagtctatt cagatttgac attggatttg agttcgaaaa tagcagactc tctgtgctca   2760
ttgatatcaa taattttgca agtattgacg ttgatattaa gactgaatcc tacgaacagt   2820
```

-continued

```
attgatttta attatagacc accgaaccca cccgctaata atccgacagt gcaagagggc    2880
ccatctgcta tgggctcgtc tccagtcgct gggaaccttca gcgctgcacc tccatcggag    2940
gggaatccag attttttacaa gaaattacta ggcctgaaac aagacactgg cactatcctt    3000
tcagaccttt gccggggggat aatttccccc tttgctattg ctatcctgca cgaggtctac    3060
aacatcactg aactggtcaa gcagatgcct acatcactca ttagcattat gatgacggca    3120
actacaacgc agaatactca ggacaccaag aagtcgcagg acctggtcat gaagctgtca    3180
aactcgatga atgaagtagt tcaaatcacc agcgtgctga caatgatcaa gccattcaag    3240
atcttcgagc acgagcttaa taagcccata atgtccctga caggaggact ttcgtccacg    3300
accagaaacg acgtcatgtg gccaaagtcg ggccaaggcc tccgcgagtc atcagtcatg    3360
aagacattgc ttgatgaacg ccgtacttct ggtacacaac cgacaacggc gccagtagcc    3420
gcagaggaac ccaggcttga gaacgttgcc ctggaaaatt tcgttagtat cggctggaag    3480
ctgttggacg attccgagtt aggctggtat tga                                 3513
```

<210> SEQ ID NO 3
<211> LENGTH: 486
<212> TYPE: PRT
<213> ORGANISM: Saccharomyces cerevisiae

<400> SEQUENCE: 3

```
Met Val His Leu Gly Pro Lys Lys Pro Gln Ala Arg Lys Gly Ser Met
  1               5                  10                  15

Ala Asp Val Pro Lys Glu Leu Met Gln Gln Ile Glu Asn Phe Glu Lys
             20                  25                  30

Ile Phe Thr Val Pro Thr Glu Thr Leu Gln Ala Val Thr Lys His Phe
         35                  40                  45

Ile Ser Glu Leu Glu Lys Gly Leu Ser Lys Lys Gly Gly Asn Ile Pro
     50                  55                  60

Met Ile Pro Gly Trp Val Met Asp Phe Pro Thr Gly Lys Glu Ser Gly
 65                  70                  75                  80

Asp Phe Leu Ala Ile Asp Leu Gly Gly Thr Asn Leu Arg Val Val Leu
                 85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255
```

```
Asp Ile Pro Pro Ser Ala Pro Met Ala Ile Asn Cys Glu Tyr Gly Ser
              260                 265                 270

Phe Asp Asn Glu His Val Val Leu Pro Arg Thr Lys Tyr Asp Ile Thr
            275                 280                 285

Ile Asp Glu Glu Ser Pro Arg Pro Gly Gln Gln Thr Phe Glu Lys Met
290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
            355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
            435                 440                 445

Tyr Pro Ile Lys Ile Val Pro Ala Glu Asp Gly Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 4
<211> LENGTH: 1461
<212> TYPE: DNA
<213> ORGANISM: Saccharomyces cerevisiae

<400> SEQUENCE: 4
atggttcatt taggtccaaa aaaaccacaa gccagaaagg gttccatggc cgatgtgcca      60
aaggaattga tgcaacaaat tgagaatttt gaaaaaattt tcactgttcc aactgaaact     120
ttacaagccg ttaccaagca cttcatttcc gaattggaaa agggtttgtc caagaagggt     180
ggtaacattc caatgattcc aggttgggtt atggatttcc caactggtaa ggaatccggt     240
gatttcttgg ccattgattt gggtggtacc aacttgagag ttgtcttagt caagttgggc     300
ggtgaccgta cctttgacac cactcaatct aagtacagat accagatgc tatgagaact      360 actcaaaatc cagacgaatt gtgggaattt attgccgact ctttgaaagc ttttattgat     420
gagcaattcc cacaaggtat ctctgagcca attccattgg gtttcacctt tctttcccca     480
gcttctcaaa acaaaatcaa tgaaggtatc ttgcaaagat ggactaaagg ttttgatatt     540
ccaaacattg aaaaccacga tgttgttcca atgttgcaaa agcaaatcac taagaggaat     600
atcccaattg aagttgttgc tttgataaac gacactaccg gtactttggt tgcttcttac     660
tacactgacc cagaaactaa gatgggtgtt atcttcggta ctggtgtcaa tggtgcttac     720
tacgatgttt gttccgatat cgaaaagcta caaggaaaac tatctgatga cattccacca     780
```

-continued

```
tctgctccaa tggccatcaa ctgtgaatac ggttccttcg ataatgaaca tgtcgttttg    840
ccaagaacta aatacgatat caccattgat gaagaatctc caagaccagg ccaacaaacc    900
tttgaaaaaa tgtcttctgg ttactactta ggtgaaattt tgcgtttggc cttgatggac    960
atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga cgtaaattg    1140 atcagacgtt tatctgaatt gattggtgct agagctgcta gattgtccgt tgtggtatt    1200 gctgctatct gtcaaaagag aggttacaag accggtcaca tcgctgcaga cggttccgtt   1260
tacaacagat acccaggttt caaagaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                             1461
```

```
<210> SEQ ID NO 5
<211> LENGTH: 332
<212> TYPE: PRT
<213> ORGANISM: Pelodiscus sinensis japonicus
<220> FEATURE:
<221> NAME/KEY: MISC FEATURE
<222> LOCATION: (1)..(332)
<223> OTHER INFORMATION: LDH protein

<400> SEQUENCE: 5
```

Met Ser Val Lys Glu Leu Leu Ile Gln Asn Val His Lys Glu Glu His
 1               5                   10                  15

Ser His Ala His Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Arg Gly Glu Met Leu Asp
        50                  55                  60

Leu Gln His Gly Ser Leu Phe Leu Arg Thr Pro Lys Ile Val Ser Gly
    65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 6
<211> LENGTH: 999
<212> TYPE: DNA
<213> ORGANISM: Pelodiscus sinensis japonicus
<220> FEATURE:
<221> NAME/KEY: MISC FEATURE
<222> LOCATION: (1)..(999)
<223> OTHER INFORMATION: LDH gene

<400> SEQUENCE: 6
atgtccgtaa aggaactact tatacaaaac gtccataagg aggagcattc tcacgctcac        60
aataagataa cagttgtagg agtaggtgca gtaggtatgg catgtgctat ttcgatatta      120
atgaaagact tggctgatga actagccttg gttgatgtga ttgaggataa gttacgtgga      180
gaaatgttag atttgcaaca tggttcattg ttcttgagaa ccccccaaaat tgtctcgggt     240 aaggattatt cagtcactgc tcattctaaa ctggttatca ttacagcagg tgcaagacag      300
caagaagggg agagcagact aaatctggtt caacgtaatg tcaacatctt caagtttatc      360
atcccgaacg tagtaaaata cagtccagac tgcatgttgc ttgttgtgag taatccagtt      420
gacatcttaa cctatgttgc gtggaaaatc agtgggtttc aaaacatag gtgattggc        480 tcaggatgca accttgatag cgccaggttt aggtatctaa tgggagaaaa attaggtatt      540
cactccttat cttgtcatgg ctggataata ggcgaacatg gtgattcttc ggtacctgtt      600
tggtccgggg ttaatgtggc tggtgttagt ttaaaagcat tatatcctga cctgggtact     660
gatgccgata agaacattg gaaagaagtg cacaaacaag tggttgattc tgcttacgaa      720
gttattaaac ttaagggcta cacttcttgg gctataggtc tatcagtagc tgatttggca      780 gaaccgtta tgaaaaattt aagaagagtc cacccaattt ccacgatggt caagggtatg      840
tacggtgtta gctctgacgt cttcttatct gttccttgtg ttttgggata tgcgggaatt      900
acagacgtcg tgaagatgac attgaaatca gaggaagagg aaaaactaag aaagtcagcc      960
gatactctgt ggggcattca aaaggaattg cagttttaa                             999

<210> SEQ ID NO 7
<211> LENGTH: 332
<212> TYPE: PRT
<213> ORGANISM: Ornithorhynchus anatinus
<220> FEATURE:
<221> NAME/KEY: MISC FEATURE
<222> LOCATION: (1)..(332)
<223> OTHER INFORMATION: LDH protein

<400> SEQUENCE: 7

```
Met Ala Gly Val Lys Glu Gln Leu Ile Gln Asn Leu Leu Lys Glu Glu
 1               5                  10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Asn Cys Lys Leu Leu Val Val Ser Asn Pro Val Asp Ile Leu Thr
        130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
            195                 200                 205

Val Ser Leu Lys Asn Leu His Pro Asp Leu Gly Thr Asp Ala Asp Lys
210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
            290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330
```

<210> SEQ ID NO 8
<211> LENGTH: 332
<212> TYPE: PRT
<213> ORGANISM: Tursiops truncates
<220> FEATURE:
<221> NAME/KEY: MISC FEATURE
<222> LOCATION: (1)..(332)
<223> OTHER INFORMATION: LDH protein

<400> SEQUENCE: 8

```
Met Ala Thr Val Lys Asp Gln Leu Ile Gln Asn Leu Leu Lys Glu Glu
 1               5                  10                  15

His Val Pro Gln Asn Lys Ile Thr Val Val Gly Val Gly Ala Val Gly
```

```
            20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Lys Gly Glu Met Met Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 9
<211> LENGTH: 332
<212> TYPE: PRT
<213> ORGANISM: Rattus norvegicus
<220> FEATURE:
<221> NAME/KEY: MISC FEATURE
<222> LOCATION: (1)..(332)
<223> OTHER INFORMATION: LDH protein

<400> SEQUENCE: 9

Met Ala Ala Leu Lys Asp Gln Leu Ile Val Asn Leu Leu Lys Glu Glu
 1               5                  10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
         35                  40                  45
```

Ala Leu Val Asp Val Ile Glu Asp Lys Leu Lys Gly Glu Met Met Asp
 50                  55                  60

Leu Gln His Gly Ser Leu Phe Leu Lys Thr Pro Lys Ile Val Ser Ser
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
             100                 105                 110

Asn Val Asn Ile Phe Lys Phe Ile Pro Asn Val Val Lys Tyr Ser
         115                 120                 125

Pro Gln Cys Lys Leu Leu Ile Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
                180                 185                 190

His Gly Asp Ser Ser Val Pro Val Trp Ser Gly Val Asn Val Ala Gly
                195                 200                 205

Val Ser Leu Lys Ser Leu Asn Pro Gln Leu Gly Thr Asp Ala Asp Lys
210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
                260                 265                 270

Ile Ser Thr Met Ile Lys Gly Leu Tyr Gly Ile Lys Glu Asp Val Phe
                275                 280                 285

Leu Ser Val Pro Cys Ile Leu Gly Gln Asn Gly Ile Ser Asp Val Val
                290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 10
<211> LENGTH: 1140
<212> TYPE: DNA
<213> ORGANISM: Ornithorhynchus anatinus

<400> SEQUENCE: 10
ttccaagatg gccggcgtca aggaacagct gatccagaat cttctcaaag aggagtacgc      60
ccctcaaaat aagatcaccg tggttggagt tggtgctgtg ggcatggcct gtgccatcag     120
catcttgatg aaggatttgg ctgatgagct cgcccttgtt gatgtcattg aggataagct     180
gaagggagaa atgatggatc ttcagcatgg cagccttttc ctcaggactc caaagatcgt     240
ctctggcaaa gactacagcg tgactgccaa ctccaagctg gttatcatca ccgcgggggc     300
ccgtcagcag gagggagaga gccgtctgaa tctggtccag cgcaatgtca acatctttaa     360
attcatcatt cccaacgttg tcaagtacag ccccaactgc aagctgcttg tggtgtccaa     420
tccagtggat attttgacct acgtggcctg gaagatcagt ggcttcccca agaaccgagt     480

```
tatcggaagc ggctgcaatc tggattctgc ccgcttccgc tatctgatgg gagagaggct    540
gggcatccac tccacaagct gtcacggctg ggtcatcgga gaacacggag actctagtgt    600
tcccgtgtgg agcggggtga acgttgccgg tgtctctctg aagaacctgc accccgattt    660
gggaactgat gcagacaagg agcagtggaa ggatgttcat aagcaggtgg ttgacagtgc    720
ctacgaggtc atcaaactga agggctacac ctcctgggcc atcggcctct cggtagccga    780
tctggcagaa agcatcgtga agaatcttag gcgggtgcac cccatttcca ccatgattaa    840
gggcctgtac gggatcaaag atgaagtctt cctcagcgtc ccctgtgtct gggccagaa     900
cggcatctcg gacgtggtga agataaccct gaagtccgag gaggaggctc atctgaagaa    960
gagcgcagac accctgtggg gaattcagaa ggaactgcag ttttaaggct tttcaacatc   1020
ctagctgtct actgggtaac ggtagttagg ggattgggta tcccccactt ttgaagtagg   1080
ttagctgtct actgggtaac ggtagttagg ggattgggta tcccccactt ttgaagtagg   1140

<210> SEQ ID NO 11
<211> LENGTH: 1527
<212> TYPE: DNA
<213> ORGANISM: Tursiops truncatus

<400> SEQUENCE: 11
acgtgtactc ccgattcctt tcggttctaa gtccaatatg gcaactgtca aggatcagct     60
gattcagaat cttcttaagg aagaacatgt cccccagaat aagattacag tggttggtgt    120
tggtgctgtt ggcatggcct gtgccatcag tatcttaatg aaggacttgg cagatgaact    180
tgctcttgtt gatgtcatag aagacaaact gaagggagag atgatggatc tccaacatgg    240
cagccttttc cttagaacac caaaaatcgt ctctggcaaa gactatagtg tgacagcaaa    300
ctccaagctg gttattatca cagctggggc acgtcagcaa gagggagaaa gccgtcttaa    360
tttggtccaa cgtaatgtga acatctttaa attcatcgtt cctaatattg taaaatacag    420
cccacactga agttgcttg ttgtttccaa tccagtggat atcttgacct atgtggcttg    480
gaagataagc ggcttttccca aaaccgtgt tattggaagt ggttgcaatt tggattcagc    540
ccggttccgt tacctcatgg gggaaaggct gggagttcac ccattaagct gtcatggatg    600
gatccttggg gagcatggag actctagtgt gcctgtatgg agtggagtga atgttgctgg    660
tgtctccctg aagaatctgc accccgaatt aggcactgat gccgataagg aacattggaa    720
agcaattcac aaacaggtgg ttgacagtgc ttatgaggtg atcaaactga aggctacac     780
atcctgggcc gttggactat ctgtggcaga tttggcagaa agtataatga gaatcttag    840
gcgggtgcat ccgatttcca ccatgattaa gggtttgtat ggaataaaag aggatgtctt    900
ccttagtgtt ccttgcatct tgggacagaa tggaatctca gatgttgtga agtgactct    960
gactcctgag gaacaggcct gtttgaagaa gagtgcagat acactttggg ggatccagaa   1020
agagctgcag ttttaaagtc taatatcata ccacttcact gtctaggcta caataggatt   1080
ttagttggag gttgtgcata ttgtcctta tatctgatct gtgactaaag cagtaatgtt   1140
aagacagcct aggaaaaaca tcaatttcct aacattagca ataggaatgg ttcataaaac   1200
cctgcagctg tatcctgatg ctgcatggca cttatcttgt gttgtcctaa attggttcgt   1260
gtaaaatagt tctacttcct caagaggtac cactgacagt gttgcagatg ctgcagttgc   1320
ccttcaaacc agatgtgtat ttaactctgt gttatataac ttctggttcc tttagccaag   1380
atgcctagtc caacttttttt ctctccaatt aatcacattc tgggattgat tataaatcca   1440
gtattgcatg tcttgtgcat aactgttcta aagaatctta tttttatgtac tatatgtatc   1500
```
agaatagtat acattgccat gtaatgt                                    1527

<210> SEQ ID NO 12
<211> LENGTH: 1609
<212> TYPE: DNA
<213> ORGANISM: Rattus norvegicus

<400> SEQUENCE: 12
gtgtgctgga gccactgtcg ccgatctcgc gcacgctact gctgctgctc gcccgtcgtc      60
ccccatcgtg cactaagcgg tcccaaaaga ttcaaagtcc aagatggcag ccctcaagga     120
ccagctgatt gtgaatcttc ttaaggaaga acaggtcccc cagaacaaga ttacagttgt     180
tggggttggt gctgttggca tggcttgtgc catcagtatc ttaatgaagg acttggctga     240
tgagcttgcc cttgttgatg tcatagaaga taagctaaag ggagagatga tggatcttca     300
gcatggcagc cttttcctta agacaccaaa aattgtctcc agcaaagatt atagtgtgac     360
tgcaaactcc aagctggtca ttatcaccgc gggggcccgt cagcaagagg gagagagccg     420
gctcaatttg gtccagcgaa acgtgaacat cttcaagttc atcattccaa atgttgtgaa     480
atacagtcca cagtgcaaac tgctcatcgt ctcaaaccca gtggatatct tgacctacgt     540
ggcttggaag atcagcggct tccccaaaaa cagagttatt ggaagtggtt gcaatctgga     600
ttcggctcgg ttccgttacc tgatgggaga aaggctggga gttcatccac tgagctgtca     660
cgggtgggtc ctgggagagc atggcgactc cagtgtgcct gtgtggagtg tgtgtgaacgt     720
cgccggcgtc tccctgaagt ctctgaaccc gcagctgggc acggatgcag acaaggagca     780
gtggaaggat gtgcacaagc aggtggttga cagtgcatac gaagtgatca agctgaaagg     840
ttacacatcc tgggccattg gcctctccgt ggcagacttg gccgagagca taatgaagaa     900
ccttaggcgg gtgcatccca tttccaccat gattaagggt ctctatggaa tcaaggagga     960
tgtcttcctc agcgtcccat gtatcctggg acaaaatgga atctcagatg ttgtgaaggt    1020
gacactgact cctgacgagg aggcccgcct gaagaagagt gcagataccc tctggggaat    1080
ccagaaggag ctgcagttct aaagtcttcc cagtgtccta gcacttcact gtccaggctg    1140
cagcagggtt tctatggaga ccacgcactt ctcatctgag ctgtggttag tccagttggt    1200
ccagttgtgt tgaggtggtc tgggggaaat ctcagttcca cagctctacc ctgctaagtg    1260
gtacttgtgt agtggtaacc tggttagtgt gacaatccca ctgtctccaa gacacactgc    1320
caactgcatg caggctttga ttaccctgtg agcctgctgc attgctgtgc tacgcaccct    1380
caccaaacat gcctaggcca tgagttccca gttagttata agctggctcc agtgtgtaag    1440
tccatcgtgt atatcttgtg cataaatgtt ctacaggata ttttctgtat tatatgtgtc    1500
tgtagtgtac attgcaatat tacgtgaaat gtaagatctg catatggatg atggaaccaa    1560
ccactcaagt gtcatgccaa ggaaaacacc aaataaacct tgaacagtg              1609

<210> SEQ ID NO 13
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 13
ttcgcggcca cctacgccgc tatctttgca acaactatct gcgataactc agcaaatttt      60
gcatattcgt gttgcagtat tgcgataatg ggagtcttac ttccaacata acggcagaaa     120

| | |
|---|---|
| gaaatgtgag aaaattttgc atcctttgcc tccgttcaag tatataaagt cggcatgctt | 180 |
| gataatcttt ctttccatcc tacattgttc taattattct tattctcctt tattctttcc | 240 |
| taacatacca agaaattaat cttctgtcat tcgcttaaac actatatcaa ta | 292 |

```
<210> SEQ ID NO 14
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 14
```

| | |
|---|---|
| atttggcgag cgttggttgg tggatcaagc ccacgcgtag gcaatcctcg agcagatccg | 60 |
| ccaggcgtgt atatatagcg tggatggcca ggcaacttta gtgctgacac atacaggcat | 120 |
| atatatatgt gtgcgacgac acatgatcat atggcatgca tgtgctctgt atgtatataa | 180 |
| aactcttgtt ttcttctttt ctctaaatat tctttcctta tacattagga cctttgcagc | 240 |
| ataaattact atacttctat agacacgcaa acacaaatac acacactaa | 289 |

```
<210> SEQ ID NO 15
<211> LENGTH: 401
<212> TYPE: DNA
<213> ORGANISM: Artificial Sequence
<220> FEATURE:
<223> OTHER INFORMATION: Synthetic TEF1 promoter

<400> SEQUENCE: 15
```

| | |
|---|---|
| atagcttcaa aatgtttcta ctccttttt actcttccag attttctcgg actccgcgca | 60 |
| tcgccgtacc acttcaaaac acccaagcac agcatactaa atttcccctc tttcttcctc | 120 |
| tagggtgtcg ttaattaccc gtactaaagg tttggaaaag aaaaaagaga ccgcctcgtt | 180 |
| tctttttctt cgtcgaaaaa ggcaataaaa atttttatca cgtttctttt tcttgaaaat | 240 |
| tttttttttg atttttttct ctttcgatga cctcccattg atatttaagt taataaacgg | 300 |
| tcttcaattt ctcaagtttc agtttcattt tcttgttcct attacaactt ttttttacttc | 360 |
| ttgctcatta gaaagaaagc atagcaatct aatctaagtt t | 401 |

```
<210> SEQ ID NO 16
<211> LENGTH: 798
<212> TYPE: DNA
<213> ORGANISM: Artificial Sequence
<220> FEATURE:
<223> OTHER INFORMATION: Synthetic PGK1 promoter

<400> SEQUENCE: 16
```

| | |
|---|---|
| ctttcctctt tttattaacc ttaatttta ttttagattc ctgacttcaa ctcaagacgc | 60 |
| acagatatta taacatctgc ataataggca tttgcaagaa ttactcgtga gtaaggaaag | 120 |
| agtgaggaac tatcgcatac ctgcatttaa agatgccgat ttgggcgcga atcctttatt | 180 |
| ttggcttcac cctcatacta ttatcagggc cagaaaaagg aagtgtttcc ctccttcttg | 240 |
| aattgatgtt accctcataa agcacgtggc ctcttatcga gaaagaaatt accgtcgctc | 300 |
| gtgatttgtt tgcaaaaaga acaaaactga aaaacccag acacgctcga cttcctgtct | 360 |
| tcctattgat tgcagcttcc aatttcgtca cacaacaagg tcctagcgac ggctcacagg | 420 |
| ttttgtaaca agcaatcgaa ggttctggaa tggcgggaaa gggtttagta ccacatgcta | 480 |
| tgatgcccac tgtgatctcc agagcaaagt tcgttcgatc gtactgttac tctctctctt | 540 |
| tcaaacagaa ttgtccgaat cgtgtgacaa caacagcctg ttctcacaca ctcttttctt | 600 |

```
ctaaccaagg gggtggttta gtttagtaga acctcgtgaa acttacattt acatatatat    660
aaacttgcat aaattggtca atgcaagaaa tacatatttg gtcttttcta attcgtagtt    720
tttcaagttc ttagatgctt tcttttttctc ttttttacag atcatcaagg aagtaattat    780 ctactttta caacaaat                                                   798
```

```
<210> SEQ ID NO 17
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 17
agtttatcat tatcaatact cgccatttca agaatacgt aaataattaa tagtagtgat     60
tttcctaact ttatttagtc aaaaaattag ccttttaatt ctgctgtaac ccgtacatgc   120
ccaaaatagg gggcgggtta cacagaatat ataacatcgt aggtgtctgg gtgaacagtt   180
tattcctggc atccactaaa tataatggag cccgcttttt aagctggcat ccagaaaaaa   240
aaagaatccc agcaccaaaa tattgttttc ttcaccaacc atcagttcat aggtccattc   300
tcttagcgca actacagaga acaggggcac aaacaggcaa aaacgggca caacctcaat   360 ggagtgatgc aacctgcctg gagtaaatga tgacacaagg caattgaccc acgcatgtat   420
ctatctcatt ttcttacacc ttctattacc ttctgctctc tctgatttgg aaaaagctga   480
aaaaaaaggt tgaaaccagt tccctgaaat tattccccta cttgactaat aagtatataa   540
agacggtagg tattgattgt aattctgtaa atctatttct taaacttctt aaattctact   600
tttatagtta gtctttttt tagttttaaa acaccagaac ttagtttcga cggat         655
```

```
<210> SEQ ID NO 18
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 18
gccgggatcg aagaaatgat ggtaaatgaa ataggaaatc aaggagcatg aaggcaaaag    60
acaaatataa gggtcgaacg aaaaataaag tgaaaagtgt tgatatgatg tatttggctt   120
tgcggcgccg aaaaaacgag tttacgcaat tgcacaatca tgctgactct gtggcggacc   180
cgcgctcttg ccgcccggc gataacgctg ggcgtgaggc tgtgcccggc ggagtttttt   240
gcgcctgcat tttccaaggt ttaccctgcg ctaagggcg agattggaga agcaataaga   300
atgccggttg gggttgcgat gatgacgacc acgacaactg tgtcattat ttaagttgcc   360 gaaagaacct gagtgcattt gcaacatgag tatactagaa gaatgagcca agacttgcga   420
gacgcgagtt tgccggtggt gcgaacaata gagcgaccat gaccttgaag gtgagacgcg   480
cataaccgct agagtacttt gaagaggaaa cagcaatagg gttgctacca gtataaatag   540
acaggtacat acaacactgg aaatggttgt ctgtttgagt acgctttcaa ttcatttggg   600
tgtgcacttt attatgttac aatatggaag gaactttac acttctccta tgcacatata   660
ttaattaaag tccaatgcta gtagagaagg ggggtaacac ccctccgcgc tcttttccga   720
tttttttcta aaccgtggaa tatttcggat atccttttgt tgtttccggg tgtacaatat   780
ggacttcctc ttttctggca accaaaccca tacatcggga ttcctataat accttcgttg   840
```

```
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actaccctt     1020 ttccatttgc catctattga agtaataata ggcgcatgca acttcttttc tttttttttc    1080
ttttctctct cccccgttgt tgtctcacca tatccgcaat gacaaaaaaa tgatggaaga    1140
cactaaagga aaaattaac gacaaagaca gcaccaacag atgtcgttgt tccagagctg    1200 atgagggta tctcgaagca cacgaaactt tttccttcct tcattcacgc acactactct    1260
ctaatgagca acggtatacg gccttccttc cagttacttg aatttgaaat aaaaaaaagt    1320
ttgctgtctt gctatcaagt ataaatagac ctgcaattat taatcttttg tttcctcgtc    1380
attgttctcg ttccctttct tccttgtttc tttttctgca caatatttca agctatacca    1440
agcatacaat caactccaag ctggccgc                                        1468
```

<210> SEQ ID NO 19
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 19

```
tcatgtaatt agttatgtca cgcttacatt cacgccctcc ccccacatcc gctctaaccg     60
aaaaggaagg agttagacaa cctgaagtct aggtccctat ttatttttt atagttatgt    120 tagtattaag aacgttattt atatttcaaa ttttctttt ttttctgtac agacgcgtgt    180
acgcatgtaa cattatactg aaaaccttgc ttgagaaggt tttgggacgc tcgaaggctt    240
taatttgcgg cc                                                         252
```

<210> SEQ ID NO 20
<211> LENGTH: 1047
<212> TYPE: DNA
<213> ORGANISM: Saccharomyces cerevisiae

<400> SEQUENCE: 20

```
atgtctatcc cagaaactca aaaggtgtt atcttctacg aatcccacgg taagttggaa      60
tacaaagata ttccagttcc aaagccaaag gccaacgaat tgttgatcaa cgttaaatac    120
tctggtgtct gtcacactga cttgcacgct tggcacggtg actggccatt gccagttaag    180
ctaccattag ttggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttctttcca agaatacgct accgctgacg ctgttcaagc cgctcacatt    420
cctcaaggta ctgacttggc tgaagtcgcc ccagttttgt gtgctggtat caccgtctac    480
aaggctttga gtctgctaa cttgatggcc ggtcactggg ttgctatctc cggtgctgct    540
ggtggtctag gttctttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttccac cagatacgtt    780
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
```

```
gacaccagag aagctttgga cttcttcgcc agaggtttga tcaagtctcc aatcaaggtt        960
gtcggcttgt ctaccttgcc agaaatttac gaaaagatgg aaaagggtca atcgttggt       1020 agatacgttg ttgacacttc taaataa                                          1047
```

<210> SEQ ID NO 21
<211> LENGTH: 348
<212> TYPE: PRT
<213> ORGANISM: Saccharomyces cerevisiae

<400> SEQUENCE: 21

```
Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
                 20                  25                  30

Glu Leu Leu Ile Asn Val Lys Tyr Ser Gly Val Cys His Thr Asp Leu
             35                  40                  45

His Ala Trp His Gly Asp Trp Pro Leu Pro Val Lys Leu Pro Leu Val
         50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
```

340          345

<210> SEQ ID NO 22
<211> LENGTH: 563
<212> TYPE: PRT
<213> ORGANISM: Saccharomyces cerevisia

<400> SEQUENCE: 22

```
Met Ser Glu Ile Thr Leu Gly Lys Tyr Leu Phe Glu Arg Leu Lys Gln
 1               5                  10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365
```

```
Trp Met Trp Asn Gln Leu Gly Asn Phe Leu Gln Glu Gly Asp Val Val
    370             375                 380
Ile Ala Glu Thr Gly Thr Ser Ala Phe Gly Ile Asn Gln Thr Thr Phe
385             390              395                  400
Pro Asn Asn Thr Tyr Gly Ile Ser Gln Val Leu Trp Gly Ser Ile Gly
            405                 410                 415
Phe Thr Thr Gly Ala Thr Leu Gly Ala Ala Phe Ala Ala Glu Glu Ile
            420              425              430
Asp Pro Lys Lys Arg Val Ile Leu Phe Ile Gly Asp Gly Ser Leu Gln
            435                 440              445
Leu Thr Val Gln Glu Ile Ser Thr Met Ile Arg Trp Gly Leu Lys Pro
450                 455                 460
Tyr Leu Phe Val Leu Asn Asn Asp Gly Tyr Thr Ile Glu Lys Leu Ile
465             470              475                  480
His Gly Pro Lys Ala Gln Tyr Asn Glu Ile Gln Gly Trp Asp His Leu
                485              490                 495
Ser Leu Leu Pro Thr Phe Gly Ala Lys Asp Tyr Glu Thr His Arg Val
            500              505              510
Ala Thr Thr Gly Glu Trp Asp Lys Leu Thr Gln Asp Lys Ser Phe Asn
            515              520              525
Asp Asn Ser Lys Ile Arg Met Ile Glu Ile Met Leu Pro Val Phe Asp
530             535                 540
Ala Pro Gln Asn Leu Val Glu Gln Ala Lys Leu Thr Ala Ala Thr Asn
545             550                 555                 560
Ala Lys Gln
```

<210> SEQ ID NO 23
<211> LENGTH: 1692
<212> TYPE: DNA
<213> ORGANISM: Saccharomyces cerevisiae

<400> SEQUENCE: 23

```
atgtctgaaa ttactttggg taaatatttg ttcgaaagat taaagcaagt caacgttaac    60
accgttttcg gtttgccagg tgacttcaac ttgtccttgt ggacaagat ctacgaagtt     120
gaaggtatga gatgggctgg taacgccaac gaattgaacg ctgcttacgc cgctgatggt    180
tacgctcgta tcaagggtat gtcttgtatc atcaccacct cggtgtcgg tgaattgtct     240
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact gaacgtccc agctaagttg     540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca gaacattgtc gaattccac tccgaccaca tgaagatcag aaacgccact    960
ttcccaggtg tccaaatgaa attcgttttg caaaagttgt tgaccactat tgctgacgcc   1020
```

-continued

```
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga aaccggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc caagaagag agttatctta    1320 ttcattggtg acggttcttt gcaattgact gttcaagaaa tctccaccat gatcagatgg    1380
ggcttgaagc atacttgtt cgtcttgaac aacgatggtt acaccattga aaagttgatt    1440
cacggtccaa aggctcaata caacgaaatt caaggttggg accacctatc cttgttgcca    1500
actttcggtg ctaaggacta tgaaacccac agagtcgcta ccaccggtga atgggacaag    1560
ttgacccaag acaagtcttt caacgacaac tctaagatca gaatgattga aatcatgttg    1620
ccagtcttcg atgctccaca aaacttggtt gaacaagcta agttgactgc tgctaccaac    1680
gctaagcaat aa                                                         1692
```

<210> SEQ ID NO 24
<211> LENGTH: 591
<212> TYPE: PRT
<213> ORGANISM: Saccharomyces cerevisiae

<400> SEQUENCE: 24

```
Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
```

245                 250                 255
Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
    435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 25
<211> LENGTH: 1776
<212> TYPE: DNA
<213> ORGANISM: Saccharomyces cerevisiae

<400> SEQUENCE: 25
atgctaaaat acaaaccttt actaaaaatc tcgaagaact gtgaggctgc tatcctcaga    60
gcgtctaaga ctagattgaa cacaatccgc gcgtacggtt ctaccgttcc aaaatccaag   120
tcgttcgaac aagactcaag aaaacgcaca cagtcatgga ctgccttgag agtcggtgca   180

-continued

```
attctagccg ctactagttc cgtggcgtat ctaaactggc ataatggcca aatagacaac      240 gagcccgaaac tggatatgaa taaacaaaag atttcgcccg ctgaagttgc caagcataac    300
aagcccgatg attgttgggt tgtgatcaat ggttacgtat acgacttaac gcgattccta    360
ccaaatcatc caggtgggca ggatgttatc aagtttaacg ccgggaaaga tgtcactgct    420 attttttgaac cactacatgc tcctaatgtc atcgataagt atatagctcc cgagaaaaaa    480
ttgggtcccc ttcaaggatc catgcctcct gaacttgtct gtcctcctta tgctcctggt    540
gaaactaagg aagatatcgc tagaaaagaa caactaaaat cgctgctacc tcctctagat    600
aatattatta acctttacga ctttgaatac ttggcctctc aaactttgac taaacaagcg    660
tgggcctact attcctccgg tgctaacgac gaagttactc acagagaaaa ccataatgct    720
tatcatagga ttttttttcaa accaaagatc cttgtagatg tacgcaaagt agacatttca    780
actgacatgt tgggttctca tgtggatgtt cccttctacg tgtctgctac agctttgtgt    840
aaactgggaa acccccttaga aggtgaaaaa gatgtcgcca gaggttgtgg ccaaggtgtg    900
acaaaagtcc cacaaatgat atctactttg gcttcatgtt cccctgagga aattattgaa    960
gcagcaccct ctgataaaca aattcaatgg taccaactat atgttaactc tgatagaaag   1020
atcactgatg atttggttaa aaatgtagaa agctgggtg taaaggcatt atttgtcact   1080
gtggatgctc caagtttagg tcaaagagaa aaagatatga agctgaaatt ttccaataca   1140
aaggctggtc caaaagcgat gaagaaaact aatgtagaag aatctcaagg tgcttcgaga   1200
gcgttatcaa agtttattga ccccctcttg acttggaaag atatagaaga gttgaagaaa   1260
aagacaaaac tacctattgt tatcaaaggt gttcaacgta ccgaagatgt tatcaaagca   1320
gcagaaatcg gtgtaagtgg ggtggttcta tccaatcatg gtggtagaca attagatttt   1380
tcaagggctc ccattgaagt cctggctgaa accatgccaa tcctggaaca acgtaacttg   1440
aaggataagt tggaagttt cgtggacggt ggtgttcgtc gtggtacaga tgtcttgaaa   1500
gcgttatgtc taggtgctaa aggtgttggt ttgggtagac cattcttgta tgcgaactca   1560
tgctatggtc gtaatggtgt tgaaaaagcc attgaaattt taagagatga aattgaaatg   1620
tctatgagac tattaggtgt tactagcatt gcggaattga gcctgatct tttagatcta   1680 tcaacactaa aggcaagaac agttggagta ccaaacgacg tgctgtataa tgaagtttat   1740
gagggaccta ctttaacaga atttgaggat gcatga                            1776
```

<210> SEQ ID NO 26
<211> LENGTH: 391
<212> TYPE: PRT
<213> ORGANISM: Saccharomyces cerevisiae

<400> SEQUENCE: 26

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

```
Pro Gly Ile Thr Leu Pro Asp Asn Leu Val Ala Asn Pro Asp Leu Ile
            100                 105                 110

Asp Ser Val Lys Asp Val Asp Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 27
<211> LENGTH: 1176
<212> TYPE: DNA
<213> ORGANISM: Saccharomyces cerevisiae

<400> SEQUENCE: 27
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt cgctccaat agtacaaatg tgggtgttcg aagaagagat caatggtgaa     240
aaattgactg aaatcataaa tactagacat caaaacgtga atacttgcc tggcatcact     300 ctaccccgaca atttggttgc taatccagac ttgattgatt cagtcaagga tgtcgacatc    360
atcgttttca acattccaca tcaatttttg ccccgtatct gtagccaatt gaaaggtcat    420
```

```
gttgattcac acgtcagagc tatctcctgt ctaaagggtt ttgaagttgg tgctaaaggt      480
gtccaattgc tatcctctta catcactgag aactaggta ttcaatgtgg tgctctatct      540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                             1176

<210> SEQ ID NO 28
<211> LENGTH: 753
<212> TYPE: DNA
<213> ORGANISM: Saccharomyces cerevisiae

<400> SEQUENCE: 28
atgcctttga ccacaaaacc tttatctttg aaaatcaacg ccgctctatt cgatgttgac      60
ggtaccatca tcatctctca accagccatt gctgctttct ggagagattt cggtaaagac     120
aagccttact tcgatgccga acacgttatt cacatctctc acggttggag aacttacgat     180
gccattgcca agttcgctcc agactttgct gatgaagaat acgttaacaa gctagaaggt     240
gaaatcccag aaaagtacgg tgaacactcc atcgaagttc caggtgctgt caagttgtgt     300
aatgctttga acgccttgcc aaaggaaaaa tgggctgtcg ccacctctgg tacccgtgac     360
atggccaaga atggttcga cattttgaag atcaagagac cagaatactt catcaccgcc     420
aatgatgtca agcaaggtaa gcctcaccca gaaccatact taaagggtag aaacggtttg     480
ggtttcccaa ttaatgaaca agacccatcc aaatctaagg ttgttgtctt gaagacgca     540 ccagctggta ttgctgctgg taaggctgct ggctgtaaaa tcgttggtat tgctaccact     600
ttcgatttgg acttcttgaa ggaaaagggt tgtgacatca ttgtcaagaa ccacgaatct     660
atcagagtcg gtaatacaa cgctgaaacc gatgaagtcg aattgatctt tgatgactac     720
ttatacgcta aggatgactt gttgaaatgg taa                                 753

<210> SEQ ID NO 29
<211> LENGTH: 250
<212> TYPE: PRT
<213> ORGANISM: Saccharomyces cerevisiae

<400> SEQUENCE: 29

Met Pro Leu Thr Thr Lys Pro Leu Ser Leu Lys Ile Asn Ala Ala Leu
 1               5                  10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
```

```
                 50                  55                  60
Phe Ala Pro Asp Phe Ala Asp Glu Glu Tyr Val Asn Lys Leu Glu Gly
 65                  70                  75                  80

Glu Ile Pro Glu Lys Tyr Gly Glu His Ser Ile Glu Val Pro Gly Ala
                 85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
            115                 120                 125

Leu Lys Ile Lys Arg Pro Glu Tyr Phe Ile Thr Ala Asn Asp Val Lys
130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
            165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
            195                 200                 205

Lys Gly Cys Asp Ile Ile Val Lys Asn His Glu Ser Ile Arg Val Gly
210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 30
<211> LENGTH: 500
<212> TYPE: PRT
<213> ORGANISM: Saccharomyces cerevisiae

<400> SEQUENCE: 30

Met Thr Lys Leu His Phe Asp Thr Ala Glu Pro Val Lys Ile Thr Leu
 1               5                  10                  15

Pro Asn Gly Leu Thr Tyr Glu Gln Pro Thr Gly Leu Phe Ile Asn Asn
                 20                  25                  30

Lys Phe Met Lys Ala Gln Asp Gly Lys Thr Tyr Pro Val Glu Asp Pro
             35                  40                  45

Ser Thr Glu Asn Thr Val Cys Glu Val Ser Ser Ala Thr Thr Glu Asp
         50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
            115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
            165                 170                 175
```

```
Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 31
<211> LENGTH: 1503
<212> TYPE: DNA
<213> ORGANISM: Saccharomyces cerevisiae

<400> SEQUENCE: 31
atgactaagc tacactttga cactgctgaa ccagtcaaga tcacacttcc aaatggtttg      60
acatacgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttgaata tgctatcgaa tgtgccgacc gtgctttcca cgacactgaa     240
```

```
tgggctaccc aagacccaag agaaagaggc cgtctactaa gtaagttggc tgacgaattg      300
gaaagccaaa ttgacttggt ttcttccatt gaagctttgg acaatggtaa aactttggcc      360
ttagcccgtg gggatgttac cattgcaatc aactgtctaa gagatgctgc tgcctatgcc      420
gacaaagtca acggtagaac aatcaacacc ggtgacggct acatgaactt caccaccttg      480
gagccaatcg gtgtctgtgg tcaaattatt ccatggaact ttccaataat gatgttggct      540
tggaagatcg ccccagcatt ggccatgggt aacgtctgta tcttgaaacc cgctgctgtc      600
acacctttaa atgccctata ctttgcttct ttatgtaaga aggttggtat tccagctggt      660
gtcgtcaaca tcgttccagg tcctggtaga actgttggtg ctgctttgac caacgaccca      720
agaatcagaa agctggcttt taccggttct acagaagtcg gtaagagtgt tgctgtcgac      780
tcttctgaat ctaacttgaa gaaaatcact ttggaactag gtggtaagtc cgcccatttg      840
gtctttgacg atgctaacat taagaagact ttaccaaatc tagtaaacgg tattttcaag      900
aacgctggtc aaatttgttc ctctggttct agaatttacg ttcaagaagg tatttacgac      960
gaactattgg ctgctttcaa ggcttacttg gaaaccgaaa tcaaagttgg taatccatttt    1020 gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
gttaaggaag aaattttgg accagttgtc actgtcgcaa agttcaagac tttagaagaa    1260
ggtgtcgaaa tggctaacag ctctgaattc ggtctaggtt ctggtatcga aacagaatct    1320
ttgagcacag gtttgaaggt ggccaagatg ttgaaggccg gtaccgtctg gatcaacaca    1380
tacaacgatt ttgactccag agttccattc ggtggtgtta agcaatctgg ttacggtaga    1440
gaaatgggtg aagaagtcta ccatgcatac actgaagtaa aagctgtcag aattaagttg    1500
taa                                                                   1503
```

<210> SEQ ID NO 32
<211> LENGTH: 1404
<212> TYPE: DNA
<213> ORGANISM: Escherichia coli

<400> SEQUENCE: 32

```
atgaatcaac aggatattga acaggtggtg aaagcggtac tgctgaaaat gcaaagcagt       60
gacacgccgt ccgccgccgt tcatgagatg ggcgttttcg cgtccctgga tgacgccgtt     120
gcggcagcca agtcgcccca gcaagggtta aaaagcgtgg caatgcgcca gttagccatt     180
gctgccattc gtgaagcagg cgaaaaacac gccagagatt tagcggaact tgccgtcagt     240
gaaaccggca tggggcgcgt tgaagataaa tttgcaaaaa acgtcgctca ggcgcgcggc     300
acaccaggcg ttgagtgcct ctctccgcaa gtgctgactg cgacaacgg cctgacccta     360 attgaaaacg cacccctgggg cgtggtggct tcggtgacgc cttccactaa cccggcggca     420
accgtaatta acaacgccat cagcctgatt gccgcgggca cagcgtcat ttttgccccg     480 catccggcgg cgaaaaaagt ctcccagcgg gcgattacgc tgctcaacca ggcgattgtt     540
gccgcaggtg ggccggaaaa cttactggtt actgtgcaa atccggatat cgaaccgcg      600 caacgcttgt tcaagttccc gggtatcggc ctgctggtgg taaccggcgg cgaagcggta     660
gtagaagcgg cgcgtaaaca caccaataaa cgtctgattg ccgcaggcgc tggcaacccg     720
ccggtagtgg tggatgaaac cgccgacctc gcccgtgccg ctcagtccat cgtcaaaggc     780 gcttcttcg ataacaacat catttgtgcc gacgaaaagg tactgattgt tgttgatagc     840
```

-continued

```
gtagccgatg aactgatgcg tctgatggaa ggccagcacg cggtgaaact gaccgcagaa    900
caggcgcagc agctgcaacc ggtgttgctg aaaaatatcg acgagcgcgg aaaaggcacc    960
gtcagccgtg actgggttgg tcgcgacgca ggcaaaatcg cggcggcaat cggccttaaa   1020
gttccgcaag aaacgcgcct gctgtttgtg gaaaccaccg cagaacatcc gtttgccgtg   1080
actgaactga tgatgccggt gttgcccgtc gtgcgcgtcg ccaacgtggc ggatgccatt   1140
gcgctagcgg tgaaactgga aggcggttgc caccacacgg cggcaatgca ctcgcgcaac   1200
atcgaaaaca tgaaccagat ggcgaatgct attgatacca gcattttcgt taagaacgga   1260
ccgtgcattg ccgggctggg gctggcgggg aaggctgga  ccaccatgac catcaccacg   1320
ccaaccggtg aagggtaac  cagcgcgcgt acgtttgtcc gtctgcgtcg ctgtgtatta   1380
gtcgatgcgt ttcgcattgt ttaa                                          1404
```

<210> SEQ ID NO 33
<211> LENGTH: 467
<212> TYPE: PRT
<213> ORGANISM: Escherichia coli

<400> SEQUENCE: 33

```
Met Asn Gln Gln Asp Ile Glu Gln Val Val Lys Ala Val Leu Leu Lys
  1               5                  10                  15
Met Gln Ser Ser Asp Thr Pro Ser Ala Ala Val His Glu Met Gly Val
             20                  25                  30
Phe Ala Ser Leu Asp Asp Ala Val Ala Ala Lys Val Ala Gln Gln
         35                  40                  45
Gly Leu Lys Ser Val Ala Met Arg Gln Leu Ala Ile Ala Ala Ile Arg
     50                  55                  60
Glu Ala Gly Glu Lys His Ala Arg Asp Leu Ala Glu Leu Ala Val Ser
 65                  70                  75                  80
Glu Thr Gly Met Gly Arg Val Glu Asp Lys Phe Ala Lys Asn Val Ala
                 85                  90                  95
Gln Ala Arg Gly Thr Pro Gly Val Glu Cys Leu Ser Pro Gln Val Leu
            100                 105                 110
Thr Gly Asp Asn Gly Leu Thr Leu Ile Glu Asn Ala Pro Trp Gly Val
        115                 120                 125
Val Ala Ser Val Thr Pro Ser Thr Asn Pro Ala Ala Thr Val Ile Asn
    130                 135                 140
Asn Ala Ile Ser Leu Ile Ala Ala Gly Asn Ser Val Ile Phe Ala Pro
145                 150                 155                 160
His Pro Ala Ala Lys Lys Val Ser Gln Arg Ala Ile Thr Leu Leu Asn
                165                 170                 175
Gln Ala Ile Val Ala Ala Gly Gly Pro Glu Asn Leu Leu Val Thr Val
            180                 185                 190
Ala Asn Pro Asp Ile Glu Thr Ala Gln Arg Leu Phe Lys Phe Pro Gly
        195                 200                 205
Ile Gly Leu Leu Val Val Thr Gly Gly Glu Ala Val Val Glu Ala Ala
    210                 215                 220
Arg Lys His Thr Asn Lys Arg Leu Ile Ala Ala Gly Ala Gly Asn Pro
225                 230                 235                 240
Pro Val Val Val Asp Glu Thr Ala Asp Leu Ala Arg Ala Ala Gln Ser
                245                 250                 255
Ile Val Lys Gly Ala Ser Phe Asp Asn Asn Ile Ile Cys Ala Asp Glu
            260                 265                 270
```

-continued

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 34
<211> LENGTH: 316
<212> TYPE: PRT
<213> ORGANISM: Escherichia coli

<400> SEQUENCE: 34

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
                20                  25                  30

Val Met Val Gly Ile Asp Pro Gln Ser Asp Gly Leu Ala Arg Ala Arg
            35                  40                  45

Arg Met Gly Val Ala Thr Thr His Glu Gly Val Ile Gly Leu Met Asn
        50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu

```
                165                 170                 175
Thr Thr Ser Arg Ala Ile Glu Val Val Gly Ala Ala Lys Gly Lys
            180                 185                 190

Ala Ile Ile Val Leu Asn Pro Ala Glu Pro Pro Leu Met Met Arg Asp
            195                 200                 205

Thr Val Tyr Val Leu Ser Asp Glu Ala Ser Gln Asp Asp Ile Glu Ala
        210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
        290                 295                 300

Ala Gln Ser Leu Ala Arg Lys Ala Gly Glu Ala Ala
305                 310                 315

<210> SEQ ID NO 35
<211> LENGTH: 951
<212> TYPE: DNA
<213> ORGANISM: Escherichia coli

<400> SEQUENCE: 35
atgagtaagc gtaaagtcgc cattatcggt tctggcaaca ttggtaccga tctgatgatt      60
aaaattttgc gtcacggtca gcatctggag atggcggtga tggttggcat tgatcctcag     120
tccgacggtc tggcgcgcgc cagacgtatg ggcgtcgcca ccacccatga aggggtgatc     180
ggactgatga acatgcctga atttgctgat atcgacattg tatttgatgc gaccagcgcc     240
ggtgctcatg tgaaaaacga tgccgcttta cgcgaagcga aaccggatat cgcttaatt      300 gacctgacgc ctgctgccat cggcccttac tgcgtgccgg tggttaacct cgaggcgaac     360
gtcgatcaac tgaacgtcaa catggtcacc tgcgcggcc aggccaccat tccaatggtg     420
gcggcagttt cacgcgtggc gcgtgttcat tacgccgaaa ttatcgcttc tatcgccagt     480
aaatctgccg gacctggcac gcgtgccaat atcgatgaat tacgaaaac cacttcccga     540 gccattgaag tggtgggcgg cgcggcaaaa gggaaggcga ttattgtgct taacccagca     600
gagccaccgt tgatgatgcg tgacacggtg tatgtattga gcgacgaagc ttcacaagat     660
gatatcgaag cctcaatcaa tgaaatggct gaggcggtgc aggcttacgt accgggttat     720
cgcctgaaac agcgcgtgca gtttgaagtt atcccgcagg ataaaccggt caatttaccg     780
ggcgtggggc aattctccgg actgaaaaca gcggtctggc tggaagtcga aggcgcagcg     840
cattatctgc ctgcctatgc gggcaacctc gacattatga cttccagtgc gctggcgaca     900
gcggaaaaaa tggcccagtc actggcgcgc aaggcaggag aagcggcatg a              951

<210> SEQ ID NO 36
<211> LENGTH: 954
<212> TYPE: DNA
<213> ORGANISM: Artificial Sequence
<220> FEATURE:
<223> OTHER INFORMATION: Synthetic Saccharomyces cerevisiae codon
      optimized mhpF gene

<400> SEQUENCE: 36
```

```
atgtcaaagc gaaaagtagc tatcataggt tcaggtaata ttggtactga tttgatgatc      60
aaaatcctga gacatggcca gcacttggag atggccgtca tggttggtat cgacccacaa     120
tccgatggct tagctagagc taggagaatg ggtgttgcca caactcacga agggttatt     180 ggcttaatga acatgccaga atttgcagac atcgatatag tttttgatgc tactagtgca     240
ggggcacatg tgaaaaacga cgcggcttta agagaagcca agccagatat tagattaatt     300
gatcttaccc ctgctgctat aggtccttac tgcgttcctg tagttaacct tgaagctaat     360
gtggaccagt tgaacgtgaa tatggttaca tgtggtggcc aagctaccat accaatggtt     420
gctgctgtct ctagagtggc cagagtacat tatgccgaga tcattgcgtc tatcgcatct     480
aagtctgccg gtcctggaac aagggctaac atcgatgagt tcactgagac aacctctaga     540
gctatcgaag tagtaggagg cgcagcaaaa ggtaaagcga tcattgtttt gaatcctgcc     600
gaaccacctt tgatgatgag agatacggtc tacgtgctat cagatgaagc ttcccaggat     660
gacattgaag ctagcattaa tgagatggca gaagccgttc aagcatacgt gccaggatat     720
agactcaaac aaagagtcca atttgaggtc attccacaag acaagccagt taatctccca     780
ggggtcggtc aattctcagg actaaaaact gctgtttggt tagaagtaga aggagctgct     840
cattacctac cagcctacgc cggtaatttg gatataatga catcttccgc tcttgcaaca     900
gcagaaaaga tggcacaaag tctggcccgt aaggcaggag aagcggcata ataa           954
```

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
cgagctcttc gcggccacct acgccgctat c                                     31

<210> SEQ ID NO 38
<211> LENGTH: 32
<212> TYPE: DNA
<213> ORGANISM: Artificial Sequence
<220> FEATURE:
<223> OTHER INFORMATION: primer

<400> SEQUENCE: 38
gctctagata ttgatatagt gtttaagcga at                                    32

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
cggccatggc gggagctcgc atgcaag                                          27

<210> SEQ ID NO 40
<211> LENGTH: 28
<212> TYPE: DNA
<213> ORGANISM: Artificial Sequence
<220> FEATURE:
<223> OTHER INFORMATION: primer

<400> SEQUENCE: 40
cgggatatca ctagtgagct cgctccgc                                            28

<210> SEQ ID NO 41
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 41
gccgggagag ctcgcatgca agtaacctat tcaaagtaat atctcataca tgtttcatga      60
gggtaacaac atgcgactgg gtgagcatat gttccgctga tgtgatgtgc aagataaaca     120
agcaaggcag aaactaactt cttcttcatg taataaacac ccccgcgtt tatttaccta      180
tctctaaact tcaacacctt atatcataac taatatttct tgagataagc acactgcacc    240
cataccttcc ttaaaaacgt agcttccagt ttttggtggt tccggcttcc ttcccgattc    300
cgcccgctaa acgcatattt tgttgcctg gtggcatttg caaaatgcat aacctatgca    360
tttaaaagat tatgtatgct cttctgactt ttcgtgtgat gaggctcgtg gaaaaaatga    420
ataatttatg aatttgagaa caattttgtg ttgttacggt attttactat ggaataatca    480
atcaattgag gattttatgc aaatatcgtt tgaatatttt tccgaccctt tgagtacttt    540
tcttcataat tgcataatat tgtccgctgc ccctttttct gttagacggt gtcttgatct    600
acttgctatc gttcaacacc acctattttt ctaactattt tttttttagc tcatttgaat    660
cagcttatgg tgatggcaca ttttttgcata aacctagctg tcctcgttga acataggaaa    720
aaaaaatata taaacaaggc tctttcactc tccttgcaat cagatttggg tttgttccct    780
ttatttcat atttcttgtc atattccttt ctcaattatt attttctact cataacctca    840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa  1020
tagctgcgcc gatggtttct acaaagatcg ttatgtttat cggcactttg catcggccgc  1080
gctcccgatt ccggaagtgc ttgacattgg ggaattcagc gagagcctga cctattgcat  1140
ctcccgccgt gcacagggtg tcacgttgca agacctgcct gaaaccgaac tgcccgctgt  1200
tctgcagccg gtcgcggagg ccatggatgc gatcgctgcg gccgatctta gccagacgag  1260
cgggttcggc ccattcggac cgcaaggaat cggtcaatac actacatggc gtgatttcat  1320
atgcgcgatt gctgatcccc atgtgtatca ctggcaaact gtgatggacg acaccgtcag  1380
tgcgtccgtc gcgcaggctc tcgatgagct gatgctttgg gccgaggact gccccgaagt  1440
ccggcacctc gtgcacgcgg atttcggctc caacaatgtc ctgacggaca atggccgcat  1500
aacagcggtc attgactgga gcgaggcgat gttcggggat tcccaatacg aggtcgccaa  1560
catcttcttc tggaggccgt ggttggcttg tatggagcag cagacgcgct acttcgagcg  1620
gaggcatccg gagcttgcag atcgccgcg gctccgggcg tatatgctcc gcattggtct  1680
tgaccaactc tatcagagct tggttgacgg caatttcgat gatgcagctt gggcgcaggg  1740
tcgatgcgac gcaatcgtcc gatcggagc cgggactgtc gggcgtacac aaatcgcccg  1800
cagaagcgcg gccgtctgga ccgatggctg tgtagaagta ctcgccgata gtggaaaccg  1860
acgccccagc actcgtccgg atcgggagat ggggaggct aactgaggat ccgtagatac  1920
attgatgcta tcaatcaaga gaactggaaa gattgtgtaa ccttgaaaaa cggtgaaact  1980
tacgggtcca agattgtcta cagattttcc tgatttgcca gcttactatc cttcttgaaa  2040

| | |
|---|---|
| atatgcactc tatatctttt agttcttaat tgcaacacat agatttgctg tataacgaat | 2100 |
| tttatgctat tttttaaatt tggagttcag tgataaaagt gtcacagcga atttcctcac | 2160 |
| atgtagggac cgaattgttt acaagttctc tgtaccacca tggagacatc aaaaattgaa | 2220 |
| aatctatgga agatatgga cggtagcaac aagaatatag cacgagccgc ggagcgagct | 2280 |
| cggccgcact agtgatatcc cgcggccatg gcggccggga g | 2321 |

<210> SEQ ID NO 42
<211> LENGTH: 75
<212> TYPE: DNA
<213> ORGANISM: Artificial Sequence
<220> FEATURE:
<223> OTHER INFORMATION: primer

<400> SEQUENCE: 42

| | |
|---|---|
| acaatatttc aagctatacc aagcatacaa tcaactatct catatacaat gggccgcaaa | 60 |
| ttaaagcctt cgagc | 75 |

<210> SEQ ID NO 43
<211> LENGTH: 75
<212> TYPE: DNA
<213> ORGANISM: Artificial Sequence
<220> FEATURE:
<223> OTHER INFORMATION: primer

<400> SEQUENCE: 43

| | |
|---|---|
| aatcataaga aattcgctta tttagaagtg tcaacaacgt atctaccaac gactaaaggg | 60 |
| aacaaaagct ggagc | 75 |

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44

| | |
|---|---|
| gaaacagcta tgaccatg | 18 |

<210> SEQ ID NO 45
<211> LENGTH: 32
<212> TYPE: DNA
<213> ORGANISM: Artificial Sequence
<220> FEATURE:
<223> OTHER INFORMATION: primer

<400> SEQUENCE: 45

| | |
|---|---|
| gacatgacga gctcgaattg ggtaccggcc gc | 32 |

<210> SEQ ID NO 46
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 46

| | |
|---|---|
| gatgacggtg aaaacctctg acacatgcag ctcccggaga cggtcacagc ttgtctgtaa | 60 |
| gcggatgccg ggagcagaca agcccgtcag gcgcgtcag cgggtgttgg cgggtgtcgg | 120 |
| ggctggctta actatgcggc atcagagcag attgtactga gagtgcacca tatgcggtgt | 180 |

```
gaaataccgc acagatgcgt aaggagaaaa taccgcatca ggcgccattc gccattcagg    240
ctgcgcaact gttgggaagg gcgatcggtg cgggcctctt cgctattacg ccagctggcg    300 aaaggggggat gtgctgcaag gcgattaagt tgggtaacgc cagggttttc ccagtcacga   360
cgttgtaaaa cgacggccag tgaattcgag ctcggtacct cgcgaatgca tctagatatc    420
ggatcccgac gagctgcacc gcggtggcgg ccgtatcttt acccatacg atgttcctga    480 ctatgcgggc tatccctatg acgtcccgga ctatgcagga tcctatccat atgacgttcc    540
agattacgct gctcagtgcg gccgcctgag agtgcaccat accacagctt tcaattcaa    600 ttcatcattt ttttttttatt cttttttttg atttcggttt ctttgaaatt ttttgattc    660 ggtaatctcc gaacagaagg aagaacgaag gaaggagcac agacttagat tggtatatat    720
acgcatatgt agtgttgaag aaacatgaaa ttgcccagta ttcttaaccc aactgcacag    780
aacaaaaacc tgcaggaaac gaagataaat catgtcgaaa gctacatata aggaacgtgc    840
tgctactcat cctagtcctg ttgctgccaa gctatttaat atcatgcacg aaaagcaaac    900
aaacttgtgt gcttcattgg atgttcgtac caccaaggaa ttactggagt tagttgaagc    960
attaggtccc aaaatttgtt tactaaaaac acatgtggat atcttgactg attttttccat   1020 ggagggcaca gttaagccgc taaaggcatt atccgccaag tacaattttt tactcttcga    1080
agacagaaaa tttgctgaca ttggtaatac agtcaaattg cagtactctg cgggtgtata    1140
cagaatagca gaatgggcag acattacgaa tgcacacggt gtggtgggcc caggtattgt    1200
tagcggtttg aagcaggcgg cagaagaagt aacaaaggaa cctagaggcc ttttgatgtt    1260
agcagaattg tcatgcaagg gctccctatc tactggagaa tatactaagg gtactgttga    1320
cattgcgaag agcgacaaag attttgttat cggctttatt gctcaaagag acatgggtgg    1380
aagagatgaa ggttacgatt ggttgattat gacacccggt gtgggtttag atgacaaggg    1440
agacgcattg ggtcaacagt atagaaccgt ggatgatgtg gtctctacag atctgacat     1500 tattattgtt ggaagaggac tatttgcaaa gggaagggat gctaaggtag agggtgaacg    1560
ttacagaaaa gcaggctggg aagcatattt gagaagatgc ggccagcaaa actaaaaaac    1620
tgtattataa gtaaatgcat gtatactaaa ctcacaaatt agagcttcaa tttaattata    1680
tcagttatta ccctatgcgg tgtgaaatac cgcacagatg cgtaaggaga aataccgca    1740 tcaggaaatt gtagcggccg cgaatttgag cttatctttt acccatacga tgttcctgac    1800
tatgcgggct atccctatga cgtcccggac tatgcaggat cctatccata tgacgttcca    1860
gattacgcta ctagcggggg gcccggtgac gggcccgtcg actgcagagg cctgcatgca    1920
agcttggcgt aatcatggtc atagctgttt cctgtgtgaa attgttatcc gctcacaatt    1980
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg gggagaggcg gtttgcgtat tgggcgctct    2160
tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata agataccagg cgtttcccc ctggaagctc cctcgtgcgc    2460
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
```

```
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc ccaacgatca    3480
aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
ctcttccttt ttcaatatta ttgaagcatt tatcagggtt attgtctcat gagcggatac    4020
atatttgaat gtatttagaa aaataaacaa ataggggttc cgcgcacatt tccccgaaaa    4080
gtgccacctg acgtctaaga aaccattatt atcatgacat taacctataa aaataggcgt    4140
atcacgaggc cctttcgtct cgcgcgtttc ggt                                 4173
```

<210> SEQ ID NO 47
<211> LENGTH: 62
<212> TYPE: DNA
<213> ORGANISM: Artificial Sequence
<220> FEATURE:
<223> OTHER INFORMATION: primer

<400> SEQUENCE: 47

```
gcttataaaa ctttaactaa taattagaga ttaaatcgct taaggtttcc cgactggaaa    60
gc                                                                    62
```

<210> SEQ ID NO 48
<211> LENGTH: 64
<212> TYPE: DNA
<213> ORGANISM: Artificial Sequence
<220> FEATURE:
<223> OTHER INFORMATION: primer

<400> SEQUENCE: 48

```
ctactcataa cctcacgcaa aataacacag tcaaatcaat caaaccagtc acgacgttgt    60
aaaa                                                               64

<210> SEQ ID NO 49
<211> LENGTH: 65
<212> TYPE: DNA
<213> ORGANISM: Artificial Sequence
<220> FEATURE:
<223> OTHER INFORMATION: primer

<400> SEQUENCE: 49
ccgaaatgat tccctttcct gcacaacacg agatctttca cgcatccagt cacgacgttg    60
taaaa                                                              65

<210> SEQ ID NO 50
<211> LENGTH: 65
<212> TYPE: DNA
<213> ORGANISM: Artificial Sequence
<220> FEATURE:
<223> OTHER INFORMATION: primer

<400> SEQUENCE: 50
aaagtagcct taaagctagg ctataatcat gcatcctcaa attctaggtt tcccgactgg    60
aaagc                                                              65

<210> SEQ ID NO 51
<211> LENGTH: 70
<212> TYPE: DNA
<213> ORGANISM: Artificial Sequence
<220> FEATURE:
<223> OTHER INFORMATION: primer

<400> SEQUENCE: 51
ccctatgtct ctggccgatc acgcgccatt gtccctcaga acaaatcaa ccagtcacga    60 cgttgtaaaa                                                         70

<210> SEQ ID NO 52
<211> LENGTH: 70
<212> TYPE: DNA
<213> ORGANISM: Artificial Sequence
<220> FEATURE:
<223> OTHER INFORMATION: primer

<400> SEQUENCE: 52
tagaagcaac tgtgccgaca gcctctgaat gagtggtgtt gtaaccaccc aggtttcccg    60
actggaaagc                                                         70

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ggacgtaaag ggtagcctcc                                              20

<210> SEQ ID NO 54
<211> LENGTH: 22
<212> TYPE: DNA
<213> ORGANISM: Artificial Sequence
<220> FEATURE:
<223> OTHER INFORMATION: primer
```

```
<400> SEQUENCE: 54
gaagcggacc cagacttaag cc                                              22

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
cgcaagaacg tagtatccac atgcc                                           25

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
ggatatttac agaacgatgc g                                               21

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcaatgagac tgttgtcctc ctact                                           25

<210> SEQ ID NO 58
<211> LENGTH: 24
<212> TYPE: DNA
<213> ORGANISM: Artificial Sequence
<220> FEATURE:
<223> OTHER INFORMATION: primer

<400> SEQUENCE: 58
tacatccttg tcgagccttg ggca                                            24

<210> SEQ ID NO 59
<211> LENGTH: 5999
<212> TYPE: DNA
<213> ORGANISM: Artificial Sequence
<220> FEATURE:
<223> OTHER INFORMATION: Synthetic pJ1214-mhpF vector

<400> SEQUENCE: 59
atgcagctca gattctttgt ttgaaaaatt agcgctctcg cgttgcattt ttgttttaca     60
aaaatgaagc acagattctt cgttggtaaa atagcgcttt cgcgttgcat ttctgttctg    120
taaaaatgca gctcagattc tttgtttgaa aaattagcgc tctcgcgttg cattttttgtt  180 ctacaaaatg aagcacagat gcttcgttca ggtggcactt tcggggaaa tgtgcgcgga    240 accctatttt gtttatttt  ctaaatacat tcaaatatgt atccgctcat gagacaataa    300
ccctgatatt ggtcagaatt ggttaattgg ttgtaacact gaccctatt tgtttatttt    360 tctaaataca ttcaaatatg tatccgctca tgagacaata accctgataa atgcttcaat    420
aatattgaaa aaggaagaat atgagtattc aacatttccg tgtcgccctt attcccttt    480
```

```
ttgcggcatt ttgccttcct gtttttgctc acccagaaac gctggtgaaa gtaaaagatg    540
ctgaagatca gttgggtgca cgagtgggtt acatcgaact ggatctcaac agcggtaaga    600
tccttgagag ttttcgcccc gaagaacgtt ttccaatgat gagcactttt aaagttctgc    660
tatgtggcgc ggtattatcc cgtattgacg ccgggcaaga gcaactcggt cgccgcatac    720
actattctca gaatgacttg gttgagtact caccagtcac agaaaagcat cttacggatg    780
gcatgacagt aagagaatta tgcagtgctg ccataaccat gagtgataac actgcggcca    840
acttacttct gacaacgatc ggaggaccga aggagctaac cgcttttttg cacaacatgg    900
gggatcatgt aactcgcctt gatcgttggg aaccggagct gaatgaagcc ataccaaacg    960
acgagcgtga caccacgatg cctgtagcga tggcaacaac gttgcgcaaa ctattaactg   1020
gcgaactact tactctagct tcccggcaac aattaataga ctggatggag gcggataaag   1080
ttgcaggacc acttctgcgc tcggcccttc cggctggctg gtttattgct gataaatccg   1140
gagccggtga gcgtggttct cgcggtatca tcgcagcgct ggggccagat ggtaagccct   1200
cccgtatcgt agttatctac acgacgggga gtcaggcaac tatggatgaa cgaaatagac   1260
agatcgctga gataggtgcc tcactgatta agcattggta actcatgacc aaaatccctt   1320
aacgtgagtt acgcgcgcgt cgttccactg agcgtcagac cccgtagaaa agatcaaagg   1380
atcttcttga tccttttttt ttctgcgcgt aatctgctgc ttgcaaacaa aaaaaccacc   1440
gctaccagcg gtggtttgtt tgccggatca agagctacca actcttttc cgaaggtaac   1500 tggcttcagc agagcgcaga taccaaatac tgttcttcta gtgtagccgt agttagccca   1560
ccacttcaag aactctgtag caccgcctac atacctcgct ctgctaatcc tgttaccagt   1620
ggctgctgcc agtggcgata agtcgtgtct taccgggttg gactcaagac gatagttacc   1680
ggataaggcg cagcggtcgg gctgaacggg gggttcgtgc acacagccca gcttggagcg   1740
aacgacctac accgaactga tacctacag cgtgagcta tgagaaagcg ccacgcttcc   1800
cgaagggaga aaggcggaca ggtatccggt aagcggcagg gtcggaacag gagagcgcac   1860
gagggagctt ccagggggaa acgcctggta tctttatagt cctgtcgggt ttcgccacct   1920
ctgacttgag cgtcgatttt tgtgatgctc gtcaggggg cggagcctat ggaaaaacgc   1980
cagcaacgcg gccttttac ggttcctggc cttttgctgg ccttttgctc acatgttctt   2040
tcctgcgtta tccctgatt ctgtggataa ccgtattacc gcctttgagt gagctgatac   2100 cgctcgggt cgtgcaggta tagcttcaaa atgtttctac tcctttttta ctcttccaga   2160
ttttctcgga ctccgcgcat cgccgtacca cttcaaaaca cccaagcaca gcatactaaa   2220 tttccctct ttcttcctct agggtgtcgt taattacccg tactaaaggt ttggaaaaga   2280
aaaaagtgac cgcctcgttt cttttcttc gtcgaaaaag gcaataaaaa tttttatcac   2340
gtttcttttt cttgaaaatt ttttttttg atttttttct ctttcgatga cctcccattg   2400
atatttaagt taataaacgg acttcaattt ctcaagtttc agtttcattt ttcttgttct   2460
attacaactt tttttacttc ttgctcatta gaaagaaagc atagcaatct aatctaagtt   2520
taaaatgtca aagcgaaaag tagctatcat aggttcaggt aatattggta ctgatttgat   2580
gatcaaaatc ctgagacatg gccagcactt ggagatggcc gtcatggttg gtatcgaccc   2640
acaatccgat ggcttagcta gagctaggag aatgggtgtt gccacaactc acgaagggt   2700 tattggctta atgaacatgc cagaatttgc agacatcgat atagttttg atgctactag   2760 tgcagggca catgtgaaaa acgacgcggc tttaagagaa gccaagccag atattagatt   2820
aattgatctt accctgctg ctataggtcc ttactgcgtt cctgtagtta accttgaagc   2880
```

```
taatgtggac cagttgaacg tgaatatggt tacatgtggt ggccaagcta ccataccaat    2940
ggttgctgct gtctctagag tggccagagt acattatgcc gagatcattg cgtctatcgc    3000
atctaagtct gccggtcctg aacaagggc taacatcgat gagttcactg agacaacctc    3060
tagagctatc gaagtagtag gaggcgcagc aaaaggtaaa gcgatcattg ttttgaatcc    3120
tgccgaacca cctttgatga tgagagatac ggtctacgtg ctatcagatg aagcttccca    3180
ggatgacatt gaagctagca ttaatgagat ggcagaagcc gttcaagcat acgtgccagg    3240
atatagactc aaacaaagag tccaatttga ggtcattcca caagacaagc cagttaatct    3300
cccaggggtc ggtcaattct caggactaaa aactgctgtt tggttagaag tagaaggagc    3360
tgctcattac ctaccagcct acgccggtaa tttggatata atgacatctt ccgctcttgc    3420
aacagcagaa aagatggcac aaagtctggc ccgtaaggca ggagaagcgg cataataaat    3480
catgtaatta gttatgtcac gcttacattc acgccctccc cccacatccg ctctaaccga    3540
aaaggaagga gttagacaac ctgaagtcta ggtccctatt tatttttta tagttatgtt     3600 agtattaaga acgttattta tatttcaaat ttttcttttt tttctgtaca gacgcgtgta    3660
cgcatgtaac attatactga aaaccttgct tgagaaggtt ttgggacgct cgaaggcttt    3720
aatttgcggc ccctcacctg cacgcaaaaa gcttttcaat tcaattcatc attttttttt    3780
tattcttttt tttgatttcg gtttctttga aattttttg attcggtaat ctccgaacag    3840
aaggaagaac gaaggaagga gcacagactt agattggtat atatacgcat atgtagtgtt    3900
gaagaaacat gaaattgccc agtattctta acccaactgc acagaacaaa accagcagg    3960 aaacgaagat aaatcatgtc gaaagctaca tataaggaac gtgctgctac tcatcctagt    4020
cctgttgctg ccaagctatt taatatcatg cacgaaaagc aaacaaactt gtgtgcttca    4080
ttggatgttc gtaccaccaa ggaattactg gagttagttg aagcattagg tcccaaaatt    4140 tgttactaa aaacacatgt ggatatcttg actgattttt ccatggaggg cacagttaag    4200
ccgctaaagg cattatccgc caagtacaat ttttactct tcgaagatag aaaatttgct    4260
gacattggta atacagtcaa attgcagtac tctgcgggtg tatacagaat agcagaatgg    4320
gcagacatta cgaatgcaca cggtgtggtg ggcccaggta ttgttagcgg tttgaagcag    4380
gcggcagaag aagtaacaaa ggaacctaga ggccttttga tgttagcaga attgtcatgc    4440
aagggctccc tatctactgg agaatatact aagggtactg ttgacattgc gaaaagcgac    4500
aaagattttg ttatcggctt tattgctcaa agagacatgg gtggaagaga tgaaggttac    4560
gattggttga ttatgacacc cggtgtgggt ttagatgaca agggagatgc attgggtcaa    4620
cagtatagaa ccgtggatga tgttgtctct acaggatctg acattattat tgttggaaga    4680
ggactatttg caagggaag ggatgctaag gtagagggtg aacgttacag aaaagcaggc    4740
tgggaagcat atttgagaag atgcggccag caaaactaaa aaactgtatt ataagtaaat    4800
gcatgtatac taaactcaca aattagagct tcaatttaat tatatcagtt attcccacg    4860 ctatgatcca atatcaaagg aaatgatagc attgaaggat gagactaatc caattgagga    4920
gtggcagcat atagaacagc taaagggtag tgctgaagga agcatacgat accccgcatg    4980
gaatgggata atatcacagg aggtactaga ctacctttca tcctacataa atagacgcat    5040
ataagtacgc atttaagcat aaacacgcac tatgccgttc ttctcatgta tatatatata    5100
caggcaacac gcagatatag gtgcgacgtg aacagtgagc tgtatgtgcg cagctcgcgt    5160 tgcatttcg gaagcgctcg ttttcggaaa cgctttgaag ttcctattcc gaagttccta    5220
```

| | |
|---|---|
| ttctctagaa agtataggaa cttcagagcg cttttgaaaa ccaaaagcgc tctgaagtcg | 5280 |
| cactttcaaa aaaccaaaaa cgcaccggac tgtaacgagc tactaaaata ttgcgaatac | 5340 |
| cgcttccaca aacattgctc aaaagtatct ctttgctata tatctctgtg ctatatccct | 5400 |
| atataaccta cccatccacc tttcgctcct gaacttgca tctaaactcg acctctacat | 5460 |
| tttttatgtt tatctctagt attactcttt agacaaaaaa attgtagtaa gaactattca | 5520 |
| tagagtgaat cgaaacaat acgaaaatgt aaacatttcc tatacgtagt atatagagac | 5580 |
| aaaatagaag aaaccgttca taattttctg accaatgaag aatcatcaac gctatcactt | 5640 |
| tctgttcaca agtatgcgc aatccacatc ggtatagaat ataatcgggg atgcctttat | 5700 |
| cttgaaaaaa tgcacccgca gcttcgctag taatcagtaa acgcgggaag tggagtcagg | 5760 |
| cttttttat ggaagagaaa atagacacca aagtagcctt cttctaacct taacggacct | 5820 |
| acagtgcaaa aagttatcaa gagactgcat tatagagcgc acaaggaga aaaaaagtaa | 5880 |
| tctaagatgc tttgttagaa aaatagcgct ctcgggatgc attttttgtag aacaaaaaag | 5940 |
| aagtatagat tctttgttgg taaaatagcg ctctcgcgtt gcatttctgt tctgtaaaa | 5999 |

<210> SEQ ID NO 60
<211> LENGTH: 5779
<212> TYPE: DNA
<213> ORGANISM: Artificial Sequence
<220> FEATURE:
<223> OTHER INFORMATION: Synthetic pUC19-His-MhpF

<400> SEQUENCE: 60

| | |
|---|---|
| tcgacctgca ggcatgcaag cttggcgtaa tcatggtcat agctgtttcc tgtgtgaaat | 60 |
| tgttatccgc tcacaattcc acacaacata cgagccggaa gcataaagtg taaagcctgg | 120 |
| ggtgcctaat gagtgagcta actcacatta attgcgttgc gctcactgcc cgctttccag | 180 |
| tcgggaaacc tgtcgtgcca gctgcattaa tgaatcggcc aacgcgcggg gagaggcggt | 240 |
| ttgcgtattg ggcgctcttc cgcttcctcg ctcactgact cgctgcgctc ggtcgttcgg | 300 |
| ctgcggcgag cggtatcagc tcactcaaag gcggtaatac ggttatccac agaatcaggg | 360 |
| gataacgcag gaaagaacat gtgagcaaaa ggccagcaaa aggccaggaa ccgtaaaaag | 420 |
| gccgcgttgc tggcgttttt ccataggctc cgcccccctg acgagcatca caaaaatcga | 480 |
| cgctcaagtc agaggtggcg aaacccgaca ggactataaa gataccaggc gtttccccct | 540 |
| ggaagctccc tcgtgcgctc tcctgttccg accctgccgc ttaccggata cctgtccgcc | 600 |
| tttctccctt cgggaagcgt ggcgctttct catagctcac gctgtaggta tctcagttcg | 660 |
| gtgtaggtcg ttcgctccaa gctgggctgt gtgcacgaac cccccgttca gcccgaccgc | 720 |
| tgcgccttat ccggtaacta tcgtcttgag tccaacccgg taagacacga cttatcgcca | 780 |
| ctggcagcag ccactggtaa caggattagc agagcgaggt atgtaggcgg tgctacagag | 840 |
| ttcttgaagt ggtggcctaa ctacggctac actagaagaa cagtatttgg tatctgcgct | 900 |
| ctgctgaagc cagttacctt cggaaaaaga gttggtagct cttgatccgg caaacaaacc | 960 |
| accgctggta gcggtggttt ttttgtttgc aagcagcaga ttacgcgcag aaaaaaagga | 1020 |
| tctcaagaag atcctttgat cttttctacg ggtctgacg ctcagtggaa cgaaaactca | 1080 |
| cgttaaggga ttttggtcat gagattatca aaaaggatct tcacctagat ccttttaaat | 1140 |
| taaaaatgaa gttttaaatc aatctaaagt atatatgagt aaacttggtc tgacagttac | 1200 |
| caatgcttaa tcagtgaggc acctatctca gcgatctgtc tatttcgttc atccatagtt | 1260 |
| gcctgactcc ccgtcgtgta gataactacg atacgggagg gcttaccatc tggccccagt | 1320 |

```
gctgcaatga taccgcgaga cccacgctca ccggctccag atttatcagc aataaaccag   1380
ccagccggaa gggccgagcg cagaagtggt cctgcaactt tatccgcctc catccagtct   1440
attaattgtt gccgggaagc tagagtaagt agttcgccag ttaatagttt gcgcaacgtt   1500
gttgccattg ctacaggcat cgtggtgtca cgctcgtcgt ttggtatggc ttcattcagc   1560
tccggttccc aacgatcaag gcgagttaca tgatccccca tgttgtgcaa aaaagcggtt   1620
agctccttcg gtcctccgat cgttgtcaga agtaagttgg ccgcagtgtt atcactcatg   1680
gttatggcag cactgcataa ttctcttact gtcatgccat ccgtaagatg cttttctgtg   1740
actggtgagt actcaaccaa gtcattctga aatagtgta tgcggcgacc gagttgctct    1800
tgcccggcgt caatacggga ataccgcg ccacatagca aactttaaa agtgctcatc      1860 attggaaaac gttcttcggg gcgaaaactc tcaaggatct taccgctgtt gagatccagt   1920
tcgatgtaac ccactcgtgc acccaactga tcttcagcat cttttacttt caccagcgtt   1980
tctgggtgag caaaaacagg aaggcaaaat gccgcaaaaa agggaataag ggcgacacgg   2040
aaatgttgaa tactcatact cttccttttt caatattatt gaagcattta tcagggttat   2100
tgtctcatga gcggatacat atttgaatgt atttagaaaa ataaacaaat aggggttccg   2160
cgcacatttc cccgaaaagt gccacctgac gtctaagaaa ccattattat catgacatta   2220
acctataaaa ataggcgtat cacgaggccc tttcgtctcg cgcgtttcgg tgatgacggt   2280
gaaaacctct gacacatgca gctcccggag acggtcacag cttgtctgta agcggatgcc   2340
gggagcagac aagcccgtca gggcgcgtca gcgggtgttg gcgggtgtcg gggctggctt   2400
aactatgcgg catcagagca gattgtactg agagtgcacc atatgcggtg tgaaataccg   2460
cacagatgcg taaggagaaa ataccgcatc aggcgccatt cgccattcag gctgcgcaac   2520
tgttgggaag ggcgatcggt gcgggcctct tcgctattac gccagctggc aaagggggga   2580
tgtgctgcaa ggcgattaag ttgggtaacg ccagggtttt cccagtcacg acgttgtaaa   2640
acgacggcca gtgaattcga gctcagttta tcattatcaa tactcgccat ttcaaagaat   2700
acgtaaataa ttaatagtag tgattttcct aactttattt agtcaaaaaa ttagcctttt   2760
aattctgctg taacccgtac atgcccaaaa taggggggcgg gttacacaga atatataaca   2820
tcgtaggtgt ctgggtgaac agtttattcc tggcatccac taaatataat ggagcccgct   2880
ttttaagctg catccagaa aaaaaagaa tcccagcacc aaaatattgt ttcttcacc      2940 aaccatcagt tcataggtcc attctcttag cgcaactaca gagaacaggg gcacaaacag   3000
gcaaaaaacg ggcacaacct caatggagtg atgcaacctg cctggagtaa atgatgacac   3060
aaggcaattg acccacgcat gtatctatct cattttctta caccttctat taccttctgc   3120
tctctctgat ttggaaaaag ctgaaaaaaa aggttgaaac cagttccctg aaattattcc   3180
cctacttgac taataagtat ataaagacgg taggtattga ttgtaattct gtaaatctat   3240
ttcttaaact tcttaaattc tacttttata gttagtcttt tttttagttt taaaacacca   3300
gaacttagtt tcgacggatt ctagaactag tggatccatg tcaaagcgaa aagtagctat   3360
cataggttca ggtaatattg gtactgattt gatgatcaaa atcctgagac atggccagca   3420
cttggagatg gccgtcatgg ttggtatcga cccacaatcc gatggcttag ctagagctag   3480
gagaatgggt gttgccacaa ctcacgaagg ggttattggc ttaatgaaca tgccagaatt   3540
tgcagacatc gatatagttt ttgatgctac tagtgcaggg gcacatgtga aaacgacgc    3600 ggctttaaga gaagccaagc cagatattag attaattgat cttacccctg ctgctatagg   3660
```

```
tccttactgc gttcctgtag ttaaccttga agctaatgtg gaccagttga acgtgaatat    3720
ggttacatgt ggtggccaag ctaccatacc aatggttgct gctgtctcta gagtggccag    3780
agtacattat gccgagatca ttgcgtctat cgcatctaag tctgccggtc ctggaacaag    3840
ggctaacatc gatgagttca ctgagacaac ctctagagct atcgaagtag taggaggcgc    3900
agcaaaaggt aaagcgatca ttgttttgaa tcctgccgaa ccacctttga tgatgagaga    3960
tacggtctac gtgctatcag atgaagcttc ccaggatgac attgaagcta gcattaatga    4020
gatggcagaa gccgttcaag catacgtgcc aggatataga ctcaaacaaa gagtccaatt    4080
tgaggtcatt ccacaagaca agccagttaa tctcccaggg gtcggtcaat tctcaggact    4140
aaaaactgct gtttggttag aagtagaagg agctgctcat tacctaccag cctacgccgg    4200
taatttggat ataatgacat cttccgctct tgcaacagca gaaagatggc acaaagtct    4260 ggcccgtaag gcaggagaag cggcataata atcctcgag tcatgtaatt agttatgtca    4320
cgcttacatt cacgccctcc ccccacatcc gctctaaccg aaaggaagg agttagacaa    4380 cctgaagtct aggtccctat ttatttttt atagttatgt tagtattaag aacgttattt    4440
atatttcaaa ttttttcttt ttttctgtac agacgcgtgt acgcatgtaa cattatactg    4500 aaaccttgc ttgagaaggt tttgggacgc tcgaaggctt taatttgcgg ccggtaccca    4560
attcgagctc ggtacccggg gatcctctag agtcgacaat tccgttttta agagcttggt    4620
gagcgctagg agtcactgcc aggtatcgtt tgaacacggc attagtcagg gaagtcataa    4680
cacagtcctt tcccgcaatt ttcttttct attactcttg gcctcctcta gtacactcta    4740
tattttttta tgcctcggta atgattttca tttttttttt tccctagcg gatgactctt    4800 tttttttctt agcgattggc attatcacat aatgaattat acattatata agtaatgtg    4860 atttcttcga agaatatact aaaaaatgag caggcaagat aaacgaaggc aaagatgaca    4920
gagcagaaag ccctagtaaa gcgtattaca aatgaaacca agattcagat tgcgatctct    4980
ttaaagggtg gtcccctagc gatagagcac tcgatcttcc cagaaaaaga ggcagaagca    5040
gtagcagaac aggccacaca atcgcaagtg attaacgtcc acacaggtat agggtttctg    5100
gaccatatga tacatgctct ggccaagcat tccggctggt cgctaatcgt tgagtgcatt    5160
ggtgacttac acatagacga ccatcacacc actgaagact gcgggattgc tctcggtcaa    5220
gcttttaaag aggccctact ggcgcgtgga gtaaaaaggt ttggatcagg atttgcgcct    5280
ttggatgagg cactttccag agcggtggta gatcttcga acaggccgta cgcagttgtc    5340
gaacttggtt tgcaaaggga gaaagtagga gatctctctt gcgagatgat cccgcattt    5400 cttgaaagct ttgcagaggc tagcagaatt accctccacg ttgattgtct gcgaggcaag    5460
aatgatcatc accgtagtga gagtgcgttc aaggctcttg cggttgccat aagagaagcc    5520
acctcgccca atggtaccaa cgatgttccc tccaccaaag gtgttcttat gtagtgacac    5580
cgattattta agctgcagc atacgatata tatacatgtg tatatatgta tacctatgaa    5640
tgtcagtaag tatgtatacg aacagtatga tactgaagat gacaaggtaa tgcatcattc    5700
tatacgtgtc attctgaacg aggcgcgctt tccttttttc ttttgctttt tctttttttt    5760
ttctcttgaa ctcgacggg                                                 5779
```

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
cctcctgagt cgacaattcc cgttttaaga g                                31

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
cgaccgtggt cgacccgtcg agttcaagag                                  30

<210> SEQ ID NO 63
<211> LENGTH: 67
<212> TYPE: DNA
<213> ORGANISM: Artificial Sequence
<220> FEATURE:
<223> OTHER INFORMATION: primer

<400> SEQUENCE: 63
tatatatttc aaggatatac cattctaatg tctgcccta agaagatcgt gctgcaaggc    60
gattaag                                                           67

<210> SEQ ID NO 64
<211> LENGTH: 67
<212> TYPE: DNA
<213> ORGANISM: Artificial Sequence
<220> FEATURE:
<223> OTHER INFORMATION: primer

<400> SEQUENCE: 64
gagaatcttt ttaagcaagg attttcttaa cttcttcggc gacagcatcg gctcgtatgt    60
tgtgtgg                                                           67

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
gtttcgtcta ccctatgaac                                             20

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
ccaataggtg gttagcaatc g                                           21

<210> SEQ ID NO 67
<211> LENGTH: 64
<212> TYPE: DNA
<213> ORGANISM: Artificial Sequence
<220> FEATURE:
<223> OTHER INFORMATION: primer

<400> SEQUENCE: 67

```
caagaaacat ctttaacata cacaaacaca tactatcaga atacccagtc acgacgttgt    60
aaaa                                                                64

<210> SEQ ID NO 68
<211> LENGTH: 65
<212> TYPE: DNA
<213> ORGANISM: Artificial Sequence
<220> FEATURE:
<223> OTHER INFORMATION: primer

<400> SEQUENCE: 68 gtatttgtg tatatgacgg aaagaaatgc aggttggtac attacaggtt tcccgactgg    60
aaagc                                                               65

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
gcatcgggaa cgtatgtaac attg                                          24

<210> SEQ ID NO 70
<211> LENGTH: 19
<212> TYPE: DNA
<213> ORGANISM: Artificial Sequence
<220> FEATURE:
<223> OTHER INFORMATION: primer

<400> SEQUENCE: 70
tgacgtaaga ccaagtaag                                                19

<210> SEQ ID NO 71
<211> LENGTH: 55
<212> TYPE: DNA
<213> ORGANISM: Artificial Sequence
<220> FEATURE:
<223> OTHER INFORMATION: primer

<400> SEQUENCE: 71
ctatagggcg aattggctag cttatcatta tcaatactcg ccatttcaaa gaata         55

<210> SEQ ID NO 72
<211> LENGTH: 66
<212> TYPE: DNA
<213> ORGANISM: Artificial Sequence
<220> FEATURE:
<223> OTHER INFORMATION: primer

<400> SEQUENCE: 72
ctcgaggggg ggcccggtac ctcgaaacta agttctggtg ttttaaaact aaaaaaaaga    60
ctaact                                                              66

<210> SEQ ID NO 73
<211> LENGTH: 6110
<212> TYPE: DNA
<213> ORGANISM: Artificial Sequence
<220> FEATURE:
<223> OTHER INFORMATION: Synthetic pCS-Ex1 vector

<400> SEQUENCE: 73
ctaaattgta agcgttaata ttttgttaaa attcgcgtta aatttttgtt aaatcagctc    60
```

```
attttttaac caataggccg aaatcggcaa atcccttat aaatcaaaag aatagaccga    120
gatagggttg agtacgcatt taagcataaa cacgcactat gccgttcttc tcatgtatat    180
atatatacag gcaacacgca gatataggtg cgacgtgaac agtgagctgt atgtgcgcag    240
ctcgcgttgc attttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaccaaaa acgcaccgga ctgtaacgag ctactaaaat    420
attgcgaata ccgcttccac aaacattgct caaaagtatc tctttgctat atatctctgt    480
gctatatccc tatataacct acccatccac cttttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780 gatgcctta tcttgaaaaa atgcacccgc agcttcgcta gtaatcagta aacgcgggaa    840
gtggagtcag gctttttta tggaagagaa aatagacacc aaagtagcct tcttctaacc    900
ttaacggacc tacagtgcaa aaagttatca agagactgca ttatagagcg cacaaggag    960 aaaaaaagta atctaagatg ctttgttaga aaaatagcgc tctcgggatg cattttgta   1020 gaacaaaaaa gaagtataga ttcttgttg gtaaaatagc gctctcgcgt tgcatttctg   1080
ttctgtaaaa atgcagctca gattctttgt ttgaaaaatt agcgctctcg cgttgcattt   1140 tgtttaca aaaatgaagc acagattctt cgttggtaaa atagcgcttt cgcgttgcat   1200
ttctgttctg taaaaatgca gctcagattc tttgtttgaa aaattagcgc tctcgcgttg   1260 cattttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattggctag cttatcatta tcaatactcg ccatttcaaa   1440
gaatacgtaa ataattaata gtagtgattt tcctaacttt atttagtcaa aaaattagcc   1500
ttttaattct gctgtaaccc gtacatgccc aaaataggg gcgggttaca cagaatatat   1560
aacatcgtag gtgtctgggt gaacagttta ttcctggcat ccactaaata taatggagcc   1620 cgcttttta gctggcatcc agaaaaaaa agaatcccag caccaaaata ttgttttctt   1680
caccaaccat cagttcatag gtccattctc ttagcgcaac tacagagaac aggggcacaa   1740
acaggcaaaa aacgggcaca acctcaatgg agtgatgcaa cctgcctgga gtaaatgatg   1800
acacaaggca attgacccac gcatgtatct atctcatttt cttacacctt ctattacctt   1860
ctgctctctc tgatttggaa aaagctgaaa aaaaggttg aaaccagttc ctgaaatta   1920 ttcccctact tgactaataa gtatataaag acggtaggta ttgattgtaa ttctgtaaat   1980
ctatttctta aacttcttaa attctacttt tatagttagt ctttttttta gttttaaaac   2040
accagaactt agtttcgagg taccgggccc ccctcgagg tcgacggtat cgataagctt   2100
gatatcgaat tcctgcagcc cggggggatcc actagttcta gagcggccgc caccgcggtg   2160
gagctcggtt ctgcttatcc ttcgacgtg cctgactacg cctgaacccg atgcaaatga   2220
gacgatcgtc tattcctggt ccggttttct ctgccctctc ttctattcac ttttttata   2280 cttatataa aattatataa atgacataac tgaaacgcca cacgtcctct cctattcgtt   2340
aacgcctgtc tgtagcgctg ttactgaagc tgcgcaagta gttttttcac cgtataggcc   2400
```

-continued

| | | | | | |
|---|---|---|---|---|---|
| ctcttttcct | ctctctttct | ttctctcccg | cgctgatctc | ttcttcgaaa | cacagagtgc | 2460 |
| accataccac | cttttcaatt | catcatttt | tttttattct | ttttttgat | ttcggtttcc | 2520 |
| ttgaaatttt | tttgattcgg | taatctccga | acagaaggaa | gaacgaagga | aggagcacag | 2580 |
| acttagattg | gtatatatac | gcatatgtag | tgttgaagaa | acatgaaatt | gcccagtatt | 2640 |
| cttaacccaa | ctgcacagaa | caaaaacctc | caggaaacga | agataaatca | tgtcgaaagc | 2700 |
| tacatataag | gaacgtgctg | ctactcatcc | tagtcctgtt | gctgccaagc | tatttaatat | 2760 |
| catgcacgaa | aagcaaacaa | acttgtgtgc | ttcattggat | gttcgtacca | ccaaggaatt | 2820 |
| actggagtta | gttgaagcat | taggtcccaa | aatttgttta | ctaaaaacac | atgtggatat | 2880 |
| cttgactgat | ttttccatgg | agggcacagt | taagccgcta | aaggcattat | ccgccaagta | 2940 |
| caatttttta | ctcttcgaag | acagaaaatt | tgctgacatt | ggtaatacag | tcaaattgca | 3000 |
| gtactctgcg | ggtgtataca | gaatagcaga | atgggcagac | attacgaatg | cacacggtgt | 3060 |
| ggtgggccca | ggtattgtta | gcggtttgaa | gcaggcggca | gaagaagtaa | caaaggaacc | 3120 |
| tagaggcctt | ttgatgttag | cagaattgtc | atgcaagggc | tccctatcta | ctggagaata | 3180 |
| tactaagggt | actgttgaca | ttgcgaagag | cgacaaagat | tttgttatcg | gctttattgc | 3240 |
| tcaaagagac | atgggtggaa | gagatgaagg | ttacgattgg | ttgattatga | cacccggtgt | 3300 |
| gggtttagat | gacaagggag | acgcattggg | tcaacagtat | agaaccgtgg | atgatgtggt | 3360 |
| ctctacagga | tctgacatta | ttattgttgg | aagaggacta | tttgcaaagg | gaagggatgc | 3420 |
| taaggtagag | ggtgaacgtt | acagaaaagc | aggctgggaa | gcatatttga | agatgcgg | 3480 |
| ccagcaaaac | taatcatgta | attagttatg | tcacgcttac | attcacgccc | tccccccaca | 3540 |
| tccgctctaa | ccgaaaagga | aggagttaga | caacctgaag | tctaggtccc | tatttatttt | 3600 |
| tttatagtta | tgttagtatt | aagaacgtta | tttatatttc | aaattttct | ttttttctg | 3660 |
| tacagacgcg | tgtacgcatg | taacattata | ctgaaaacct | tgcttgagaa | ggttttggga | 3720 |
| cgctcgaagg | ctttaatttg | cgtcgtagc | gctgttactg | aagctgcgca | agtagttttt | 3780 |
| tcaccgtata | ggccctcttt | ttctctctct | ttctttctct | cccgcgctga | tctcttcttc | 3840 |
| gaaacatcat | gaataaaaag | aaaaaggaaa | tcaagaaaaa | aaagccataa | tttatcccac | 3900 |
| atttttttt | attgtcgctg | ttcacaccgc | ataacgaaga | tattggctag | ctaaccagct | 3960 |
| tttgttccct | ttagtgaggg | ttaatttcga | gcttggcgta | atcatggtca | tagctgtttc | 4020 |
| ctgtgtgaaa | ttgttatccg | ctcacaattc | cacacaacat | acgagccgga | agcataaagt | 4080 |
| gtaaagcctg | gggtgcctaa | tgagtgagct | aactcacatt | aattgcgttg | cgctcactgc | 4140 |
| ccgctttcca | gtcgggaaac | ctgtcgtgcc | agctgcatta | atgaatcggc | caacgcgcgg | 4200 |
| ggagaggcgg | tttgcgtatt | gggcgctctt | ccgcttcctc | gctcactgac | tcgctgcgct | 4260 |
| cggtcgttcg | gctgcggcga | gcggtatcag | ctcactcaaa | ggcggtaata | cggttatcca | 4320 |
| cagaatcagg | ggataacgca | ggaaagaaca | tgtgagcaaa | aggccagcaa | aaggccagga | 4380 |
| accgtaaaaa | ggccgcgttg | ctggcgtttt | tccataggct | ccgcccccct | gacgagcatc | 4440 |
| acaaaaatcg | acgctcaagt | cagaggtggc | gaaacccgac | aggactataa | agataccagg | 4500 |
| cgtttccccc | tggaagctcc | ctcgtgcgct | ctcctgttcc | gaccctgccg | cttaccggat | 4560 |
| acctgtccgc | ctttctccct | tcgggaagcg | tggcgctttc | tcatagctca | cgctgtaggt | 4620 |
| atctcagttc | ggtgtaggtc | gttcgctcca | agctgggctg | tgtgcacgaa | ccccccgttc | 4680 |
| agcccgaccg | ctgcgcctta | tccggtaact | atcgtcttga | gtccaacccg | gtaagacacg | 4740 |
| acttatcgcc | actggcagca | gccactggta | acaggattag | cagagcgagg | tatgtaggcg | 4800 |

```
gtgctacaga gttcttgaag tggtggccta actacggcta cactagaagg acagtatttg    4860
gtatctgcgc tctgctgaag ccagttacct tcggaaaaag agttggtagc tcttgatccg    4920
gcaaacaaac caccgctggt agcggtggtt tttttgtttg caagcagcag attacgcgca    4980
gaaaaaaagg atctcaagaa gatcctttga tcttttctac ggggtctgac gctcagtgga    5040
acgaaaactc acgttaaggg attttggtca tgagattatc aaaaaggatc ttcacctaga    5100
tccttttaaa ttaaaaatga agttttaaat caatctaaag tatatatgag taaacttggt    5160
ctgacatcag aagaactcgt caagaaggcg atagaaggcg atgcgctgcg aatcgggagc    5220
ggcgataccg taaagcacga ggaagcggtc agcccattcg ccgccaagct cttcagcaat    5280
atcacgggta gccaacgcta tgtcctgata gcggtccgcc acacccagcc ggccacagtc    5340
gatgaatcca gaaaagcggc cattttccac catgatattc ggcaagcagg catcgccatg    5400
ggtcacgacg agatcctcgc cgtcgggcat gctcgccttg agcctggcga acagttcggc    5460
tggcgcgagc ccctgatgct cttcgtccag atcatcctga tcgacaagac cggcttccat    5520
ccgagtacgt gctcgctcga tgcgatgttt cgcttggtgg tcgaatgggc aggtagccgg    5580
atcaagcgta tgcagccgcc gcattgcatc agccatgatg gatactttct cggcaggagc    5640
aaggtgagat gacaggagat cctgccccgg cacttcgccc aatagcagcc agtcccttcc    5700
cgcttcagtg acaacgtcga gcacagctgc gcaaggaacg cccgtcgtgg ccagccacga    5760
tagccgcgct gcctcgtctt gcagttcatt cagggcaccg gacaggtcgg tcttgacaaa    5820
aagaaccggg cgcccctgcg ctgacagccg aacacggcg gcatcagagc agccgattgt    5880
ctgttgtgcc cagtcatagc cgaatagcct ctccacccaa gcggccggag aacctgcgtg    5940
caatccatct tgttcaattc gagtgcattc aacatcagcc atactcttcc tttttcaata    6000
ttattgaagc atttatcagg gttattgtct catgagcgga tacatatttg aatgtattta    6060
gaaaaataaa caaatagggg ttccgcgcac atttccccga aaagtgccac    6110

<210> SEQ ID NO 74
<211> LENGTH: 55
<212> TYPE: DNA
<213> ORGANISM: Artificial Sequence
<220> FEATURE:
<223> OTHER INFORMATION: primer

<400> SEQUENCE: 74
accagaactt agtttcgaga aacaatgaat caacaggata ttgaacaggt ggtga    55

<210> SEQ ID NO 75
<211> LENGTH: 50
<212> TYPE: DNA
<213> ORGANISM: Artificial Sequence
<220> FEATURE:
<223> OTHER INFORMATION: primer

<400> SEQUENCE: 75
gtaaggataa gcagaaccgt taaacaatgc gaaacgcatc gactaataca    50

<210> SEQ ID NO 76
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 76
```

```
ctaaattgta agcgttaata ttttgttaaa attcgcgtta aattttttgtt aaatcagctc      60
atttttttaac caataggccg aaatcggcaa aatcccttat aaatcaaaag aatagaccga    120
gatagggttg agtacgcatt taagcataaa cacgcactat gccgttcttc tcatgtatat    180
atatatacag gcaacacgca gatataggtg cgacgtgaac agtgagctgt atgtgcgcag    240
ctcgcgttgc attttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaccaaaa acgcaccgga ctgtaacgag ctactaaaat     420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca tttttatgt ttatctctag tattactctt tagacaaaaa aattgtagta     600
agaactattc atagagtgaa tcgaaaacaa tacgaaaatg taaacatttc ctatacgtag    660
tatatagaga caaatagaa gaaccgttc ataattttct gaccaatgaa gaatcatcaa      720
cgctatcact ttctgttcac aaagtatgcg caatccacat cggtatagaa tataatcggg    780
gatgccttta tcttgaaaaa atgcacccgc agcttcgcta gtaatcagta aacgcgggaa    840
gtggagtcag gctttttta tggaagagaa aatagacacc aaagtagcct tcttctaacc     900
ttaacggacc tacagtgcaa aaagttatca agagactgca ttatagagcg cacaaaggag    960
aaaaaaagta atctaagatg ctttgttaga aaaatagcgc tctcgggatg cattttttgta  1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgtttttaca aaaatgaagc acagattctt cgttggtaaa atagcgcttt cgcgttgcat  1200
ttctgttctg taaaaatgca gctcagattc tttgtttgaa aaattagcgc tctcgcgttg   1260
catttttgtt ctacaaaatg aagcacagat gcttcgttaa tgtgctgcaa ggcgattaag   1320
ttgggtaacg ccagggttt cccagtcacg acgttgtaaa acgacggcca gtgaattgta    1380
atacgactca ctatagggcg aattggctag cttatcatta tcaatactcg ccatttcaaa   1440
gaatacgtaa ataattaata gtagtgattt tcctaacttt atttagtcaa aaaattagcc   1500
ttttaattct gctgtaaccc gtacatgccc aaaatagggg gcgggttaca cagaatatat   1560
aacatcgtag gtgtctgggt gaacagttta ttcctggcat ccactaaata taatggagcc   1620
cgcttttta gctggcatcc agaaaaaaaa agaatcccag caccaaaata ttgttttctt    1680
caccaaccat cagttcatag gtccattctc ttagcgcaac tacagagaac aggggcacaa   1740
acaggcaaaa aacgggcaca acctcaatgg agtgatgcaa cctgcctgga gtaaatgatg   1800
acacaaggca attgacccac gcatgtatct atctcatttt cttacacctt ctattacctt   1860
ctgctctctc tgatttggaa aaagctgaaa aaaaaggttg aaaccagttc cctgaaatta   1920
ttcccctact tgactaataa gtatataaag acggtaggta ttgattgtaa ttctgtaaat   1980
ctatttctta aacttcttaa attctacttt tatagttagt ctttttttta gttttaaaac    2040
accagaactt agtttcgaga aacaatgaat caacaggata ttgaacaggt ggtgaaagcg   2100
gtactgctga aaatgcaaag cagtgacacg ccgtccgccg ccgttcatga gatgggcgtt   2160
ttcgcgtccc tggatgacgc cgttgcggca gccaaagtcg cccagcaagg gttaaaaagc   2220
gtggcaatgc gccagttagc cattgctgcc attcgtgaag caggcgaaaa acacgccaga   2280
gatttagcga aacttgccgt cagtgaaacc ggcatgggc gcgttgaaga taaatttgca    2340
aaaaacgtcg ctcaggcgcg cggcacacca ggcgttgagt gcctctctcc gcaagtgctg   2400
```

```
actggcgaca acggcctgac cctaattgaa aacgcaccct ggggcgtggt ggcttcggtg      2460
acgccttcca ctaacccggc ggcaaccgta attaacaacg ccatcagcct gattgccgcg      2520
ggcaacagcg tcattttttgc cccgcatccg gcggcgaaaa aagtctccca gcgggcgatt     2580
acgctgctca accaggcgat tgttgccgca ggtgggccgg aaaacttact ggttactgtg      2640
gcaaatccgg atatcgaaac cgcgcaacgc ttgttcaagt ttccgggtat cggcctgctg      2700
gtggtaaccg gcggcgaagc ggtagtagaa gcggcgcgta acacaccaa taaacgtctg      2760 attgccgcag gcgctggcaa cccgccggta gtggtggatg aaaccgccga cctcgcccgt      2820
gccgctcagt ccatcgtcaa aggcgcttct ttcgataaca acatcatttg tgccgacgaa     2880
aaggtactga ttgttgttga tagcgtagcc gatgaactga tgcgtctgat ggaaggccag     2940
cacgcggtga aactgaccgc agaacaggcg cagcagctgc aaccggtgtt gctgaaaaat     3000
atcgacgagc gcggaaaagg caccgtcagc cgtgactggg ttggtcgcga cgcaggcaaa     3060
atcgcggcgg caatcggcct taaagttccg caagaaacgc gcctgctgtt tgtggaaacc     3120
accgcagaac atccgtttgc cgtgactgaa ctgatgatgc cggtgttgcc cgtcgtgcgc     3180
gtcgccaacg tggcggatgc cattgcgcta gcggtgaaac tggaaggcgg ttgccaccac     3240
acggcggcaa tgcactcgcg caacatcgaa acatgaacc agatggcgaa tgctattgat      3300
accagcattt tcgttaagaa cggaccgtgc attgccgggc tggggctggg cggggaaggc     3360
tggaccacca tgaccatcac cacgccaacc ggtgaagggg taaccagcgc gcgtacgttt     3420
gtccgtctgc gtcgctgtgt attagtcgat gcgtttcgca ttgtttaacg gttctgctta     3480
tccttacgac gtgcctgact acgcctgaac ccgatgcaaa tgagacgatc gtctattcct     3540
ggtccggttt tctctgccct ctcttctatt cacttttttt atactttata taaaattata     3600
taaatgacat aactgaaacg ccacacgtcc tctcctattc gttaacgcct gtctgtagcg     3660
ctgttactga agctgcgcaa gtagtttttt caccgtatag gccctctttt tctctctctt     3720
tctttctctc ccgcgctgat ctcttcttcg aaacacagag tgcaccatac caccttttca     3780
attcatcatt ttttttttat tctttttttt gatttcggtt tccttgaaat ttttttgatt     3840
cggtaatctc cgaacagaag gaagaacgaa ggaaggagca cagacttaga ttggtatata     3900
tacgcatatg tagtgttgaa gaaacatgaa attgcccagt attcttaacc caactgcaca     3960
gaacaaaaac ctccaggaaa cgaagataaa tcatgtcgaa agctacatat aaggaacgtg     4020
ctgctactca tcctagtcct gttgctgcca agctatttaa tatcatgcac gaaaagcaaa     4080
caaacttgtg tgcttcattg gatgttcgta ccaccaagga attactggag ttagttgaag    4140
cattaggtcc caaaatttgt ttactaaaaa cacatgtgga tatcttgact gattttttcca    4200 tggagggcac agttaagccg ctaaaggcat tatccgccaa gtacaatttt ttactcttcg    4260
aagacagaaa atttgctgac attggtaata cagtcaaatt gcagtactct gcgggtgtat    4320
acagaatagc agaatgggca gacattacga atgcacacgg tgtggtgggc ccaggtattg    4380
ttagcggttt gaagcaggcg gcagaagaag taacaaagga acctagaggc cttttgatgt    4440
tagcagaatt gtcatgcaag ggctccctat ctactggaga atatactaag ggtactgttg    4500
acattgcgaa gagcgacaaa gattttgtta tcggctttat tgctcaaaga gacatggtg    4560 gaagagatga aggttacgat tggttgatta tgacacccgg tgtgggttta gatgacaagg    4620
gagacgcatt gggtcaacag tatagaaccg tggatgatgt ggtctctaca ggatctgaca    4680
ttattattgt tggaagagga ctatttgcaa agggaaggga tgctaaggta gagggtgaac    4740
```

```
gttacagaaa agcaggctgg gaagcatatt tgagaagatg cggccagcaa aactaatcat    4800
gtaattagtt atgtcacgct tacattcacg ccctcccccc acatccgctc taaccgaaaa    4860
ggaaggagtt agacaacctg aagtctaggt ccctatttat ttttttatag ttatgttagt    4920
attaagaacg ttatttatat ttcaaatttt tcttttttt ctgtacagac gcgtgtacgc    4980
atgtaacatt atactgaaaa ccttgcttga aaggttttg ggacgctcga aggctttaat    5040
ttgcgtctgt agcgctgtta ctgaagctgc gcaagtagtt ttttcaccgt ataggccctc    5100
tttttctctc tctttctttc tctcccgcgc tgatctcttc ttcgaaacat catgaataaa    5160
aagaaaaagg aaatcaagaa aaaaagcca taatttatcc cacattttt tttattgtcg    5220 ctgttcacac cgcataacga agatattggc tagctaacca gcttttgttc cctttagtga    5280
gggttaattt cgagcttggc gtaatcatgg tcatagctgt ttcctgtgtg aaattgttat    5340
ccgctcacaa ttccacacaa catacgagcc ggaagcataa agtgtaaagc ctggggtgcc    5400
taatgagtga gctaactcac attaattgcg ttgcgctcac tgcccgcttt ccagtcggga    5460
aacctgtcgt gccagctgca ttaatgaatc ggccaacgcg cggggagagg cggtttgcgt    5520
attgggcgct cttccgcttc ctcgctcact gactcgctgc gctcggtcgt tcggctgcgg    5580
cgagcggtat cagctcactc aaaggcggta atacggttat ccacagaatc aggggataac    5640
gcaggaaaga acatgtgagc aaaaggccag caaaaggcca ggaaccgtaa aaaggccgcg    5700
ttgctggcgt ttttccatag gctccgcccc cctgacgagc atcacaaaaa tcgacgctca    5760
agtcagaggt ggcgaaaccc gacaggacta taaagatacc aggcgtttcc ccctggaagc    5820
tccctcgtgc gctctcctgt tccgaccctg ccgcttaccg gatacctgtc cgcctttctc    5880
ccttcgggaa gcgtggcgct ttctcatagc tcacgctgta ggtatctcag ttcggtgtag    5940
gtcgttcgct ccaagctggg ctgtgtgcac gaaccccccg ttcagcccga ccgctgcgcc    6000
ttatccggta actatcgtct tgagtccaac ccggtaagac acgacttatc gccactggca    6060
gcagccactg gtaacaggat tagcagagcg aggtatgtag gcggtgctac agagttcttg    6120
aagtggtggc ctaactacgg ctacactaga aggacagtat ttggtatctg cgctctgctg    6180
aagccagtta ccttcggaaa aagagttggt agctcttgat ccggcaaaca aaccaccgct    6240
ggtagcggtg gtttttttgt ttgcaagcag cagattacgc gcagaaaaaa aggatctcaa    6300
gaagatcctt tgatcttttc tacggggtct gacgctcagt ggaacgaaaa ctcacgttaa    6360
gggattttgg tcatgagatt atcaaaaagg atcttcacct agatcctttt aaattaaaaa    6420
tgaagtttta atcaatcta aagtatatat gagtaaactt ggtctgacat cagaagaact    6480
cgtcaagaag gcgatagaag gcgatgcgct gcgaatcggg agcggcgata ccgtaaagca    6540
cgaggaagcg gtcagcccat tcgccgccaa gctcttcagc aatatcacgg gtagccaacg    6600
ctatgtcctg atagcggtcc gccacaccca gccggccaca gtcgatgaat ccagaaaagc    6660
ggccattttc caccatgata ttcggcaagc aggcatcgcc atgggtcacg acgagatcct    6720
cgccgtcggg catgctcgcc ttgagcctgg cgaacagttc ggctggcgcg agccctgat    6780 gctcttcgtc cagatcatcc tgatcgacaa gaccggcttc catccgagta cgtgctcgct    6840
cgatgcgatg tttcgcttgg tggtcgaatg gcaggtagc cggatcaagc gtatgcagcc    6900
gccgcattgc atcagccatg atggatactt tctcggcagg agcaaggtga gatgacagga    6960
gatcctgccc cggcacttcg cccaatagca gccagtccct tcccgcttca gtgacaacgt    7020
cgagcacagc tgcgcaagga acgccgtcg tggccagcca cgatagccgc gctgcctcgt    7080
cttgcagttc attcagggca ccggacaggt cggtcttgac aaaaagaacc gggcgcccct    7140
```

-continued

```
gcgctgacag ccggaacacg gcggcatcag agcagccgat tgtctgttgt gcccagtcat      7200
agccgaatag cctctccacc caagcggccg gagaacctgc gtgcaatcca tcttgttcaa      7260
ttcgagtgca ttcaacatca gccatactct cctttttca atattattga agcatttatc       7320
agggttattg tctcatgagc ggatacatat ttgaatgtat ttagaaaaat aaacaaatag      7380
gggttccgcg cacatttccc cgaaaagtgc cac                                   7413
```

<210> SEQ ID NO 77
<211> LENGTH: 59
<212> TYPE: DNA
<213> ORGANISM: Artificial Sequence
<220> FEATURE:
<223> OTHER INFORMATION: primer

<400> SEQUENCE: 77

```
aatcttgtgc tattgcagtc ctcttttata tacagtataa tacgactcac tatagggcg       59
```

<210> SEQ ID NO 78
<211> LENGTH: 60
<212> TYPE: DNA
<213> ORGANISM: Artificial Sequence
<220> FEATURE:
<223> OTHER INFORMATION: primer

<400> SEQUENCE: 78

```
atgcgaattg cgtaattcac ggcgataacg tagtattaat taaccctcac taaagggaac      60
```

<210> SEQ ID NO 79
<211> LENGTH: 19
<212> TYPE: DNA
<213> ORGANISM: Artificial Sequence
<220> FEATURE:
<223> OTHER INFORMATION: primer

<400> SEQUENCE: 79

```
gcccacaact tatcaagtg                                                   19
```

<210> SEQ ID NO 80
<211> LENGTH: 19
<212> TYPE: DNA
<213> ORGANISM: Artificial Sequence
<220> FEATURE:
<223> OTHER INFORMATION: primer

<400> SEQUENCE: 80

```
ttataagaca agcgcaggg                                                   19
```

<210> SEQ ID NO 81
<211> LENGTH: 65
<212> TYPE: DNA
<213> ORGANISM: Artificial Sequence
<220> FEATURE:
<223> OTHER INFORMATION: primer

<400> SEQUENCE: 81

```
atgaacgagc tgaacactgt ttcgactaac tccagtgact ccaccccagt cacgacgttg      60
taaaa                                                                  65
```

<210> SEQ ID NO 82
<211> LENGTH: 65
<212> TYPE: DNA
<213> ORGANISM: Artificial Sequence
<220> FEATURE:

<223> OTHER INFORMATION: primer

<400> SEQUENCE: 82
tcaataccag cctaactcgg aatcgtccaa cagcttccag ccgataggtt tcccgactgg    60
aaagc    65

<210> SEQ ID NO 83
<211> LENGTH: 23
<212> TYPE: DNA
<213> ORGANISM: Artificial Sequence
<220> FEATURE:
<223> OTHER INFORMATION: primer

<400> SEQUENCE: 83
cacgcttctt cgattctcac att    23

<210> SEQ ID NO 84
<211> LENGTH: 22
<212> TYPE: DNA
<213> ORGANISM: Artificial Sequence
<220> FEATURE:
<223> OTHER INFORMATION: primer

<400> SEQUENCE: 84
ctgaggagaa gggagaacct ga    22

<210> SEQ ID NO 85
<211> LENGTH: 296
<212> TYPE: DNA
<213> ORGANISM: Artificial Sequence
<220> FEATURE:
<223> OTHER INFORMATION: Synthetic cyc1 promoter

<400> SEQUENCE: 85 tttgcgagc gttggttggt ggatcaagcc cacgcgtagg caatcctcga gcagatccgc    60
caggcgtgta tatatagcgt ggatggccag gcaactttag tgctgacaca tacaggcata    120
tatatatgtg tgcgacgaca catgatcata tggcatgcat gtgctctgta tgtatataaa    180
actcttgttt tcttcttttc tctaaatatt ctttccttat acattaggac ctttgcagca    240
taaattacta tacttctata gacacacaaa cacaaataca cactaaat taataa    296

<210> SEQ ID NO 86
<211> LENGTH: 27
<212> TYPE: DNA
<213> ORGANISM: Artificial Sequence
<220> FEATURE:
<223> OTHER INFORMATION: primer

<400> SEQUENCE: 86
cggaattcat ttggcgagcg ttggttg    27

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
cggaattctt agtgtgtgta tttgtgtttg c    31

<210> SEQ ID NO 88
<211> LENGTH: 64

```
<212> TYPE: DNA
<213> ORGANISM: Artificial Sequence
<220> FEATURE:
<223> OTHER INFORMATION: primer

<400> SEQUENCE: 88
atacatccta ttattcttga aaaaaagtgc ggggctccag agctccaacc ctatctcggt    60
ctat                                                                64

<210> SEQ ID NO 89
<211> LENGTH: 65
<212> TYPE: DNA
<213> ORGANISM: Artificial Sequence
<220> FEATURE:
<223> OTHER INFORMATION: primer

<400> SEQUENCE: 89
tttatttaat tagcgtactt attatgtgtg gagaattata ttcctttatt aatttagtgt    60
gtgta                                                               65

<210> SEQ ID NO 90
<211> LENGTH: 25
<212> TYPE: DNA
<213> ORGANISM: Artificial Sequence
<220> FEATURE:
<223> OTHER INFORMATION: primer

<400> SEQUENCE: 90
gcgtgatacc tattacgtat tacgt                                         25

<210> SEQ ID NO 91
<211> LENGTH: 23
<212> TYPE: DNA
<213> ORGANISM: Artificial Sequence
<220> FEATURE:
<223> OTHER INFORMATION: primer

<400> SEQUENCE: 91
ttggctcaga gataccttgt ggg                                           23

<210> SEQ ID NO 92
<211> LENGTH: 65
<212> TYPE: DNA
<213> ORGANISM: Artificial Sequence
<220> FEATURE:
<223> OTHER INFORMATION: primer

<400> SEQUENCE: 92
cagagtatac tgctctttct aatgccttttt ccatcatgtt actacccagt cacgacgttg   60
taaaa                                                               65

<210> SEQ ID NO 93
<211> LENGTH: 65
<212> TYPE: DNA
<213> ORGANISM: Artificial Sequence
<220> FEATURE:
<223> OTHER INFORMATION: primer

<400> SEQUENCE: 93
ttaagcaccg atgataccaa cggacttacc ttcagcaatt cttttaggtt tcccgactgg    60
aaagc                                                               65

<210> SEQ ID NO 94
```

```
<211> LENGTH: 21
<212> TYPE: DNA
<213> ORGANISM: Artificial Sequence
<220> FEATURE:
<223> OTHER INFORMATION: primer

<400> SEQUENCE: 94
ccagagctcc acattggtga c                                              21

<210> SEQ ID NO 95
<211> LENGTH: 24
<212> TYPE: DNA
<213> ORGANISM: Artificial Sequence
<220> FEATURE:
<223> OTHER INFORMATION: primer

<400> SEQUENCE: 95
ggcaccttct tgttgttcaa actt                                           24

<210> SEQ ID NO 96
<211> LENGTH: 21
<212> TYPE: DNA
<213> ORGANISM: Artificial Sequence
<220> FEATURE:
<223> OTHER INFORMATION: Synthetic HXT1 forward primer

<400> SEQUENCE: 96
actggtgcca tcaacttcta c                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic HXT1 reverse primer

<400> SEQUENCE: 97
aacaccttcg gcgtacatat c                                              21

<210> SEQ ID NO 98
<211> LENGTH: 21
<212> TYPE: DNA
<213> ORGANISM: Artificial Sequence
<220> FEATURE:
<223> OTHER INFORMATION: Synthetic HXT2 forward primer

<400> SEQUENCE: 98
tccactttcg tggccttata c                                              21

<210> SEQ ID NO 99
<211> LENGTH: 24
<212> TYPE: DNA
<213> ORGANISM: Artificial Sequence
<220> FEATURE:
<223> OTHER INFORMATION: Synthetic HXT2 reverse primer

<400> SEQUENCE: 99
gacaccgaca gtagagaaga taac                                           24

<210> SEQ ID NO 100
<211> LENGTH: 22
<212> TYPE: DNA
<213> ORGANISM: Artificial Sequence
<220> FEATURE:
<223> OTHER INFORMATION: Synthetic HXT3 forward primer

<400> SEQUENCE: 100
```

```
gtcgctccta aggaaatgag ag                                             22

<210> SEQ ID NO 101
<211> LENGTH: 22
<212> TYPE: DNA
<213> ORGANISM: Artificial Sequence
<220> FEATURE:
<223> OTHER INFORMATION: Synthetic HXT3 reverse primer

<400> SEQUENCE: 101
ggaggttgga cacatcttgt at                                             22

<210> SEQ ID NO 102
<211> LENGTH: 21
<212> TYPE: DNA
<213> ORGANISM: Artificial Sequence
<220> FEATURE:
<223> OTHER INFORMATION: Synthetic HXT4 forward primer

<400> SEQUENCE: 102
tcaggtctcc tcgtgctata a                                              21

<210> SEQ ID NO 103
<211> LENGTH: 22
<212> TYPE: DNA
<213> ORGANISM: Artificial Sequence
<220> FEATURE:
<223> OTHER INFORMATION: Synthetic HXT4 reverse primer

<400> SEQUENCE: 103
ggaggttgga cacatcttgt at                                             22

<210> SEQ ID NO 104
<211> LENGTH: 22
<212> TYPE: DNA
<213> ORGANISM: Artificial Sequence
<220> FEATURE:
<223> OTHER INFORMATION: Synthetic HXT7 forward primer

<400> SEQUENCE: 104
catctctctg ctgttgactc ag                                             22

<210> SEQ ID NO 105
<211> LENGTH: 22
<212> TYPE: DNA
<213> ORGANISM: Artificial Sequence
<220> FEATURE:
<223> OTHER INFORMATION: Synthetic HXT7 reverse primer

<400> SEQUENCE: 105
tgctcttcac cttcaccata ag                                             22
```

YEAST CELL HAVING DECREASED RGT1 ACTIVITY, METHOD OF PRODUCING THE SAME, AND METHOD OF PRODUCING PRODUCT USING THE SAME

RELATED APPLICATION

This application claims the benefit of Korean Patent Application No. 10-2014-0191130, filed on Dec. 26, 2014, in the Korean Intellectual Property Office, the disclosure of which is incorporated herein in its entirety by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 145,131 Byte ASCII (Text) file named, "720522_ST25.TXT-Revised" created on Mar. 17, 2016.

BACKGROUND

1. Field

The present disclosure relates to a recombinant (i.e., genetically engineered) yeast cell that produces a glycolytic intermediate or a glycolytic intermediate-derived substance, a method of producing the same, and a method of producing the glycolytic intermediate or the glycolytic intermediate-derived substance using the same.

2. Description of the Related Art

Products such as organic acids and alcohols have been widely used as building block materials in the food, medical, and chemical industries. These substances have been known to be produced from petroleum, but methods of producing the substances using environmentally friendly microorganisms, such as yeasts, have also been studied.

These methods of producing products using microorganisms require a long fermentation time and high cost for product isolation. Thus there is a demand to improve the productivity of the microorganisms in the methods of producing products such as organic acids and alcohols.

Many approaches to increase productivity rely on the assumption that a production environment characteristic, such as acid stress, limits the productivity of microorganisms in said production environment. A main focus for strain improvement relates to the product formation rate itself by enhancing the enzymatic activities of microorganism that are involved in product formation. Examples of the enzymatic activities, which are generally enhanced, may include central metabolic pathways such as glycolysis, which provide intermediates required for the production of products.

Accordingly, there is still demand for a yeast cell having an enhanced ability to produce a product such as an organic acid or alcohol, as well as methods of producing the product using the same.

SUMMARY

A genetically engineered yeast cell having a decreased RGT1 protein activity compared to the RGT1 protein activity of a parent cell thereof, wherein the genetically engineered yeast cell has an increased productivity of a glycolytic intermediate or a glycolytic intermediate-derived substance compared to a parent cell thereof, and the genetically engineered yeast cell comprises a genetic modification that decreases the RGT1 protein activity. Another aspect provides a method of producing the genetically engineered yeast cell capable of effectively producing a glycolytic intermediate or the glycolytic intermediate-derived substance comprising introducing a gene encoding an enzyme that catalyzes the conversion of pyruvate into lactate into a yeast cell; and disrupting a gene encoding an RGT1 protein in the yeast cell.

Still another aspect provides a method of effectively producing the glycolytic intermediate or the glycolytic intermediate-derived substance using the genetically engineered yeast cell introducing a gene encoding an enzyme that catalyzes the conversion of pyruvate into lactate into a yeast cell; and disrupting a gene encoding an RGT1 protein in the yeast cell.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
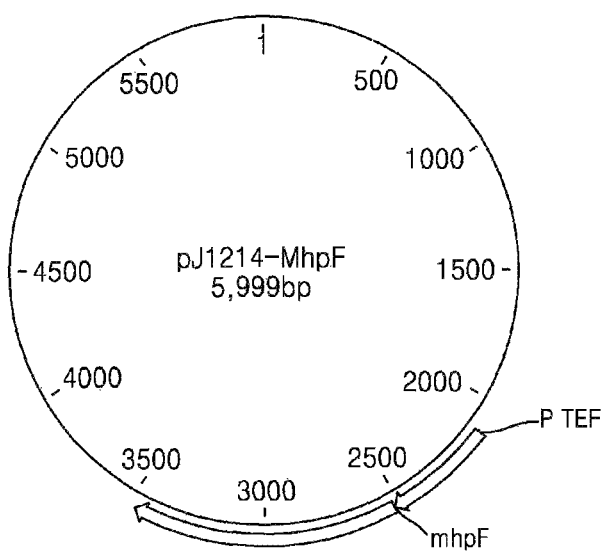
FIG. 1 shows a cleavage map of a pJ1214-MhpF vector.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

As used herein, the term "decrease in activity" or "decreased activity" means that a cell (e.g., a genetically engineered yeast cell) has an activity of an enzyme or a polypeptide that is lower than that measured in a parent cell. Also, the "decrease in activity" or "decreased activity" may refer to situations where an isolated enzyme or a polypeptide has an activity that is lower than that of an original or a wild-type enzyme or polypeptide (e.g., an enzyme or polypeptide from a parent cell). The decrease in activity or decreased activity encompasses no activity. For example, a modified (e.g., genetically engineered) cell or enzyme may have an enzymatic activity of converting a substrate to a product, which is about 20% or more, about 30% or more, about 40% or more, about 50% or more, about 55% or more, about 60% or more, about 70% or more, about 75% or more, about 80% or more, about 85% or more, about 90% or more, about 95% or more, or about 100% decreased, compared to that of a cell or enzyme that does not have the genetic modification, e.g., an enzyme from a parent cell or a "wild-type" cell or enzyme. Decreased activity of an enzyme or a cell may be confirmed by any method known in the art, for example, the activity of an enzyme may be measured by a colorimetric assay or a radiometric assay. The decrease in activity of an enzyme includes situations in which an enzyme has no activity or has decreased activity even though the enzyme is expressed, or the case that an enzyme-encoding gene is not expressed or is expressed at a low level, compared to a cell having a non-modified gene, i.e., a parent cell or a wild-type cell. The cell having decreased activity may have one or more genetic modifications for decreasing the activity of the enzyme or polypeptide, compared to a cell having no genetic modification.

With respect to a particular genetic modification, the "parent cell" may be a cell that lacks a particular genetic modification or set of modifications, but is identical in all other respects. A parent cell, thus, includes but is not limited to a non-genetically engineered cell of the same type as an engineered yeast cell (e.g., a "wild-type" cell) or a genetically engineered cell that serves as a starting point for further modifications that results in a particular genetically engineered cell. Thus, the parent cell may be a cell that is used as a starting material to produce a genetically engineered yeast cell having decreased or increased biological activity, such as the activity of a given protein or enzyme (e.g., a protein having a sequence identity of about 95% or more to an RGT1 protein or a protein having a sequence identity of about 95% or more to an HXK2 protein).

As used herein, the term "disruption" and "disruption mutation" refers to a genetic modification to reduce the expression of a referenced gene. The disruption includes a genetic manipulation whereby the referenced gene is not expressed (hereinafter, referred to as "inactivation" of a gene) or a genetic manipulation whereby the gene is expressed at a reduced level (hereinafter, referred to as "attenuation" of a gene). The inactivation includes not only the lack of expression of any product of a gene but also expression of a non-functional product even though the gene is expressed. Attenuation includes a reduction in the expression level of a functional product of a gene. That is, the attenuation includes situations where there is a reduction in the expression level of the functional product even if the entire expression of the gene is increased. Herein, the functional product of the gene refers to a product retaining a biochemical or physiological function (e.g., enzymatic activity) of the product (e.g., enzyme) encoded by the gene of a parent cell or a wild-type cell. As used herein the term "disruption" also includes functional disruption of the gene caused by a genetic modification. Genetic modifications which may result in the disruption of a gene include introducing a polynucleotide encoding a polypeptide into a cell; a substitution, insertion, or deletion of one or more nucleotides in the genetic material of a parent cell; or a chemical modification of the genetic material of the parent cell. Such genetic modifications include modification of coding regions and functional fragments thereof. In addition, the genetic modifications include modifications of non-coding regulatory regions, which alter the expression of a gene or an operon. The non-coding regions include a 5'-non coding sequence and/or a 3'-non coding sequence.

The disruption of a gene may be achieved by genetic manipulation such as homologous recombination, directed mutagenesis, or molecular evolution. If a cell includes a plurality of the same genes, or two or more different paralogs of a gene, one or more of the genes may be disrupted. For example, the genetic modification may be performed by transforming the cell with a vector containing a partial sequence of the gene, culturing the cell so that the gene is disrupted by homogonous recombination of the sequence with an endogenous gene of the cell, and then selecting cells, in which the homologous recombination occurred, using a selection marker.

The term "increase in activity" or "increased activity", as used herein, may refer to a detectable increase in an activity of a cell, a protein, or an enzyme. The "increased activity" or "increase in activity" may also refer to an activity level of a modified (e.g., genetically engineered) cell, protein, or enzyme that is higher than that of a comparative cell, protein, or enzyme of the same type, such as a cell, protein, or enzyme that does not have a given modification (e.g., parent cell or "wild-type" cell, protein, or enzyme). "Cell activity" may refer to an activity of a particular protein or enzyme of a cell. For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more than an activity of a cell, protein, or enzyme of the same type that does not have the genetic modification, e.g., a parent cell or protein or enzyme from a parent cell. A cell having an increased activity of a protein or an enzyme may be identified by using any method known in the art. For instance, the increased activity of a protein or an enzyme may be identified by measuring an amount of a product which is prepared from the reaction catalyzed by the protein or the enzyme. The cell having the increased activity may have one or more genetic modifications of increasing the activity of the enzyme or polypeptide, compared to a cell without the genetic modifications.

An increased activity of a polypeptide may be achieved by increasing an expression or a specific activity of the polypeptide. The increased expression may be caused by introducing a polynucleotide encoding the polypeptide into a cell, by increasing the copy number of an existing gene in the cell by amplification, or by modifying a regulatory region of the polynucleotide. Increasing the gene copy number may be achieved, for instance, by introduction of a polynucleotide encoding a gene, change of a promoter from a relatively weak promoter to a relatively strong promoter, or selective pressures advantageous to gene expression. The modification in the regulatory region of the polynucleotide may have a modification in an expression regulatory sequence of the gene. The regulatory sequence may be a promoter sequence or a transcription terminator sequence for expression of the gene. The regulatory sequence may also be a nucleotide sequence encoding a motif which may influence the expression of the gene. The motif may be, for example, a secondary structure-stabilizing motif, an RNA destabilizing motif, a splice-activating motif, a polyadenylation motif, an adenine-rich sequence, or an endonuclease recognition site.

The "increase in the copy number" may be caused by introduction or amplification of a gene, and may be achieved by genetically engineering a cell so that the cell possesses a gene that does not exist in a non-engineered cell or parent cell. The introduction of the gene may be mediated by a vehicle such as a vector. The introduction may be a transient introduction in which the gene is not integrated into a genome, or by non-transient integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

As used herein, the term "gene" refers to a nucleic acid fragment expressing a specific protein, and may or may not include regulatory elements such as a 5'-non coding sequence and/or a 3'-non coding sequence.

As used herein, the term "sequence identity" of a nucleic acid or a polypeptide refers to a degree of identity between bases or amino acid residues of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN and BLASTP (NCBI), CLC Main Workbench (CLC bio), MegAlign™ (DNASTAR Inc), etc.

Various levels of sequence identity may be used to identify various types of polypeptides or polynucleotides having the same or similar functions or activities. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used as a reference.

As used herein, the term "exogenous" means that a referenced molecule or a referenced activity is introduced into a host cell. The molecule can be introduced, for example, by introducing a coding nucleic acid into the genetic material of the host, such as integration into a host chromosome, or as a non-chromosomal genetic material such as a plasmid. The term "exogenous", when used in reference to expression of a coding nucleic acid, refers to introduction of the coding nucleic acid in an expressible form into a cell. The term "exogenous", when used in reference to biosynthetic activity, refers to an activity that is introduced into a host parent cell. The source may be, for example, a homologous or heterologous coding nucleic acid that causes the referenced activity following introduction into the host parent cell. The term "endogenous" refers to a referenced molecule or activity that is present in the host cell prior to a given genetic modification. Similarly, the term "endogenous", when used in reference to expression of a coding nucleic acid, refers to expression of a coding nucleic acid contained in a cell prior to a given genetic modification. The term "heterologous" refers to a molecule or activity derived from a source other than the referenced species, whereas "homologous" refers to a molecule or activity derived from or native to the host parent cell. Accordingly, exogenous expression of a coding nucleic acid may utilize either or both of heterologous and homologous coding nucleic acids.

As used herein, the term "genetic engineering" or "genetically engineered" refers to action of introducing one or more genetic modifications into a cell or a cell containing genetic modifications.

As used herein, the term "lactate" refers to "lactic acid" or a salt thereof.

An embodiment provides a recombinant yeast cell having decreased activity of RGT1 protein and an increased ability to produce a glycolytic intermediate or a glycolytic intermediate-derived substance, compared to a parent cell, in which the yeast cell includes a genetic modification that decreases RGT1 activity.

In the yeast cell, RGT1 protein may be a glucose-responsive transcription factor or a glucose transport transcription regulator which regulates the expression of several glucose transporter (HXT) genes in response to glucose. RGT1 may be also referred to as "restores glucose transport protein 1". RGT1 associates with Mth1/Std1 to repress hexose transporter (HXT) expression at low levels of glucose, and high levels of glucose cause PKA to repress HXT expression. The hexose transporter refers to any protein such as enzyme, which can translocate a hexose such as glucose or fructose across the plasma membrane. The hexose transporter may be exemplified by HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3, or RGT2. RGT1 protein may have a sequence identity of 75% or more, 80% or more, 85% or more, 90% or more, 95% or more, 96% or more, 97% or more, 98% or more, 99% or more, or 100% to an amino acid sequence of SEQ ID NO. 1, or a yeast homologue thereof. RGT1 protein may be encoded by a polynucleotide sequence of SEQ ID NO. 2. RGT1 gene may have a sequence identity of 75% or more, 80% or more, 85% or more, 90% or more, 95% or more, 96% or more, 97% or more, 98% or more, 99% or more, or 100% to a polynucleotide sequence encoding the amino acid of SEQ ID NO. 1. The RGT1 gene may have a polynucleotide sequence (NM_001179604.3) of SEQ ID NO. 2.

The yeast cell having a modification of deleting or disrupting the gene encoding RGT eliminates repression of HXT expression via association with Mth1/Std1, and increases glucose transport by constitutive expression of HXT at low levels of glucose. Further, the yeast cell induces HTX expression to increase glucose transport irrespective of PKA activity at high levels of glucose.

In the yeast cell, an endogenous gene encoding RGT1 protein may be disrupted. In the yeast cell, the endogenous gene encoding RGT1 protein may be disrupted so that its expression is low enough to decrease the RGT1 protein activity, compared to its parent cell.

In the yeast cell, the yeast cell may further include a genetic modification that decreases HXK2 activity, in which the HXK2 protein activity is decreased, compared to the parent cell.

HXK2 protein may be hexokinase isoenzyme 2. HXK2 protein may be an enzyme belonging to EC. 2.7.1.1. HXK2 protein may have a sequence identity of 75% or more, 80% or more, 85% or more, 90% or more, 95% or more, 96% or more, 97% or more, 98% or more, 99% or more, or 100% to an amino acid sequence of SEQ ID NO. 3, or a yeast homologue thereof. HXK2 protein may be encoded by a polynucleotide sequence of SEQ ID NO. 4. HXK2 gene may have a sequence identity of 75% or more, 80% or more, 85% or more, 90% or more, 95% or more, 96% or more, 97% or more, 98% or more, 99% or more, or 100% to a polynucleotide sequence encoding the amino acid of SEQ ID NO. 3. HXK2 may have a polynucleotide sequence of SEQ ID NO. 4.

In the yeast cell, the endogenous gene encoding HXK2 protein may be disrupted. In the yeast cell, the endogenous gene encoding HXK2 protein may be disrupted so that its expression is low enough to decrease the HXK2 protein activity, compared to its parent cell.

The yeast cell may have an ability to consume glucose at an increased glucose consumption rate, compared to the parent cell. The glucose consumption may be a process of forming two molecules of pyruvic acid from one molecule of glucose via glycolysis. The yeast cell may have an increased ability to produce a glycolytic intermediate or a glycolytic intermediate-derived substance, compared to a non-genetically engineered cell or a parent cell. The production may be production of a glycolytic intermediate or a glycolytic intermediate-derived substance within cells or secretion of a glycolytic intermediate or a glycolytic intermediate-derived substance after production within cells.

As used herein, the term "derived substance" may be a substance formed from a particular substance by a biosynthetic process. The "glycolytic intermediate-derived substance" may be included in the glycolytic intermediate. And, for example, the glycolytic intermediate-derived substance may be a substance formed from a pyruvate, by a biosynthetic process. The "biosynthetic process" includes a biosynthetic process that naturally exists in cells as well as a biosynthetic process that is newly created by introduction of a foreign gene. Specifically, the glycolytic intermediate may be glucose-6-phosphate (G6P), fructose-6-phosphate (F6P), fructose-1,6-bisphosphate (FBP), dihydroxyacetone phosphate (DHAP), glyceraldehyde-3-phosphate (GAP), 1,3-bisphosphoglycerate, 3-phosphoglycerate, 2-phosphoglycerate, phosphoenolpyruvate (PEP), or pyruvate. The glycolytic intermediate-derived substance may be a DHAP-derived substance, a glyceraldehyde-3-phosphate (GAP)-derived substance, or a pyruvate-derived substance. The "DHAP-derived substance" may be glycerol-3-phosphate (G3P), glycerol, a glycerol-derived product, or a combination thereof. The "pyruvate-derived substance" may be alcohol, organic acid, or a combination thereof. The "pyruvate-derived substance" may be ethanol, acetic acid, acetyl-CoA, lactate, a TCA cycle intermediate, a product derived therefrom, or a combination thereof. The TCA cycle intermediate may be citric acid, itaconic acid, isocitrate, oxalosuccinate, alpha-ketoglutarate, succinic acid, succinyl-CoA, fumaric acid, malate, oxaloacetate, or a combination thereof. The substance derived from the TCA cycle intermediate may be a substance derived from succinic acid. The substance derived from the TCA cycle intermediate may be succinyl-CoA, succinic semialdehyde (SSA), 4-hydroxybutyrate, 4-hydroxybutyryl-CoA, 4-hydroxybutylaldehyde, 1,3-butanediol (1,3-BDO), 1,4-butanediol (1,4-BDO), butanol, or isobutanol. The yeast cell may include a gene encoding an enzyme that functions to convert succinic acid to 1,4-BDO. The enzyme may be exemplified by CoA-dependent succinate semialdehyde dehydrogenase, 4-hydroxybutyrate (4-HB) dehydrogenase, 4-hydroxybutyryl-CoA (4HB-CoA) transferase, aldehyde/alcohol dehydrogenase, and *Clostridium acetobutylicum* AdhE2.

The yeast cell may be a strain belonging to *Saccharomyces, Zygosaccharomyces, Pichia, Kluyveromyces, Candida, Shizosaccharomyces, Issachenkia,* or *Hansenula,* for example, *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. ellipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), or *Saccharomyces zonatus* (*S. zonatus*).

The yeast cell may have an increased activity of an enzyme that exists in a synthetic pathway of a pyruvate-derived substance from pyruvate, a synthetic pathway of glycerol from DHAP, or a synthetic pathway of a glycerol-derived substance from glycerol. The synthetic pathway of glycerol from DHAP may include G3P dehydrogenase (GPDH) that catalyzes conversion of DHAP and NADH to G3P and NAD+, and G3Pase that catalyzes conversion of G3P to glycerol and Pi.

The "pyruvate-derived substance" is the same as described above. The increase may be caused by an increase in expression of a polynucleotide encoding the enzyme. The yeast cell may have an increased activity of an enzyme that converts pyruvate to lactate, or an increased activity of an enzyme that converts pyruvate to ethanol. The increase may be caused by an increase in expression of a polynucleotide that encodes the enzyme converting pyruvate to lactate or the enzyme converting pyruvate to ethanol. The polynucleotide that encodes the enzyme converting pyruvate to lactate may be a polynucleotide encoding an enzyme classified as EC 1.1.1.27 or EC 1.1.1.28. The enzyme in the pathway of converting pyruvate to ethanol may be one or more of pyruvate decarboxylase and alcohol dehydrogenase. The pyruvate decarboxylase may be an enzyme classified as EC 4.1.1.1. The alcohol dehydrogenase (ADH) may be an enzyme classified as EC. 1.1.1.2.

In the above aspect, the enzyme that catalyzes the conversion of pyruvate to lactate may be lactate dehydrogenase (LDH) belonging to EC 1.1.2.27 or EC 1.1.1.28. The LDH may be NAD(P)H-dependent. Further, LDH may act on D-lactate and/or L-lactate. The LDH may have a sequence identity of 95% or more to an amino acid sequence of SEQ ID NO. 5. SEQ ID NO. 5 represents LDH of *Pelodiscus sinensis japonicus*.

The yeast cell may include an exogenous gene encoding an enzyme that catalyzes conversion of pyruvate to lactate. The exogenous LDH gene may be expressed enough to increase the activity of the enzyme that catalyzes conversion of pyruvate to lactate, compared to its parent cell. The exogenous LDH gene may code for an amino acid sequence having a sequence identity of 95% or more to the amino acid sequence of SEQ ID NO. 5. The exogenous LDH gene may have a sequence identity of 95% or more to a nucleotide sequence of SEQ ID NO. 6. The LDH exogenous gene may have a sequence, which is changed to have codons suitable for expression in the yeast cell, or a sequence having optimized codons. This codon alteration may be properly performed within the range of causing no change in the amino acid sequence of the protein. SEQ ID NO. 6 represents LDH gene of *Pelodiscus sinensis japonicus*.

The exogenous LDH gene may be included in the genome of a cell. The exogenous LDH gene may code for an enzyme that acts on L-Ldh, D-Ldh or both of them. Therefore, the yeast cell may produce L-lactic acid or D-lactic acid or a racemic mixture thereof, or a salt thereof. The exogenous LDH gene may include those derived from bacteria, yeasts, fungi, and animals, for example, rodents, mammals, amphibians and *Sauropsida*. The exogenous LDH gene may be a polynucleotide encoding one or more of LDH selected from the *Pelodiscus sinensis japonicus, Ornithorhynchus anatinus, Tursiops truncatus, Rattus norvegicus,* or *Xenopus laevis*. The lactate dehydrogenase derived from *Pelodiscus sinensis japonicus, Ornithorhynchus anatinus, Tursiops truncatus, Rattus norvegicus,* or *Xenopus laevis* may have an amino acid sequence of SEQ ID NO. 5, 7, 8, or 9, respectively. The lactate dehydrogenase may have a sequence identity of 75% or more, 80% or more, 85% or more, 90% or more, 95% or more, 96% or more, 97% or more, 98% or more, 99% or more, or 100% to the amino acid sequence of SEQ ID NO. 5, 7, 8, or 9, respectively. The gene encoding the lactate dehydrogenase may have a sequence identity of 75% or more, 80% or more, 85% or more, 90% or more, 95% or more, 96% or more, 97% or more, 98% or more, 99% or more, or 100% to a nucleotide sequence of SEQ ID NO. 6, 10, 11, or 12.

The exogenous LDH gene may be expressed from a vector including the same. The vector may include a replication origin, a promoter, a polynucleotide encoding LDH, and a terminator. The replication origin may include a yeast autonomous replication sequence (ARS). The yeast ARS may be stabilized by a yeast centrometric sequence (CEN). The promoter may be selected from the group consisting of a CCW12 promoter, a CYC promoter, a TEF1 promoter, a PGK1 promoter, a GPD promoter, and an ADH promoter. The CCW12 promoter, CYC promoter, TEF1 promoter, PGK1 promoter, GPD promoter, or ADH promoter may have A polynucleotide sequence of SEQ ID NO. 13, 14, 15, 16, 17, or 18, respectively. The terminator may be selected from the group consisting of PGK1, CYC1, and GAL1. The CYC1 terminator may have a polynucleotide sequence of SEQ ID NO. 19. The vector may further include a selection marker.

The yeast cell may include one copy or multiple copies of an LDH gene, for example, about 2 to about 10 copies. The yeast cell may include, for example, about 1 to about 10, about 1 to about 8, about 1 to about 7, about 1 to about 6, about 1 to about 5, about 1 to about 4, 1 about to about 3, about 2 to 1 about 0, about 2 to about 8, about 2 to about 7, about 2 to about 6, about 2 to about 5, about 2 to about 4, or about 2 to about 3 copies of LDH gene(s). If the yeast cell includes multiple LDH genes, each of the genes may include copies of the same gene or copies of two or more different LDH genes. The multiple copies of exogenous LDH genes may be included in the same locus or multiple loci in the genome of a host cell.

An example of the yeast cell may be a yeast cell having an ability to produce lactate, in which RGT1 gene is disrupted and the exogenous gene encoding the enzyme (LDH) that catalyzes the conversion of pyruvate to lactate is included, compared to the parent cell.

Another example of the yeast cell may be a yeast cell having an ability to produce lactate, in which RGT1 gene and HXK2 gene are disrupted and the exogenous gene encoding the enzyme (LDH) that catalyzes the conversion of pyruvate to lactate is included, compared to the parent cell.

In the above aspect, the yeast cell may further include a genetic modification of decreasing an activity of an enzyme that catalyzes conversion of acetaldehyde to ethanol, and therefore, the yeast cell has a decreased activity of the enzyme that catalyzes conversion of acetaldehyde to ethanol.

The enzyme that catalyzes the conversion of acetaldehyde to ethanol may be ADH belonging to EC 1.1.1.1. Examples of ADH may include ADH1, ADH2, ADH3, ADH4, ADH5, ADH6, and ADH7. The ADH may be NADH-dependent. The ADH1 gene and ADH1 protein may have a polynucleotide sequence of SEQ ID NO. 20 and an amino acid sequence of SEQ ID NO. 21, respectively.

In the yeast cell, an endogenous gene encoding the enzyme that catalyzes conversion of acetaldehyde to ethanol may be disrupted. In the yeast cell, the gene may be disrupted so that its expression is low enough to decrease the activity of the enzyme that catalyzes conversion of acetaldehyde to ethanol, compared to its parent cell.

The yeast cell according to the above aspect may further include a genetic modification of decreasing an activity of an enzyme that catalyzes the conversion of pyruvate to acetaldehyde, an enzyme that catalyzes the conversion of lactate to pyruvate, an enzyme that catalyzes the conversion of DHAP to G3P, an enzyme that catalyzes the conversion of G3P to glycerol, an enzyme that catalyzes the conversion of acetaldehyde to acetate, or a combination thereof.

In the yeast cell, the enzyme that catalyzes the conversion of pyruvate to acetaldehyde may belong to EC 4.1.1.1, the enzyme that catalyzes the conversion of lactate to pyruvate may belong to EC 1.1.2.4 or EC 1.1.2.3, the enzyme that catalyzes the conversion of DHAP to G3P may belong to EC 1.1.1.8, the enzyme that catalyzes the conversion of G3P to glycerol may belong to EC 3.1.3.21, and the enzyme that catalyzes the conversion of acetaldehyde to acetate may belong to EC 1.2.1.3, EC 1.2.1.4, or EC 1.2.1.5.

In the yeast cell, a gene encoding the enzyme that catalyzes the conversion of pyruvate to acetaldehyde, a gene encoding the enzyme that catalyzes the conversion of lactate to pyruvate, a gene encoding the enzyme that catalyzes the conversion of DHAP to G3P, a gene encoding the enzyme that catalyzes the conversion of G3P to glycerol, a gene encoding the enzyme that catalyzes the conversion of acetaldehyde to acetate, or a combination thereof may be disrupted.

The enzyme that catalyzes the conversion of pyruvate to acetaldehyde may be pyruvate decarboxylase (PDC). PDC may have a sequence identity of 75% or more, 80% or more, 85% or more, 90% or more, 95% or more, 96% or more, 97% or more, 98% or more, 99% or more, or 100% to an amino acid sequence of SEQ ID NO. 22. The PDC gene may have a sequence identity of 75% or more, 80% or more, 85% or more, 90% or more, 95% or more, 96% or more, 97% or more, 98% or more, 99% or more, or 100% to a polynucleotide sequence of SEQ ID NO. 23. The PDC includes PDC1 (SEQ ID NO. 23), PDC5, and PDC6. The PDC may catalyze conversion of pyruvate to acetaldehyde under anaerobic or aerobic conditions. The PDC gene may be disrupted by replacement with LDH gene. In the yeast cell, the PDC gene may be attenuated. In the yeast cell, one or more of PDC1 gene, PDC5 gene, and PDC6 gene may be also attenuated. In the yeast cell, the gene(s) encoding one or two of PDC1, PDC5, and PDC6 may be inactivated. For example, PDC1 gene, PDC5 gene, PDC6 gene, PDC1 gene and PDC5 gene, PDC1 gene and PDC6 gene, or PDC5 gene and PDC6 gene may be inactivated.

The enzyme that catalyzes the conversion of lactate to pyruvate may be lactate cytochrome-c oxidoreductase (CYB2). The enzyme that catalyzes the conversion of lactate to pyruvate may be cytochrome c-dependent. The CYB2 may belong to EC 1.1.2.4 which acts on D-lactate, or EC 1.1.2.3 which acts on L-lactate. The enzyme that catalyzes the conversion of lactate to pyruvate may have a sequence identity of 75% or more, 80% or more, 85% or more, 90% or more, 95% or more, 96% or more, 97% or more, 98% or more, 99% or more, or 100% to an amino acid sequence of SEQ ID NO. 24. A gene that codes for the enzyme that catalyzes the conversion of lactate to pyruvate may have a sequence identity of 75% or more, 80% or more, 85% or more, 90% or more, 95% or more, 96% or more, 97% or more, 98% or more, 99% or more, or 100% to a polynucleotide sequence of SEQ ID NO. 25. The CYB2 gene may be disrupted by replacement with LDH gene.

The enzyme that catalyzes the conversion of DHAP to G3P may be NAD-dependent dependent glycerol-3-phosphate dehydrogenase (GPD). The GPD may be a $NAD^+$-dependent enzyme. An example of the GPD may include cytosolic glycerol-3-phosphate dehydrogenase, which is an enzyme catalyzing reduction of dehydroxyacetone phosphate (DHAP) to glycerol-3-phosphate using oxidation of NADH to NAD⁺. The GPD may belong to EC 1.1.1.8. Examples of the GPD include GPD1 and GPD2. The GPD may have a sequence identity of 75% or more, 80% or more, 85% or more, 90% or more, 95% or more, 96% or more, 97% or more, 98% or more, 99% or more, or 100% to an amino acid sequence of SEQ ID NO. 26. A gene encoding the GPD may have a sequence identity of 75% or more, 80% or more, 85% or more, 90% or more, 95% or more, 96% or more, 97% or more, 98% or more, 99% or more, or 100% to a polynucleotide sequence of SEQ ID NO. 27. The GPD gene may be disrupted by replacement with LDH gene.

The enzyme that catalyzes the conversion of glycerol-3-phosphate to glycerol may be glycerol phosphate phosphatase (GPP). The GPP may be GPP1 and GPP2 derived from *S. cerevisiae*. The GPP may have a nucleotide sequence of SEQ ID NO. 28 and an amino acid sequence of SEQ ID NO. 29. The GPP gene may be disrupted by replacement with LDH gene.

The enzyme that catalyzes the conversion of acetaldehyde to acetate may be acetaldehyde dehydrogenase (ALD). The ALD may be NAD(P)⁺-dependent. The ALD may have a sequence identity of 75% or more, 80% or more, 85% or more, 90% or more, 95% or more, 96% or more, 97% or more, 98% or more, 99% or more, or 100% to an amino acid sequence of SEQ ID NO. 30. The ALD gene have a sequence identity of 75% or more, 80% or more, 85% or more, 90% or more, 95% or more, 96% or more, 97% or more, 98% or more, 99% or more, or 100% to a polynucleotide sequence of SEQ ID NO. 31. The ALD includes ALD6 (also called ALD1), ALD2, ALD3, ALD4, and ALD5. The ALD gene may be disrupted by replacement with LDH gene. In the yeast cell, the ALD gene may be attenuated. In the yeast cell, one or more of ALD6 gene, ALD2 gene, and ALD3 gene may be also attenuated. In the yeast cell, one or two of ALD6 gene, ALD2 gene, and ALD3 gene may be inactivated.

In the yeast cell, the enzyme that catalyzes the conversion of pyruvate to acetaldehyde may be PDC, the enzyme that catalyzes the conversion of lactate to pyruvate may be CYB2, the enzyme that catalyzes the conversion of DHAP to G3P may be NAD-dependent GPD, the enzyme that catalyzes the conversion of glycerol-3-phosphate to glycerol may be GPP, and the enzyme that catalyzes the conversion of acetaldehyde to acetate may be acetaldehyde dehydrogenase.

The yeast cell according to an aspect may have an increased activity of an enzyme that catalyzes the conversion of acetaldehyde to acetyl-CoA, compared to its parent cell.

The enzyme that catalyzes the conversion of acetaldehyde to acetyl-CoA may be acylating acetaldehyde dehydrogenase (A-ALD) belonging to EC 1.2.1.10.

A type of the enzyme that catalyzes the conversion of acetaldehyde to acetyl-CoA may be a part of a bifunctional aldolase-dehydrogenase complex involved in 4-hydroxy-2-ketovalerate catabolism. Such bifunctional enzyme catalyzes the final two steps of the meta-cleavage pathway for catechol, which is an intermediate in many bacterial species in the degradation of phenol, toluene, naphthalene, biphenyl and other aromatic compounds. 4-Hydroxy-2-ketovalerate is first converted by 4-hydroxy-2-ketovalerate aldolase to pyruvate and acetaldehyde, subsequently acetaldehyde is converted by ADA to acetyl-CoA. An example of this type of A-ALD is DmpF in *Pseudomonas* sp CF600 (Genbank No: CAA43226). MphF protein of *E. coli* is homologous to the DmpF protein. Another type thereof is a protein that catalyzes the reversible conversion of acetyl-CoA to acetaldehyde in strictly or facultative anaerobic microorganisms, but does not possess ADH activity. An example of this type of protein may be a protein that is reported in *Clostridium kluyveri*. A-ALD has been annotated in the genome of *Clostridium kluyveri* DSM 555 (GenBank No: EDK33116). A homologous protein AcdH was identified in the genome of *Lactobacillus plantarum* (GenBank No: NP-784141). Another example of this type of protein is a product of the gene in *Clostridium beijerinckii* NRRL B593 (Genbank No: AAD31841). An example of A-ALD may be *E. coli*-derived MhpF or a functional homologue thereof, for example, *E. coli* and *S. typhimurium*-derived EutE (e.g., EutE gene having a polynucleotide sequence of SEQ ID NO. 32 and EutE protein having an amino acid sequence of SEQ ID NO. 33), or *Pseudomonas* sp. CF600-derived dmpF. The A-ALD may be NAD(P)⁺-dependent. The A-ALD may have an activity of catalyzing the following reaction:

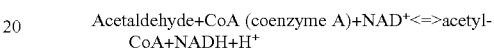

Acetaldehyde+CoA (coenzyme A)+NAD⁺<=>acetyl-CoA+NADH+H⁺

The A-ALD may be expressed without formation of a complex with other proteins. The yeast cell may not include, for example, an exogenous enzyme belonging to EC 4.1.3.39 or a gene thereof.

The A-ALD may be derived from *E. coli*. In *E. coli*, the A-ALD gene, namely, mhpF, may be one of the units consisting of the transcription units, mhpA, mhpB, mhpC, mhpD, mhpE, and mhpF. Generally, MhpE and MhpF exist as a complex in other microorganisms, but MhpF may exist singly and shows its activity in *E. coli*. In this regard, the enzyme MhpF, which catalyzes conversion of acetaldehyde to acetyl-CoA, may have a sequence identity of 95% or more to an amino acid sequence of SEQ ID NO. 34.

The yeast cell may include an exogenous gene encoding the enzyme that catalyzes the conversion of acetaldehyde to acetyl-CoA. In the yeast cell, the exogenous A-ALD gene may be expressed enough to increase the activity of the enzyme that catalyzes conversion of acetaldehyde to acetyl-CoA, compared to its parent cell. The exogenous A-ALD gene may code for an amino acid having a sequence identity of 95% or more to an amino acid sequence of SEQ ID NO. 34. The exogenous A-ALD gene may have a sequence identity of 95% or more to a nucleotide sequence of SEQ ID NO. 35 or SEQ ID NO. 36. SEQ ID NO. 35 represents a nucleotide sequence of the A-ALD gene derived from *E. coli*. The exogenous A-ALD gene may have a sequence, which is changed to have codons suitable for expression in the yeast cell, or a sequence having optimized codons. This codon alteration may be properly performed within the range of causing no change in the amino acid sequence of the protein. SEQ ID NO. 36 represents an example of the nucleotide sequence having yeast-optimized codons of the *E. coli*-derived A-ALD gene.

The exogenous gene may be introduced into the parent cell using an expression vector. Further, the exogenous gene may be introduced in the form of a linear polynucleotide into the parent cell. Furthermore, the exogenous gene may be expressed from the expression vector (e.g., plasmid) within the cell. For stable expression, the exogenous gene may be expressed by integration into a genetic material (e.g., chromosome) within the cell. The exogenous gene may be appropriately regulated by an exogenous promoter operably linked to the gene. The promoter may be a promoter derived from ccw12, pdc1, tef1 or pgk1 gene.

Another aspect provides a method of producing the yeast cell having an ability to produce lactate, the method including: introducing a gene encoding the enzyme that catalyzes conversion of pyruvate to lactate; and disrupting the gene encoding RGT1 protein in the yeast cell.

The method of producing the yeast cell having an ability to produce lactate may further include disrupting the gene encoding HXK2 protein in the yeast cell.

In the method of producing the yeast capable of producing lactate, introducing the yeast cell with the gene encoding the enzyme that catalyzes conversion of pyruvate to lactate is the same as follows: In this step, the "yeast cell", the "enzyme that catalyzes the conversion of pyruvate to lactate" and the "gene encoding the enzyme that catalyzes the conversion of pyruvate to lactate" are the same as described above.

The "gene encoding the enzyme that catalyzes the conversion of pyruvate to lactate" may be introduced to be integrated into an endogenous genetic material (e.g., chromosome) of the yeast cell. In this case, the genes are inserted into one or more positions of the particular gene of the endogenous genetic material (e.g., chromosome) of the yeast cell, resulting in disruption of the one or more genes. The particular gene may include the gene encoding the enzyme that catalyzes the conversion of pyruvate to acetaldehyde, the gene encoding the enzyme that catalyzes the conversion of lactate to pyruvate, the gene encoding the enzyme that catalyzes the conversion of DHAP to G3P, the gene encoding the enzyme that catalyzes the conversion of G3P to glycerol, and the gene encoding the enzyme that catalyzes the conversion of acetaldehyde to ethanol. The particular gene may include PDC, CYB2, GPD, GPP, and ADH genes.

The gene may exist within the yeast cell without integration into the endogenous genetic material of the yeast cell. In this case, the gene may be included in a vector such as a plasmid and may exist separately from the endogenous genetic material of the yeast cell.

The gene may be introduced in an expressible form into the yeast cell, and then expressed to produce its gene product, the "enzyme that catalyzes the conversion of pyruvate to lactate" in the yeast cell. The expressible form may be in the form of operably linking the gene to its expression regulatory sequence. For example, the gene may be operably linked to one or more of an exogenous enhancer, operator, promoter, and transcription terminator, and thus, it may become expressible as it is in the yeast cell, or it may be linked to a regulatory sequence of the yeast cell to be expressible. The promoter may be selected from the group consisting of a CCW12 promoter, a CYC promoter, a TEF1 promoter, a PGK1 promoter, a GPD promoter, and an ADH promoter. The CCW12 promoter, CYC promoter, TEF1 promoter, PGK1 promoter, GPD promoter, and ADH promoter may have the polynucleotide sequence of SEQ ID NOs. 13, 14, 15, 16, 17, and 18, respectively. The terminator may be selected from the group consisting of phosphoglycerate kinase 1 (PGK1), cytochrome c transcription (CYC1), and GAL1. The CYC1 terminator may have a nucleotide sequence of SEQ ID NO. 19. The vector may further include a selection marker.

The introducing may be performed by introducing a genetic material into a yeast cell known in the art (R. Danile Gietz et al., Biotechniques 30:816-831, April 2001). The introducing method may include a spheroplast method, intact yeast cell transformation, and electroporation. In the intact yeast cell transformation, specific monovalent alkali cations ($Na^+$, $K^+$, $Rb^+$, $Cs^+$ and $Li^+$) may be used in combination with PEG to stimulate plasmid DNA uptake by intact yeast cells. For example, heat shock may be applied to an aqueous solution containing PEG, LiAc, carrier ssDNA, and plasmid DNA. Electroporation may involve applying an electric pulse to a mixed medium containing the yeast cell and DNA such as plasmid DNA.

Therefore, the introducing step may include contacting the yeast cell with the gene encoding the enzyme that catalyzes the conversion of pyruvate to lactate in an appropriate liquid medium. The yeast cell may be a spheroplast, or an intact yeast cell. The liquid medium may differ depending on the selected transformation method. The liquid medium may be, for example, water, an aqueous solution, or a buffer. The aqueous medium may include monovalent alkali cations (one or more of $Na^+$, $K^+$, $Rb^+$, $Cs^+$ and $Li^+$) and PEG. The aqueous medium may include carrier ssDNA. The aqueous medium may be an aqueous solution containing PEG, LiAc, and carrier ssDNA.

The contacting may be performed by applying heat shock or electric pulse to the yeast cell and the gene. The heat shock may be incubation at about 40 to about 45° C., for example, about 42° C. The electric pulse may be applied either in an electroporation cuvette or between electrodes in a petri dish. The parameters of the electroporation, field strength (kV/cm), capacitance (uF), and resistance may differ depending on details of cell preparation. Therefore, transformation efficiency may vary depending on the yeast strain. For any given yeast strain, those skilled in the art investigate the parameters of the pulse according to the cell and select proper parameters to obtain a sufficient number of transformants.

In the introducing, the both genes are included in a vector, together with a homologous sequence to an endogenous genetic material of the parent yeast cell. The homologous sequence is complementary to a target sequence which is present in the endogenous genetic material of the parent yeast cell, and thus it may be substituted for the target sequence by homologous recombination. The target sequence includes the gene encoding the enzyme that catalyzes conversion of pyruvate to acetaldehyde, the gene encoding the enzyme that catalyzes conversion of lactate to pyruvate, the gene encoding the enzyme that catalyzes conversion of DHAP to G3P, the gene encoding the enzyme that catalyzes conversion of G3P to glycerol, and the gene encoding the enzyme that catalyzes conversion of acetaldehyde to ethanol. The particular gene includes PDC, CYB2, GPD, GPP, and ADH genes. The vector may include two sequences that are homologous to the 5'-terminal region and the 3'-terminal region of the target sequence, respectively. In this case, the introducing may include incubation of the yeast cell under a selection pressure during or after the contacting. The selection pressure refers to a substance or state that is forced to select only the cells in which a homologous recombination occurs. The selection pressure includes incubation in the presence of an antibiotic. In this case, the vector may include a gene encoding an enzyme that degrades the antibiotic.

In the method of producing the yeast capable of producing lactate, disrupting the respective gene(s) encoding RGT1 protein or RGT1 protein and HXK2 protein in the yeast cells is the same as follows:

The disrupting may include contacting the yeast cell with a polynucleotide including a homologous sequence to the gene encoding RGT1 protein, or the respective genes encoding RGT1 protein and HXK2 protein in an appropriate liquid medium. The homologous sequence may be homologous to the entire or a part of the gene. The homologous sequence may be homologous to a coding region or an expression regulatory region of the gene. The polynucleotide including the homologous sequence to the gene may be linked to other genes, for example, a gene encoding the enzyme that is involved in biosynthesis of lactate, such as an LDH gene. The polynucleotide including the homologous sequence to the gene may be included in a vector such as a plasmid. The homologous sequence may be used for replacement of the respective gene(s) encoding RGT1 protein or RGT1 protein and HXK2 protein by homologous recombination. The vector may include two sequences that are homologous to the 5'-terminal region and the 3'-terminal region of the target sequence, respectively. In this case, the disrupting may include incubation of the yeast cell under a selection pressure during or after the contacting. The selection pressure refers to a substance or state that provides for the selection of only those cells in which a homologous recombination occurs. The selection pressure includes incubation in the presence of an antibiotic. In this case, the vector may include a gene encoding an enzyme that degrades the antibiotic.

In the disrupting, the contacting may be performed under the same conditions as a method of introducing a genetic material into a yeast cell, which is known in the art, unless otherwise specified. The introduction method may include a spheroplast method, intact yeast cell transformation, and electroporation. In the intact yeast cell transformation, specific monovalent alkali cations ($Na^+$, $K^+$, $Rb^+$, $Cs^+$, and $Li^+$) may be used in combination with PEG to stimulate plasmid DNA uptake by intact yeast cells. For example, heat shock may be applied to an aqueous solution containing PEG, LiAc, carrier ssDNA, and plasmid DNA. Electroporation may involve applying an electric pulse to a mixed medium containing the yeast cell and DNA such as plasmid DNA.

The yeast cell may be a spheroplast or an intact yeast cell. The liquid medium may differ depending on the selected transformation method. The liquid medium may be, for example, water, an aqueous solution, or a buffer. The aqueous medium may include monovalent alkali cations (one or more of $Na^+$, $K^+$, $Rb^+$, $Cs^+$, and $Li^+$) and PEG. The aqueous medium may include carrier ssDNA. The aqueous medium may be an aqueous solution containing PEG, LiAc, and carrier ssDNA.

The contacting may be performed by applying heat shock or electric pulse to the yeast cell and the gene. The heat shock may be incubation at about 40 to about 45° C., for example, about 42° C. The electric pulse may be applied either in an electroporation cuvette or between electrodes in a petri dish. The parameters of the electroporation, field strength (kV/cm), capacitance (uF), and resistance may differ depending on details of cell preparation. Therefore, transformation efficiency may vary depending on the yeast strain. For any given yeast strain, those skilled in the art investigate the parameters of the pulse according to the cell and select proper parameters to obtain a sufficient number of transformants.

In the contacting, the respective genes are included in a vector, together with a homologous sequence to an endogenous genetic material of the parent yeast cell. The homologous sequence is complementary to a target sequence which is present in the endogenous genetic material of the parent yeast cell, and thus, it may be substituted for the target sequence by homologous recombination. The target sequence includes the respective gene(s) encoding RGT1 protein or RGT1 protein and HXK2 protein. Further, the target sequence includes the gene encoding the enzyme that catalyzes conversion of pyruvate to acetaldehyde, the gene encoding the enzyme that catalyzes conversion of lactate to pyruvate, the gene encoding the enzyme that catalyzes conversion of DHAP to G3P, the gene encoding the enzyme that catalyzes conversion of glycerol-3-phosphate to glycerol, and the gene encoding the enzyme that catalyzes conversion of acetaldehyde to ethanol. The particular gene includes PDC, CYB2, GPD, GPP, and ADH genes. The vector may include two sequences that are homologous to the 5'-terminal region and the 3'-terminal region of the target sequence, respectively. In this case, incubation of the yeast cell under a selection pressure during or after the contacting may be included. The selection pressure refers to a substance or state that is forced to select only the cells in which a homologous recombination occurs. The selection pressure includes incubation in the presence of an antibiotic. In this case, the vector may include a gene encoding an enzyme that degrades the antibiotic.

Still another aspect provides a method of producing the glycolytic intermediate or the glycolytic intermediate-derived substance, the method including: culturing the yeast cell in a cell culture medium to obtain a culture, whereby the yeast cell produces the glycolytic intermediate or the glycolytic intermediate-derived substance; and recovering the glycolytic intermediate or the glycolytic intermediate-derived substance from the culture.

This method includes culturing the yeast cell. The "yeast cell" is the same as described above.

The culturing may be performed in a medium containing a carbon source, for example, glucose. The medium used for culturing the yeast cell may be any general medium that is suitable for host cell growth, such as a minimal or complex medium containing proper supplements. The suitable medium may be commercially available or prepared by a known preparation method. The medium used for the culturing may be a medium that satisfies the requirements of a particular yeast cell. The medium may be a medium selected from the group consisting of a carbon source, a nitrogen source, a salt, trace elements and combinations thereof.

The culturing conditions may be properly controlled in order to obtain the glycolytic intermediate or the glycolytic intermediate-derived substance, for example, a pyruvate-derived substance such as pyruvate or lactate from the genetically engineered yeast cell. For proliferation, the cell may be cultured under aerobic conditions. Thereafter, the cell may be cultured under microaerobic conditions or anaerobic conditions in order to produce the glycolytic intermediate or the glycolytic intermediate-derived substance. The term "anaerobic conditions" means oxygen deficient conditions. The term "microaerobic conditions", when used in reference to culture or growth conditions, means that a concentration of dissolved oxygen (DO) in a medium is more than 0% and less than about 10% of saturation for DO in a liquid medium. The microaerobic conditions also include growing or resting cells in a liquid medium or on a solid agar plate inside a sealed chamber which is maintained with an atmosphere of less than 1% oxygen. The percentage of oxygen may be maintained by, for example, sparging the culture with an $N_2/CO_2$ mixture or other suitable non-oxygen gas. The oxygen conditions include maintaining the concentration of DO at about 0% to about 10%, for example, about 0 to about 8%, about 0 to about 6%, about 0 to 4%, or about 0 to about 2%.

The term "culture conditions" means conditions for culturing the yeast cell. Such culture conditions may include, for example, a carbon source, a nitrogen source, or an oxygen condition utilized by the yeast cell. The carbon source may be an assimilable carbon source that can be assimilated by any yeast cell. The carbon source may include monosaccharides, disaccharides, or polysaccharides. The carbon source may be glucose, fructose, mannose, or galactose. The nitrogen source that can be utilized by the yeast cell may be an organic nitrogen compound or an inorganic nitrogen compound. The nitrogen source may be exemplified by amino acids, amides, amines, nitrates, or ammonium salts.

The medium may include a buffering agent that maintains a pH at about 3 to about 5. The buffering agent may be bicarbonate. The culturing may be performed by maintaining a pH of the medium at about 3 to about 5. The pH of the medium may be maintained at about 3 to about 5 by including the buffering agent in the medium or by adding an acid or a base to the medium during the culturing. For example, by monitoring the pH of the medium, a acid is added to the medium at a pH that is higher than about 5, and an base is added to the medium at a pH that is lower than about 3.

The culture may include the glycolytic intermediate or the glycolytic intermediate-derived substance, for example, the pyruvate-derived substance such as pyruvate or lactate.

Isolation of the glycolytic intermediate or the glycolytic intermediate-derived substance, for example, the pyruvate-derived substance such as pyruvate or lactate, from the culture may be performed by a general method known in the art. Such isolation method may be centrifugation, filtration, ion chromatography, or crystallization. For example, the culture is centrifuged at a low speed to remove biomass, and a resulting supernatant is subjected to ion chromatography for isolation.

The recombinant yeast cell according to an aspect is able to effectively produce the glycolytic intermediate or the glycolytic intermediate-derived substance.

The method of producing the recombinant yeast cell according to another aspect is used to effectively produce the glycolytic intermediate or the glycolytic intermediate-derived substance.

The method of effectively producing the glycolytic intermediate or the glycolytic intermediate-derived substance according to still another aspect is used to effectively produce the glycolytic intermediate or the glycolytic intermediate-derived substance by the recombinant yeast cell.

Hereinafter, the present invention will be described in more detail with reference to the exemplary embodiments. However, the exemplary embodiments described herein should be considered in a descriptive sense only and not for purposes of limitation.

Example 1: Production of Lactate from RGT1 Gene-Disrupted Yeast Strain

1. Preparation of Strain

S. cerevisiae strain used in this Example is prepared as follows:

(1) Preparation of S. cerevisiae CEN.PK2-1D (Δadh1::ldh)

(1.1) Preparation of adh1 Gene Deletion Cassette

In order to prepare an 'ldh cassette'-containing vector, PCR is performed using genomic DNA of S. cerevisiae CEN.PK2-1D as a template and a primer set of SEQ ID NOs. 37 and 38 as primers to amplify a CCW12 gene promoter (hereinafter, referred to as "P CCW12" or "CCW12 promoter"), and amplification products of the CCW12 gene promoter (SEQ ID NO. 13) and a synthesized ldh gene (SEQ ID NO. 6) (DNA2.0 Inc., USA) are cleaved with SacI/XbaI and BamHI/SalI, respectively and ligated with a pRS416 vector (ATCC87521TM), which is cleaved with the same enzymes, respectively. The pRS416 vector is a yeast centromere shuttle plasmid having a T7 promoter, an ampicillin resistance in bacteria, a URA3 cassette in yeast (selection marker), and restriction enzyme cloning sites.

Figure 2:
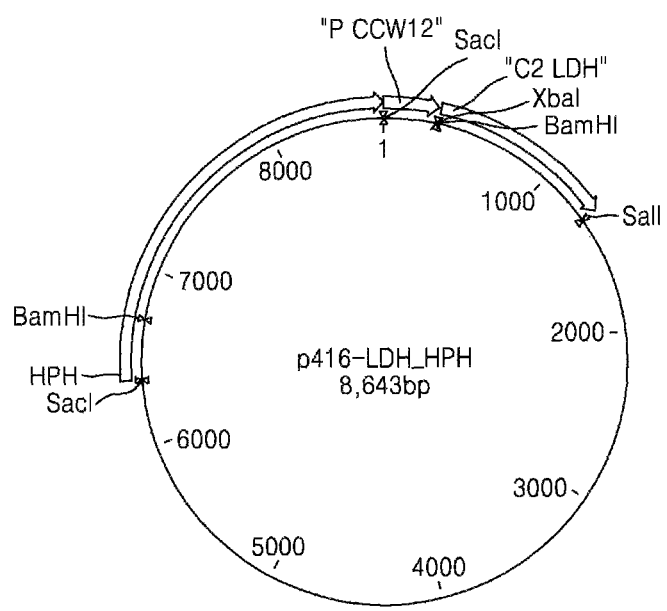
FIG. 2 shows a cleavage map of a p416-CCW12-LD-H_HPH vector.

Further, PCR is performed using a pCEP4 plasmid (invitrogen, Cat. no. V044-50) as a template and a primer set of SEQ ID NOs. 39 and 40 as primers to amplify an "HPH cassette" sequence (SEQ ID NO. 41). The amplified "HPH cassette" and the pRS416 vector are cleaved with SacI enzyme, and ligated with each other so as to prepare a p416-ldh-HPH vector containing a structure of operably linking the 'ldh cassette' and the "HPH cassette". FIG. 2 shows a cleavage map of the p416-ldh-HPH vector. In FIG. 2, "P CCW12" and "C2 LDH" indicate the CCW12 promoter and LDH orf, respectively. The pCEP4 plasmid is an episomal mammalian expression vector that uses the cytomegalovirus (CMV) immediate early enhancer/promoter for high level transcription of recombinant genes inserted into the multiple cloning site. pCEP4 has a hygromycin B resistance gene for stable selection in transfected cells. Here, the 'ldh cassette' represents a region that allows the ldh gene to be expressed, because it contains the ldh gene and its regulatory region. Transcription of the ldh gene is allowed in the presence of the CCW12 promoter. Further, the 'HPH (hygromycin B phosphotransferase) cassette' represents a region that allows the hygromycin B resistance gene to be expressed, because it contains the hygromycin B resistance gene and its regulatory region.

An adh1 deletion cassette is prepared by PCR using the p416-ldh-HPH vector as a template and a primer set of SEQ ID NO. 42 and SEQ ID NO. 43 as primers. In SEQ ID NO. 42 and SEQ ID NO. 43, the sequence at position 1-51 represents a region which is substituted for the adh1 gene by homologous recombination with a homologous sequence in a genome of S. cerevisiae.

The adh1 deletion cassette is further used for adh1 inactivation and ldh gene introduction by replacement of the ADH (adh1)-encoding gene with the ldh-HPH cassette in the genome of S. cerevisiae CEN.PK2-1D.

(1.2) Preparation of S. cerevisiae CEN.PK2-1D (Δadh1::ldh)

In order to replace the adh1 gene with the ldh gene in S. cerevisiae CEN.PK2-1D, the "adh1 deletion cassette" prepared in (1.1.2) is introduced into S. cerevisiae CEN.PK2-1D strain by heat shock transformation, and cultured in an YPD medium (Yeast extract 1 (w/v) %, peptone 1 (w/v) %, and glucose 2 (w/v) %) containing 200 ug/mL of hygromycin at 30° C. for 3 days for replacement of the chromosomal adh1 gene with the ldh gene, thereby preparing a S. cerevisiae CEN.PK2-1D (Δadh1::ldh) strain).

(2) Preparation of S. cerevisiae CEN.PK2-1D (Δadh1::ldh, Δpdc1::ldh, Δcyb2::ldh, Δgpd1::ldh) Strain (2.1) Construction of Vector for pdc1, cyb2, and gpd1 Deletions To prepare a pyruvate decarboxylase 1 (Pdc1) deletion cassette, PCR is performed using p416-ldh-HPH as a template and a primer set of SEQ ID NOs. 44 and 45 as primers, and an amplification product is cleaved with SacI and ligated with a pUC57-Ura3HA vector (DNA2.0 Inc.: SEQ ID NO. 46) which is cleaved with the same enzyme, so as to prepare pUC57-ura3HA-ldh. Next, PCR is performed using pUC57-ura3HA-ldh as a template and a primer set of SEQ ID NOs. 47 and 48 as primers so as to prepare a pdc1 deletion cassette. In SEQ ID NO. 47 and SEQ ID NO. 48, each of the sequences at positions 1-42 and 1-44 represents a region which is substituted for the pdc1 gene by homologous recombination with a homologous sequence of S. cerevisiae.

Further, L-lactate cytochrome-c oxidoreductase (cyb2) gene deletion cassette is amplified by PCR using the deletion vector pUC57-ura3HA-ldh as a template and a primer set of SEQ ID NOs. 49 and 50 as primers. In SEQ ID NO. 49 and SEQ ID NO. 50, the sequence at position 1-45 represents a region which is substituted for the cyb2 gene by homologous recombination with a homologous sequence of *S. cerevisiae*.

Further, a glycerol-3-phosphate dehydrogenase (gpd1) gene deletion cassette is amplified by PCR using the deletion vector pUC57-ura3HA-ldh as a template and a primer set of SEQ ID NOs. 51 and 52 as primers. In SEQ ID NO. 52, the sequence at position 1-50 represents a region which is substituted for the gpd1 gene by homologous recombination with a homologous sequence of a chromosome of *S. cerevisiae*.

(2.2) Preparation of *S. cerevisiae* CEN.PK2-1D (Δadh1::ldh, Δpdc1::ldh, Δcyb2::ldh, Δgpd1::ldh) Strain First, in order to replace the pdc1 gene with the ldh gene in *S. cerevisiae* CEN.PK2-1D (Δadh1::ldh), the "pdc1 deletion cassette" prepared in (2.1) is introduced into *S. cerevisiae* CEN.PK2-1D (Δadh1::ldh) prepared in (1) by heat shock transformation. After heat shock, the cells are cultured in a Ura-drop out medium as a selection marker at 30° C. for 3 days to replace the chromosomal pdc1 gene with the ldh gene. For genotyping of the prepared strain, PCR is performed using a genome of the prepared strain as a template and a primer set of SEQ ID NOs. 53 and 54 to examine deletion of the pdc1 gene.

As a result, *S. cerevisiae* CEN.PK2-1D (Δadh1::ldh, Δpdc1::ldh) strain is identified.

Next, to replace the cyb2 gene with the ldh gene in *S. cerevisiae* CEN.PK2-1D (Δadh1::ldh, Δpdc1::ldh) strain, the "cyb2 deletion cassette" prepared in (2.1) is introduced into the strain by heat shock transformation. After heat shock, the cells are cultured in a Ura-drop out medium as a selection marker at 30° C. for 3 days to replace the chromosomal cyb2 gene with the ldh gene. For genotyping of the prepared strain, PCR is performed using a genome of the prepared strain as a template and a primer set of SEQ ID NOs. 55 and 56 to examine deletion of the cyb2 gene.

As a result, *S. cerevisiae* CEN.PK2-1D (Δadh1::ldh, Δpdc1::ldh, Δcyb2::ldh) strain is identified.

Next, to replace the gpd1 gene with the ldh in *S. cerevisiae* CEN.PK2-1D (Δadh1::ldh, Δpdc1::ldh, Δcyb2::ldh) strain, the "gpd1 deletion cassette" prepared in (2.1) is introduced into the strain by heat shock transformation. After heat shock, the cells are cultured in a Ura-drop out medium as a selection marker at 30° C. for 3 days to replace the chromosomal gpd1 gene with the ldh gene. For genotyping of the prepared strain, PCR is performed using a genome of the prepared strain as a template and a primer set of SEQ ID NOs. 57 and 58 to examine deletion of the gpd1 gene.

As a result, *S. cerevisiae* CEN.PK2-1D (Δadh1::ldh, Δpdc1::ldh, Δcyb2::ldh, Δgpd1::ldh) strain is identified.

(3) Preparation of *S. cerevisiae* CEN.PK2-1D (Δadh1::ldh, Δpdc1::ldh, Δcyb2::ldh, Δgpd1::ldh, mhpF, Δald6, EutE) Strain (3.1) Construction and Introduction of Vector for mhpF Insertion To enhance a pathway of converting acetaldehyde to acetyl-CoA in *S. cerevisiae* CEN.PK2-1D (Δadh1::ldh, Δpdc1::ldh, Δcyb2::ldh, Δgpd1::ldh), an MhpF gene is inserted.

In detail, to express *E. coli*-derived MhpF gene (SEQ ID NO. 35) from a vector in *S. cerevisiae*, the MhpF gene (SEQ ID NO. 36) (DNA2.0 Inc., USA), which is codon-optimized for expression in *S. cerevisiae*, is synthesized. The synthesized MhpF gene has a TEF1 promoter sequence (SEQ ID NO. 15) at the 5' end, and its transcription is regulated by the TEF1 promoter. pJ1214-mhpF (DNA2.0 Inc., USA) containing this synthesized TEF1 promoter-MhpF gene is provided. pJ1214 (DNA2.0 Inc., USA) is an *S. cerevisiae* expression vector containing a URA3 marker and a 2 um Ori sequence. FIG. 1 shows a cleavage map of the pJ1214-mhpF vector. In FIG. 1, P TEF indicates the TEF promoter. A nucleotide sequence of the pJ1214-mhpF vector is represented by SEQ ID NO. 59.

The MhpF gene of pJ1214-mhpF and 'HIS3 cassette' are linked to 'pUC19 vector' (NEB, N3041) using a restriction enzyme SalI, so as to prepare a pUC19-His-MhpF vector (SEQ ID NO. 60). The HIS3 cassette is an amplification product which is obtained by PCR using pRS413 (ATCC8758) as a template and primers of SEQ ID NO. 61 and SEQ ID NO. 62. mhpF is expressed in the presence of GPD promoter from the pUC19-His-MhpF vector.

PCR is performed using the prepared pUC19-His-MhpF vector as a template and primers of SEQ ID NOs. 63 and 64 in which a leu2 homologous recombination sequence and a promoter are linked, so as to prepare a mhpF insertion cassette. Here, the leu2 homologous recombination sequence does not express a functional protein due to its mutation in the parent strain.

The mhpF insertion cassette thus prepared is introduced into *S. cerevisiae* CEN.PK2-1D (Δadh1::ldh, Δpdc1::ldh, Δcyb2::ldh, Δgpd1::ldh). Introduction is performed by general heat shock transformation, and after transformation, cells are cultured in a histidine drop out medium (Yeast nitrogen base without amino acids (Sigma-Aldrich: Cat. no. Y0626) 6.7 g/L, and Yeast synthetic drop-out without histidine (Sigma-Aldrich: Cat. no. Y1751) 1.9 g/L, glucose 2 (w/v) %) to replace the chromosomal Leu2 ORF with the cassette.

In order to examine introduction of the mhpF gene into the Leu2 locus in the strain thus obtained, PCR is performed using a genome of the cell as a template and a primer set of SEQ ID NOs. 65 and 66 as primers to examine gene deletion and gene introduction. As a result, *S. cerevisiae* CEN.PK2-1D (Δadh1::ldh, Δpdc1::ldh, Δcyb2::ldh, Δgpd1::ldh, mhpF) is identified.

(3.2) Construction and Introduction of Vector for ald6 Deletion

An acetaldehyde dehydrogenase 6 (ald6) gene deletion cassette is amplified by PCR using the deletion vector pUC57-ura3HA as a template and a primer set of SEQ ID NOs. 67 and 68 as primers. The sequences of SEQ ID NOs. 67 and 68 include a region which is replaced for the ald6 gene by recombination with a homologous sequence in a chromosome of *S. cerevisiae*.

In order to delete the ald6 gene from *S. cerevisiae* CEN.PK2-1D (Δadh1::ldh, Δpdc1::ldh, Δcyb2::ldh, Δgpd1::ldh, mhpF) strain, the prepared "ald6 deletion cassette" is introduced into the strain by heat shock transformation. After heat shock, cells are cultured in a minimal Ura-drop out medium as a selection marker at 30° C. for 3 days to delete the chromosomal ald6 gene. For genotyping of the prepared strain, PCR is performed using a genome of the prepared strain as a template and a primer set of SEQ ID NOs. 69 and 70 to examine deletion of the ald6 gene.

As a result, *S. cerevisiae* CEN.PK2-1D (Δadh1::ldh, Δpdc1::ldh, Δcyb2::ldh, Δgpd1::ldh, mhpF, Δald6) strain is identified.

(3.3) Construction and Introduction of Vector for EutE Introduction (3.3.1) Construction of Yeast Dual Function Overexpression Vector, pCS-Ex1

PCR is performed using a pRS426GPD vector which is widely used as a yeast overexpression vector and a primer set of SEQ ID NO. 71 and SEQ ID NO. 72 to obtain a DNA fragment of 689 bp (GPD promoter). This DNA fragment is cloned into a KpnI-treated pCtB1 vector (Genbank Accession Number KJ922019) using an In-fusion kit (Clonetech, cat. 639650), and introduced into an E. coli cloning strain, TOP10 strain (Invitrogen, cat. C4040-06) by a general method. After introduction, the strain is plated on an LB agar plate (Bacto Tryptone 10 g/L, Yeast Extract 5 g/L, NaCl 10 g/L, and Bacto Agar 15 g/L) containing 50 ug/ml of kanamycin, followed by incubation. From colonies formed, plasmid DNAs are isolated, and plasmids having the same sequence as SEQ ID NO. 73 are examined. As a result, a yeast dual function overexpression vector, pCS-Ex1 is identified. Here, the dual function includes a gene expression after genomic integration of a gene and a gene expression on a vector.

(3.3.2) Construction of Yeast Dual Function E. coli eutE Gene Overexpression Vector PCR is performed using genomic DNA of E. coli MG1655 strain and a primer combination of SEQ ID NO. 74 and SEQ ID NO. 75 so as to obtain a DNA fragment of 1447 bp, that is, EutE gene. This DNA fragment is mixed with a pCS-Ex1 vector which is treated with KpnI and SacI, and cloning is performed using an In-fusion kit (Clonetech cat. 639650), and introduced into an E. coli cloning strain, TOP10 strain (Invitrogen, cat. C4040-06) by a general method. After introduction, the strain is plated on an LB agar plate containing 50 ug/ml of kanamycin, followed by incubation. From colonies formed, plasmid DNAs are isolated, and plasmids having the same sequence as SEQ ID NO. 76 are examined. As a result, a yeast dual function overexpression vector, MD1040 is identified.

(3.3.3) Preparation of E. coli eutE Gene-Overexpressing Yeast

From the prepared MD1040 vector, a DNA fragment of 3985 bp is obtained by PCR using a primer combination of SEQ ID NO. 77 and SEQ ID NO. 78. This fragment is introduced into S. cerevisiae CEN.PK2-1D (Δadh1::ldh, Δpdc1::ldh, Δcyb2::ldh, Δgpd1::ldh, mhpF, Δald6) by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, colonies which are confirmed to have a DNA fragment of 4357 bp by PCR using a primer combination of SEQ ID NO. 79 and SEQ ID NO. 80 are selected. From genomic DNA of a native strain, a DNA fragment of 2300 bp is obtained by PCR using a primer combination of SEQ ID NO. 79 and SEQ ID NO. 80. The obtained clones are inoculated in an YPD medium (Bacto Peptone 20 g/L, Yeast Extract 10 g/L, and D-glucose 20 g/L), and cultured at 30° C. under shaking at 230 rpm, and then plated on a counter-selection medium containing 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). After 3 days, from colonies formed, colonies which are confirmed to have a DNA fragment of 2963 bp by PCR using a primer combination of SEQ ID NO. C3 and SEQ ID NO. C4 are selected. As a result, S. cerevisiae CEN.PK2-1D (Δadh1::ldh, Δpdc1::ldh, Δcyb2::ldh, Δgpd1::ldh, mhpF, Δald6, EutE) (hereinafter, referred to as "SP1130") is identified.

(4) Preparation of S. cerevisiae CEN.PK2-1D SP1130 (ΔRGT1)

(4.1) Construction and Introduction of Vector for RGT1 Gene Deletion

A RGT1 gene deletion cassette is prepared by PCR using the above described deletion vector pUC57-Ura3HA as a template and a primer set of SEQ ID NO. 81 and 82 as primers. The sequences of SEQ ID NOs. 81 and 82 contain a region which is substituted for the RGT1 gene by recombination with a homologous sequence in a chromosome of S. cerevisiae.

To delete the RGT1 gene from the S. cerevisiae CEN.PK2-1D SP1130 strain prepared in (3) of Example 1, the prepared "RGT1 gene deletion cassette" is introduced into the strain by heat shock transformation. After heat shock, the cells are cultured in a minimal Ura-drop out medium as a selection marker at 30° C. for 3 days to delete the chromosomal RGT1 gene. For genotyping of the prepared strain, PCR is performed using a genome of the prepared strain as a template and a primer set of SEQ ID NOs. 83 and 84 to examine deletion of the RGT1 gene.

As a result, S. cerevisiae CEN.PK2-1D SP1130 (ΔRGT1) strain is identified.

(5) Preparation of S. cerevisiae CEN.PK2-1D SP1130 ($P_{cyc1}$HXK2ΔRGT1)

(5.1) Preparation of $P_{cyc1}$ Fragment and Construction of Recombinant Vector

Further, in order to obtain a DNA fragment containing a CYC1 promoter ($P_{cyc1}$) (SEQ ID NO. 85), a chromosomal DNA (gDNA) of the wild-type Saccharomyces cerevisiae strain CEN.PK2-1D is extracted using a Genomic-tip system of Qiagen (Company), and polymerase chain reaction is performed using the gDNA as a template and a PCR HL premix kit (manufactured by BIONEER, hereinafter, the same). For $P_{cyc1}$ amplification, PCR is performed using primers of SEQ ID NOs. 86 and 87 for 30 cycles consisting of denaturation at 94° C. for 30 seconds, annealing at 52° C. for 30 seconds, and elongation at 72° C. for 30 seconds. A PCR product is cleaved with EcoRI and a DNA fragment thus obtained (hereinafter, referred to as "$P_{cyc1}$ cassette") is electrophoresed on a 0.8% agarose gel, followed by elution.

Figure 3:
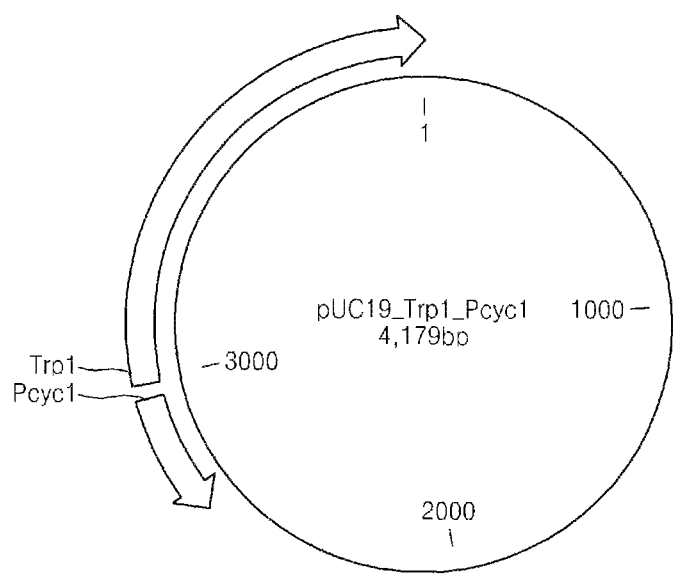
FIG. 3 shows a cleavage map of a pUC19_Trp1_Pcyc1 vector.

The pUC19-Trp1 vector (Appl Environ Microbiol. 2002 May; 68(5):2095-100) plasmid and the obtained $P_{cyc1}$ cassette are treated with the restriction enzyme EcoRI, respectively and ligated with each other to prepare a pUC19-Trp1-Pcyc1 vector. FIG. 3 shows the pUC19-Trp1-Pcyc1 vector.

(5.2) Preparation of S. cerevisiae CEN.PK2-1D SP1130 ($P_{cyc1}$HXK2)

To replace $P_{HXK2}$ with $P_{cyc1}$, the $P_{cyc1}$ cassette prepared in 5.1 of Example 1 is amplified to contain the HXT gene promoter sequence using primers of SEQ ID NOs. 88 and 89, mixed with 50% polyethylene glycol and a single stranded carrier DNA, and then incubated in a water bath at about 42° C. for about 30 minutes. The culture of Saccharomyces cerevisiae CEN.PK2-1D SP1130 is plated on a minimal solid medium containing no tryptophan (YSD, 6.7 g/L yeast nitrogen base without amino acids, 1.4 g/L Amino acid dropout mix (−trp)) and cultured at 30° C. for 3 days or longer. 10 colonies (mutant strain) are selected from colonies formed on the plate, and transferred onto a minimal solid medium containing no tryptophan, and also in a liquid medium having the same composition. Genomic DNA is isolated from the cultured strain using a commercial kit (Gentra Puregene Cell kit, Qiagen, USA). PCR is performed using the isolated genomic DNA of the mutant strain as a template and primers of SEQ ID NOs. 90 and 91 to confirm replacement of $P_{HXK2}$ with $P_{cyc1}$. Then, a PCR product is subjected to electrophoresis to examine replacement of $P_{HXK2}$ with $P_{cyc1}$. As a result, *S. cerevisiae* CEN.PK2-1D SP1130 ($P_{cyc1}$HXK2) is identified.

(5.3) Preparation of *S. cerevisiae* CEN.PK2-1D SP1130 ($P_{cyc1}$HXK2ΔRGT1)

To delete the RGT1 gene from the *S. cerevisiae* CEN.PK2-1D SP1130 ($P_{cyc1}$HXK2) prepared in (5.2) of Example 1, the "RGT1 gene deletion cassette" prepared in (4.1) of Example 1 is introduced into the strain by heat shock transformation. After heat shock, the cells are cultured in a minimal Ura-drop out medium as a selection marker at 30° C. for 3 days to delete the chromosomal RGT1 gene. For genotyping of the prepared strain, PCR is performed using a genome of the prepared strain as a template and a primer set of SEQ ID NOs. 83 and 84 to examine deletion of the RGT1 gene.

As a result, *S. cerevisiae* CEN.PK2-1D SP1130 ($P_{cyc1}$HXK2ΔRGT1) strain is identified.

(6) Preparation of *S. cerevisiae* CEN.PK2-1D SP1130 (ΔHXK2ΔRGT1)

(6.1) Construction and Introduction of Vector for HXK2 Gene Deletion

A HXK2 gene deletion cassette is prepared by PCR using the above described deletion vector pUC57-Ura3HA as a template and a primer set of SEQ ID NO. 92 and 93 as primers. The sequences of SEQ ID NOs. 92 and 93 contain a region which is substituted for the RGT1 gene by recombination with a homologous sequence in a chromosome of *S. cerevisiae*.

To delete the HXK2 gene from the *S. cerevisiae* CEN.PK2-1D SP1130 strain prepared in (3) of Example 1, the prepared "HXK2 gene deletion cassette" is introduced into the strain by heat shock transformation. After heat shock, the cells are cultured in a minimal Ura-drop out medium as a selection marker at 30° C. for 3 days to delete the chromosomal HXK2 gene. For genotyping of the prepared strain, PCR is performed using a genome of the prepared strain as a template and a primer set of SEQ ID NOs. 94 and 95 to examine deletion of the HXK2 gene.

As a result, *S. cerevisiae* CEN.PK2-1D SP1130 (HXK2) strain is identified.

(6.2) Preparation of *S. cerevisiae* CEN.PK2-1D SP1130 (ΔRGT1ΔHXK2)

To delete the RGT1 gene from the *S. cerevisiae* CEN.PK2-1D SP1130 (ΔHXK2) strain prepared in (6.1) of Example 1, the "RGT1 gene deletion cassette" prepared in (4.1) of Example 1 is introduced into the strain by heat shock transformation. After heat shock, the cells are cultured in a minimal Ura-drop out medium as a selection marker at 30° C. for 3 days to delete the chromosomal RGT1 gene. For genotyping of the prepared strain, PCR is performed using a genome of the prepared strain as a template and a primer set of SEQ ID NOs. 83 and 84 to examine deletion of the RGT1 gene.

2. Test of Growth, Glucose Consumption, and Lactate Productivity of Prepared Yeast Cell The prepared *S. cerevisiae* CEN.PK2-1D SP1130 (Δrgt1) and SP1130 ($P_{cyc1}$HXK2Δrgt1) strains are plated on an YPD solid medium (Yeast extract 1 (w/v) %, peptone 1 (w/v) %, and glucose 2 (w/v) %), respectively and cultured at 30° C. for 24 hours or longer. Then, the respective strains are inoculated in 25 ml of an YPD liquid medium containing 20 g/l of glucose in a 125 ml-flask, and cultured under aerobic conditions at 30° C. for 16 hours. The microaerobic conditions mean that the flask is sealed with a septum which does not allow ventilation, and agitated at 90 rpm. The control experiment is performed in the same manner, except that *S. cerevisiae* CEN.PK2-1D SP1130 strain is used.

Cell density in the culture is determined by measuring $OD_{600}$ value using a spectrophotometer, and the culture is centrifuged to discard a supernatant, and a cell pellet is inoculated in a fresh YPD liquid medium containing 60 g/l of glucose in a 125 ml-flask to $OD_{600}$ of 0.5. The flask is placed in a shaking incubator and the culture is incubated at 36° C. for 24 hours or longer under agitation at 90 rpm. The flask is sealed with a septum which does not allow ventilation.

During cultivation, samples are collected periodically, and centrifuged at about 13,000 rpm for about 10 minutes. Concentrations of various metabolites, lactate and glucose in a supernatant are analyzed by high-performance liquid chromatography (HPLC). The culture supernatant is filtered using a 0.45 um syringe filter and then L-lactate and glucose are quantified using an HPLC machine (Waters e2695 Separation Module instrument equipped with a Waters 2414 Differential Refractometer and a Waters 2998 Photodiode Array Detector (Waters, Milford, Mass.)). As an HPLC column, Aminex HPX-87H Organic Acid Analysis Column (300 mm×7.8 mm; Bio-Rad) that is equilibrated with 2.5 mM $H_2SO_4$ in water at 60° C. and at a flow rate of 0.5 mL/min is used.

Table 1 shows cell density, and glucose and lactate concentrations in the medium, which are measured after cultivation in the YPD medium under microaerobic conditions for 48 hours.

TABLE 1

| Strain | Cell growth (max $OD_{600}$) | Glucose consumption (g/L) | Lactate productivity (g/L) | Ethanol productivity (g/L) |
|---|---|---|---|---|
| SP1130 | 2.26 | 28.63 | 22.29 | 0.86 |
| SP1130($P_{cyc1}$HXK2) | 2.62 | 31.52 | 24.75 | 1.18 |
| SP1130(Δ rgt1) | 2.46 | 36.16 | 27.06 | 0.99 |
| SP1130($P_{cyc1}$HXK2 Δ rgt1) | 2.75 | 38.00 | 29.86 | 0.79 |
| SP1130(Δ HXK2) | 2.77 | 32.56 | 25.12 | 1.21 |
| SP1130(Δ HXK2 Δ rgt1) | 2.91 | 39.12 | 29.45 | 1.10 |

As in Table 1, SP1130 (Δrgt1) and SP1130 ($P_{cyc1}$HXK2Δrgt1) strains show 26% and 21% increases in glucose consumption and 21% and 21% increases in lactate production, compared to the control SP1130 and SP1130 ($P_{cyc1}$HXK2) strains, respectively. Therefore, when RGT1 gene is disrupted or activities of RGT1 gene and HXK2 gene are decreased, *S. cerevisiae* shows an unexpected increase in glucose consumption and lactate productivity.

3. Analysis of RNA Expression Levels of HXT Genes in Cells Having Decreased RGT1 and HXT2 Activities Expression levels of HXT1, HXT2, HXT3, HXT4, and HXT7 genes in *S. cerevisiae* CEN.PK2-1D SP1130 ($P_{cyc1}$HXK2ΔRGT1) strain are examined by qRT-PCT. Comparison of relative expression levels is performed by ΔΔCT, and TAF10 is used as a reference gene. The corresponding analysis is repeated three times. In detail, *S. cerevisiae* CEN.PK2-1D SP1130 ($P_{cyc1}$HXK2ΔRGT1) strain is cultured in a 125 ml-flask, and sampling is performed at 24 hours, 32 hours, and 48 hours after the culture. Total RNAs are extracted using an RNeasy mini kit (Qiagen co.). The extracted RNA is used as a template to synthesize cDNA using a SuperScript® III First-Strand Synthesis System (Invitrogen). Then, primers that specifically bind to respective HXT genes, specifically, forward and reverse primers (SEQ ID NOs. 96 through 105, respectively) that specifically bind to HXT1, HXT2, HXT3, HXT4, and HXT7 genes are mixed with IQ SYBR Green Supermix (Bio-rad) in accordance with the manufacturer's protocol, respectively and their relative expression levels are examined using a qRT-PCR detection system (CFX96 realtime PCR detection system, Bio-rad).

Table 2 shows relative RNA expression levels of HXT1, HXT2, HXT3, HXT4, and HXT7 in S. cerevisiae CEN.PK2-1D SP1130 ($P_{cyc1}$HXK2ΔRGT1) strain and S. cerevisiae CEN.PK2-1D SP1130 ($P_{cyc1}$HXK2) strain.

TABLE 2

| Type of RNA | Strain | 24 hrs after culture | 36 hrs after culture | 48 hrs after culture |
| --- | --- | --- | --- | --- |
| HXT1 | SP1130 ($P_{cyc1}$HXK2) | 16.41 | 1.00 | 2.30 |
|  | SP1130 ($P_{cyc1}$HXK2 Δ RGT1) | 37.82 | 12.20 | 2.41 |
| HXT2 | SP1130 ($P_{cyc1}$HXK2) | 1.03 | 1.00 | 1.02 |
|  | SP1130 ($P_{cyc1}$HXK2 Δ RGT1) | 57.43 | 49.25 | 5.73 |
| HXT3 | SP1130 ($P_{cyc1}$HXK2) | 1.00 | 4.67 | 2.20 |
|  | SP1130 ($P_{cyc1}$HXK2 Δ RGT1) | 5.03 | 18.30 | 21.74 |
| HXT4 | SP1130 ($P_{cyc1}$HXK2) | 0.00 | 1.00 | 0.00 |
|  | SP1130 ($P_{cyc1}$HXK2 Δ RGT1) | 8.09 | 0.88 | 50.88 |
| HXT7 | SP1130 ($P_{cyc1}$HXK2) | 1.00 | 1.26 | 0.00 |
|  | SP1130 ($P_{cyc1}$HXK2 Δ RGT1) | 7.46 | 3.24 | 1.99 |

As shown in Table 2, a high expression level of HXT1 is observed at an early stage of culture in the strain having the decreased RGT1 activity (SP1130 ($P_{cyc1}$HXK2ΔRGT1)), compared to its parent cell (SP1130 ($P_{cyc1}$HXK2)). Further, a transient high expression of HXT2 is observed at a lag phase in the strain having the decreased RGT1 activity, compared to its parent cell. A high expression of HXT3 is observed at a growth arrest in the strain having the decreased RGT1 activity, compared to its parent cell. Furthermore, a high expression of HXT4 is observed at a growth phase in the strain having the decreased RGT1 activity, compared to its parent cell. A high expression of HXT7 is observed at a stationary phase in the strain having the decreased RGT1 activity, compared to its parent cell. These results suggest that the strain having the decreased RGT1 activity increases the HXT expression levels, compared to its parent cell.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell comprising a genetic modification that decreases Restores Glucose Transport Protein 1 (RGT1) activity compared to the RGT1 protein activity of a parent cell thereof, wherein the genetically engineered yeast cell has increased productivity of a glycolytic intermediate compared to a parent cell thereof wherein the genetic modification is a disruption mutation of a gene encoding $RGT_1$.

2. The genetically engineered yeast cell of claim 1, wherein the genetically engineered yeast cell further comprises a genetic modification that decreases Hexokinase isoenzyme 2 (HXK2) protein activity compared to the HXK2 protein activity of a parent cell thereof.

3. The genetically engineered yeast cell of claim 2, wherein the genetic modification that decreases the HXK2 protein activity is a disruption mutation of a gene encoding HXK2.

4. The genetically engineered yeast cell of claim 1, wherein the yeast cell consumes glucose at an increased glucose consumption rate compared to the parent cell.

5. The genetically engineered yeast cell of claim 1, wherein the glycolytic intermediate is dihydroxyacetone phosphate (DHAP), glyceraldehyde-3-phosphate (GAP), pyruvate, or a combination thereof.

6. The genetically engineered yeast cell of claim 1, wherein the genetically engineered yeast cell has increased productivity of glycerol-3-phosphate (G3P), glycerol, acetyl-CoA, ethanol, acetic acid, lactate, a TCA cycle intermediate, or a combination thereof.

7. The genetically engineered yeast cell of claim 6, wherein the genetically engineered yeast cell has increased productivity of a TCA cycle intermediate comprising citric acid, itaconic acid, isocitrate, oxalosuccinate, alpha-ketoglutarate, succinic acid, succinyl-CoA, fumaric acid, malate, oxaloacetate, or a combination thereof, and the pyruvate-derived substance is a product derived from the TCA cycle intermediate and the product is 1,3-butanediol (1,3-BDO), 1,4-butanediol (1,4-BDO), butanol, isobutanol, or a combination thereof.

8. The genetically engineered yeast cell of claim 1, wherein the genetically engineered yeast cell further comprises an exogenous gene that encodes an enzyme that catalyzes conversion of pyruvate to lactate.

9. The genetically engineered yeast cell of claim 1, wherein the RGT1 protein has an amino acid sequence of SEQ ID NO. 1.

10. The genetically engineered yeast cell of claim 2, wherein the HXK2 protein has an amino acid sequence of SEQ ID NO. 3.

11. The genetically engineered yeast cell of claim 1, wherein the genetically engineered yeast cell is a strain belonging to *Saccharomyces, Zygosaccharomyces, Pichia, Kluyveromyces, Candida, Shizosaccharomyces, Issachenkia*, or *Hansenula*.

12. The genetically engineered yeast cell of claim 1, wherein the genetically engineered yeast cell further comprises a genetic modification that decreases the activity of an enzyme that catalyzes conversion of acetaldehyde to ethanol, an enzyme that catalyzes conversion of pyruvate to acetaldehyde, an enzyme that catalyzes conversion of lactate to pyruvate, an enzyme that catalyzes conversion of dihydroxyacetone phosphate (DHAP) to glycerol-3-phosphate (G3P), an enzyme that catalyzes conversion of glycerol-3-phosphate (G3P) to glycerol, an enzyme that catalyzes conversion of acetaldehyde to acetate, or a combination thereof.

13. The genetically engineered yeast cell of claim 12, wherein the enzyme that catalyzes conversion of acetaldehyde to ethanol belongs to EC 1.1.1.1, the enzyme that catalyzes conversion of pyruvate to acetaldehyde belongs to EC 4.1.1.1, the enzyme that catalyzes conversion of lactate to pyruvate belongs to EC 1.1.2.4 or EC 1.1.2.3, the enzyme that catalyzes conversion of DHAP to G3P belongs to EC 1.1.1.8, the enzyme that catalyzes conversion of glycerol-3-phosphate (G3P) to glycerol belongs to EC 3.1.3.21, and the enzyme that catalyzes conversion of acetaldehyde to acetate belongs to EC 1.2.1.4.

14. The genetically engineered yeast cell of claim 12, wherein the enzyme that catalyzes conversion of acetaldehyde to ethanol is alcohol dehydrogenase (ADH), the enzyme that catalyzes conversion of pyruvate to acetaldehyde is pyruvate decarboxylase (PDC), the enzyme that catalyzes conversion of lactate to pyruvate is lactate cytochrome-c oxidoreductase (CYB2), the enzyme that catalyzes conversion of DHAP to G3P is NAD-dependent glycerol-3-phosphate dehydrogenase (GPD), the enzyme that catalyzes conversion of glycerol-3-phosphate to glycerol is glycerol phosphate phosphatase (GPP), and the enzyme that catalyzes conversion of acetaldehyde to acetate is acetaldehyde dehydrogenase.

15. The genetically engineered yeast cell of claim 12, wherein a gene encoding the enzyme that catalyzes conversion of acetaldehyde to ethanol, a gene encoding the enzyme that catalyzes conversion of pyruvate to acetaldehyde, a gene encoding the enzyme that catalyzes conversion of lactate to pyruvate, a gene encoding the enzyme that catalyzes conversion of dihydroxyacetone phosphate (DHAP) to glycerol-3-phosphate (G3P), a gene encoding the enzyme that catalyzes conversion of glycerol-3-phosphate to glycerol, a gene encoding the enzyme that catalyzes conversion of acetaldehyde to acetate, or a combination thereof comprises a disruption mutation.

16. A method of producing a glycolytic intermediate or glycolytic intermediate-derived substance, the method comprising:
    culturing the genetically engineered yeast cell of claim 1 in a cell culture medium to obtain a culture, whereby the genetically engineered yeast cell produces a glycolytic intermediate or glycolytic intermediate-derived substance in the culture; and
    isolating the glycolytic intermediate from the culture.

17. The method of claim 16, wherein the culturing is performed under microaerobic conditions.

18. A method of producing a genetically engineered yeast cell having an ability to produce lactate, the method comprising:
    introducing a gene encoding an enzyme that catalyzes the conversion of pyruvate into lactate into a yeast cell; and
    disrupting a gene encoding an RGT1 protein in the yeast cell.

19. The method of claim 18, further comprising disrupting a gene encoding an HXK2 protein in the yeast cell.

* * * * *